US010830720B2

(12) United States Patent
Chiao

(10) Patent No.: US 10,830,720 B2
(45) Date of Patent: Nov. 10, 2020

(54) NON-INVASIVE SAMPLE-INTERROGATION DEVICE

(71) Applicant: THE BOARD OF REGENTS OF THE UNIVERSITY OF TEXAS SYSTEM, Austin, TX (US)

(72) Inventor: Jung-Chih Chiao, Austin, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 4 days.

(21) Appl. No.: 15/797,074

(22) Filed: Oct. 30, 2017

(65) Prior Publication Data

US 2018/0188211 A1 Jul. 5, 2018

Related U.S. Application Data

(63) Continuation-in-part of application No. PCT/US2017/046024, filed on Aug. 9, 2017.

(Continued)

(51) Int. Cl.

| | |
|---|---|
| ***G01N 27/02*** | (2006.01) |
| ***A61B 5/05*** | (2006.01) |
| ***A61B 5/024*** | (2006.01) |
| ***A61B 5/145*** | (2006.01) |
| ***B07C 5/344*** | (2006.01) |

(Continued)

(52) U.S. Cl.

CPC .......... *G01N 27/025* (2013.01); *A61B 5/024* (2013.01); *A61B 5/05* (2013.01); *A61B 5/055* (2013.01); *A61B 5/145* (2013.01); *B07C 5/344* (2013.01); *G01N 29/036* (2013.01); *G01N 33/491* (2013.01); *G01R 27/22* (2013.01); *G01R 33/34015* (2013.01); *A61B 5/0028* (2013.01); *G01N 24/087* (2013.01);

(Continued)

(58) Field of Classification Search

CPC ......... A61B 5/024; A61B 5/05; G01N 33/491

See application file for complete search history.

(56) References Cited

U.S. PATENT DOCUMENTS

| | | | | |
|---|---|---|---|---|
| 5,549,008 | A | 8/1996 | Beauducel | 73/861.04 |
| 2005/0150278 | A1 * | 7/2005 | Troxler | G01N 33/42 73/78 |

(Continued)

OTHER PUBLICATIONS

Chiao, et al., “Liquid Interrogator for Security Applications” IEEE Sensors Conferences, 2017.

(Continued)

*Primary Examiner* — Alvaro E Fortich

(74) *Attorney, Agent, or Firm* — Norton Rose Fulbright US LLP

(57) ABSTRACT

Embodiments of the present disclosure provide an interrogation device that is operable to apply one or more source signals to one or more coils surrounding a volume, where a material is disposed within the volume. Each of the one or more source signals may excite one of the one or more coils, and the behavior of each the one or more coils responsive to the exciting may be monitored. One or more parameters may be determined based on the behavior of each the one or more coils, and the one or more parameters may be utilized to generate a signature for the material within the volume. The signature may be compared to one or more signatures of known materials to identify the material within the volume.

20 Claims, 35 Drawing Sheets

Related U.S. Application Data

(60) Provisional application No. 62/395,218, filed on Sep. 15, 2016, provisional application No. 62/382,104, filed on Aug. 31, 2016.

(51) Int. Cl.

| | |
|---|---|
| ***A61B 5/055*** | (2006.01) |
| ***G01N 29/036*** | (2006.01) |
| ***G01R 27/22*** | (2006.01) |
| ***G01R 33/34*** | (2006.01) |
| ***G01N 33/49*** | (2006.01) |
| *A61B 5/00* | (2006.01) |
| *G01N 24/08* | (2006.01) |
| *G01N 29/02* | (2006.01) |
| *G01N 33/04* | (2006.01) |
| *G01N 33/14* | (2006.01) |

(52) U.S. Cl.

CPC .......... *G01N 29/022* (2013.01); *G01N 33/04* (2013.01); *G01N 33/14* (2013.01)

(56) References Cited

U.S. PATENT DOCUMENTS

| | | | | |
|---|---|---|---|---|
| 2005/0254058 | A1 | 11/2005 | Alphonse | 356/479 |
| 2006/0025664 | A1 | 2/2006 | Kim | 600/365 |
| 2007/0180892 | A1 | 8/2007 | Sunshine | 73/24.01 |
| 2008/0203281 | A1 | 8/2008 | Sanders | 250/227.18 |
| 2010/0164513 | A1 | 7/2010 | Rapoport | 324/633 |
| 2014/0182363 | A1* | 7/2014 | Potyrailo | G01N 27/026 73/64.53 |
| 2014/0187906 | A1 | 7/2014 | VoluSense | 600/409 |
| 2015/0226683 | A1* | 8/2015 | Feldman | A01J 5/0133 324/640 |
| 2016/0091544 | A1* | 3/2016 | Daneshmand | G01N 22/00 324/633 |
| 2017/0108471 | A1* | 4/2017 | Sturtevant | G01N 29/222 |

OTHER PUBLICATIONS

De Miranda and Pichorim, "Self-resonant frequencies of air-core single-layer solenoid coils calculated by a simple method," Electrical Engineering, vol. 97, No. 1, pp. 57-64, 2015.

Klein, et al., "Dual-mode microwave cavity for fast identification of liquids in bottles," in Microwave Symposium Digest (MTT), 2011 IEEE MTT-S International, Jun. 2011, pp. 1-4.

Knight. (2016) The self-resonant and self-capacitance of sonenoid coils. [Online]. Available: http://g3ynh.info/zdocs/magnetics/appendix/self_res/self-res.pdf.

Li, Guo, and Huang, "Characterisation of liquid properties by electrical capacitance tomography sensor for security applications," in Electronic Commerce and Security, 2009. ISECS '09. Second International Symposium on, vol. 1, May 2009, pp. 305-308.

Search Report and Written Opinion in International Application No. PCT/US2017/046024 dated Oct. 18, 2017.

Tashiro, et al., "Design of liquid detection sensor with low-frequency electromagnetic field," in Sensing Technology (ICST), 2013 Seventh International Conference on, Dec. 2013, pp. 578-581.

* cited by examiner

LabView Interface Panel

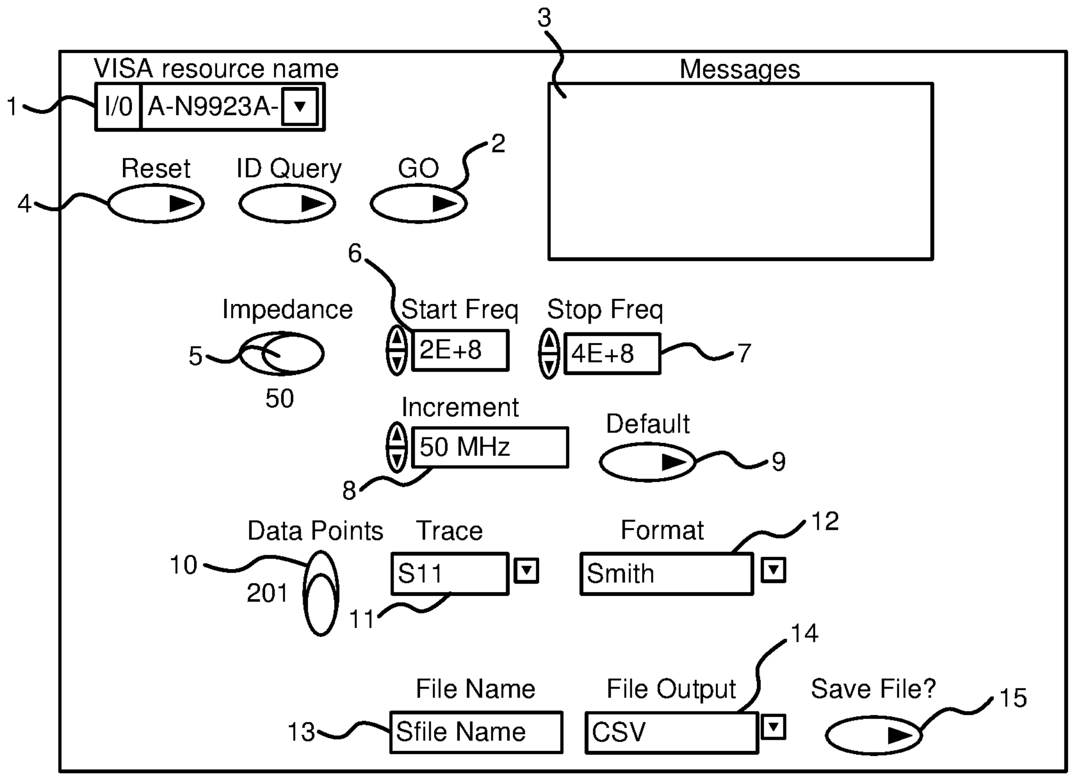

1. Instrument Select control
2. Go: activities continuous VNA operation
3. Messages: displays various information
4. Reset: sends reset command to VNA
5. Input impedance select (50/75Ω)
6. Starting measurement frequency
7. Ending measurement frequency
8. Frequency increment
9. Default settings (200MHz-400MHz, 50MHz step)
10. Measurement data point quantity
11. Measurement trace type (S11, S12, S21, S22)
12. Measurement view format (LogMag, Linear, VSWR Smith, etc.)
13. Output File Name
14. Output File Extension
15. Saves current trace to file

FIG. 31

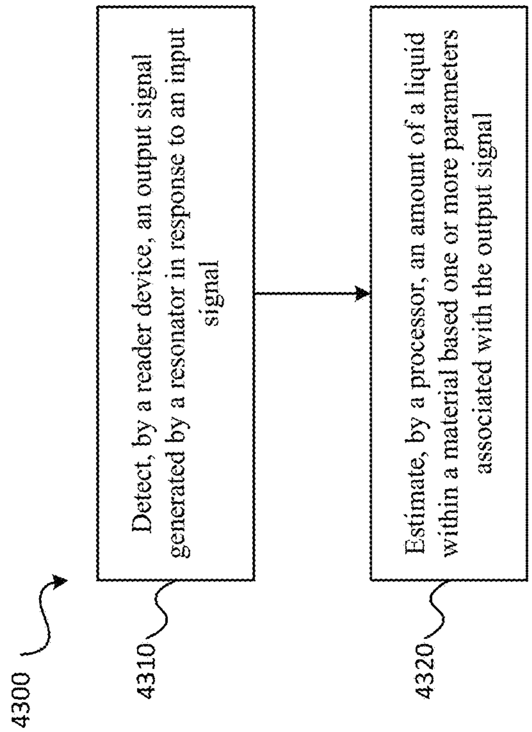
FIG. 43
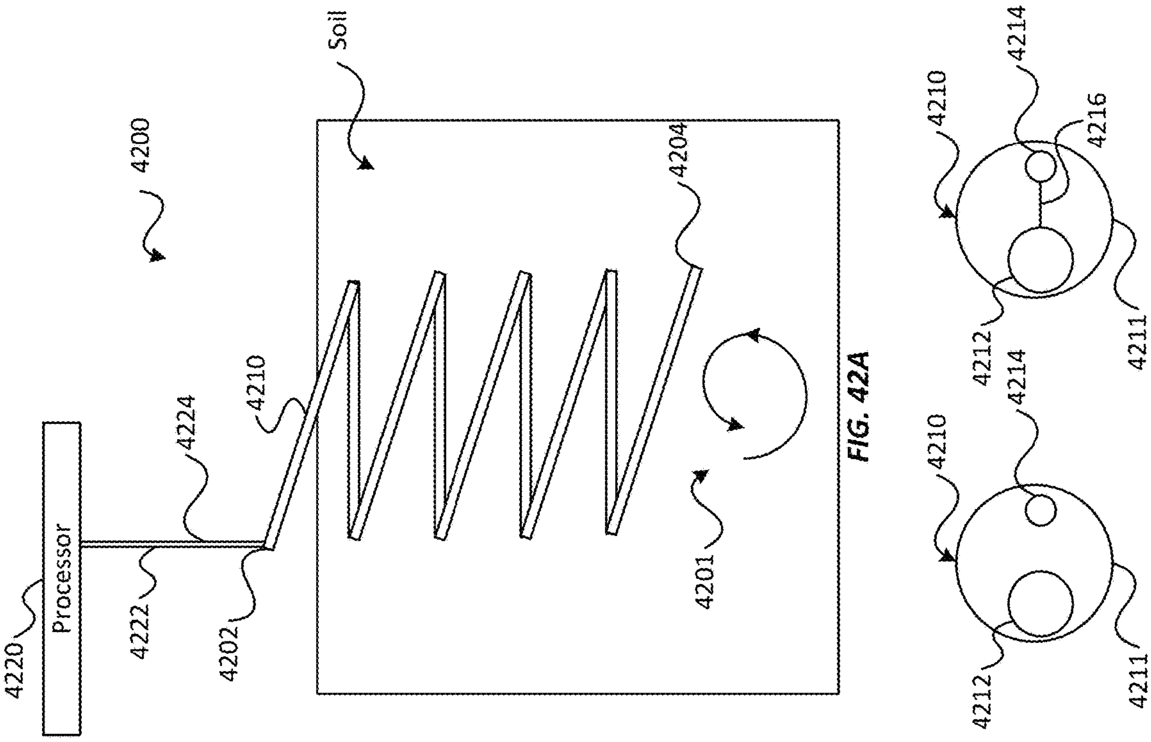
FIG. 42A
FIG. 42B
FIG. 42C

NON-INVASIVE SAMPLE-INTERROGATION DEVICE

CROSS-REFERENCE TO RELATED APPLICATIONS

This application is a continuation-in-part of International Application Number PCT/US2017/046024, filed Aug. 9, 2017, which claims priority to U.S. Provisional Patent Application No. 62/395,218 filed Sep. 15, 2016, and to United States Provisional Patent Application No. 62/382,104 filed Aug. 31, 2016, the contents of all of which applications are incorporated by reference.

FIELD OF INVENTION

The present disclosure is generally directed to non-intrusive materials analysis techniques, and more particularly to systems and methods for estimating liquid concentration of a material.

BACKGROUND

Typically, testing of liquids and other materials to determine the contents thereof is performed using chemically-reactive processes. Such processes introduce new substances into the sample being tested, which may cause a tested sample to become unfit for additional testing. In such scenarios, a different sample is needed for each different type of test to be performed, and is typically performed manually.

In addition to identifying types of liquids, it may be desirable to determine a quantity of liquid present in a material, such as an amount of water present in soil. This may provide valuable information to certain entities, such as farmers, environmental agencies, and other persons or groups. However, existing technologies for conducting such analysis, such as time-domain reflectrometry (TDR) devices, have several drawbacks. For example, TDR devices have high power consumption, and limited measurement capabilities (e.g., only measures resistance at surface of the sensor).

SUMMARY

The present disclosure provides systems, methods, and computer-readable storage media operable to analyze an unknown material to identify one or more characteristics of the material. In some embodiments, a material (e.g., an unknown material) may be placed in a volume (e.g., an interior channel of a body) that is surrounded by one or more coils. While the material is within the volume, the one or more coils may be excited, and the behavior of the one or more coils while excited may be monitored to observe one or more parameters associated with the behavior of the one or more coils. For example, the one or more parameters observed during the monitoring may be scattering parameters or S-parameters. The one or more parameters may be used to generate one or more signatures for the unknown material, which may then be compared to signatures of known materials to identify the presence of one or more of the known materials in the unknown material. For example, some embodiments may detect the presence of a first liquid, such as vodka, and may be operable to distinguish when the first liquid is present in its pure form and when the first liquid has been diluted by a second liquid, such as water. In some embodiments, the signature may be an Smith Chart generated based on the one or more parameters that were observed during excitement of the one or more coils.

In some embodiments, a plurality of signatures, such as a plurality of Smith Charts, may be generated. In embodiments, some of the plurality of signatures may be generated by exciting the coils at different frequencies, which may alter the behavior of the coils for a particular observation of the one or more parameters (e.g., the one or more parameters may exhibit different values at different frequencies). This may provide a plurality of signatures that may be used to identify the liquid. For example, a plurality of Smith Charts representing the behavior of the one or more coils when excited at different frequencies may be generated. Increasing the number of signatures for a liquid may increase the reliability of a system configured to identify a liquid according to embodiments.

Additionally, the present disclosure provides systems, methods, and computer-readable storage media operable to analyze volume of material to determine an amount of liquid within, or moisture content of the material. In embodiments, a resonator device may be disposed within a material, and a reader device may be configured to detect output signals generated by the resonator device. Input signals may be provided to the resonator device, and the input signals may be configured to induce a response by the resonator device. The resonator device may generate output signals representative of the resonator device's response to the input signals, and the output signals may be detected by the reader device. The reader device may be configured to analyze the output signals to determine one or more parameters associated with the input signals, and to estimate a moisture content of the material based on the one or more parameters associated with the input signals.

The term "coupled" is defined as connected, although not necessarily directly, and not necessarily mechanically. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially" and "approximately" may be substituted with "within [a percentage] of" what is specified, where the percentage includes 0.1, 1, 5, and 10%.

Further, a device or system that is configured in a certain way is configured in at least that way, but it can also be configured in other ways than those specifically described.

The terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. As a result, an apparatus that "comprises," "has," "includes," or "contains" one or more elements possesses those one or more elements, but is not limited to possessing only those elements. Likewise, a method that "comprises," "has," "includes," or "contains" one or more steps possesses those one or more steps, but is not limited to possessing only those one or more steps.

Any embodiment of any of the apparatuses, systems, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Some details associated with the embodiments described above and others are described below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

FIG. 31 is another diagram illustrating aspects of a graphical user interface (GUI) for configuring a system for interrogation of a sample of an unknown material;

FIG. 42A is a block diagram illustrating aspects of another system for determining an amount of liquid within a volume of a material according to embodiments of the present disclosure;

FIG. 42B is a block diagram illustrating aspects of a resonator configuration for use in a system for determining an amount of liquid within a volume of a material according to embodiments of the present disclosure;

FIG. 42C is a block diagram illustrating aspects of a resonator configuration for use in a system for determining an amount of liquid within a volume of a material according to embodiments of the present disclosure;

FIG. 43 is a flow diagram illustrating aspects of exemplary for determining an amount of liquid within a volume of a material according to embodiments of the present disclosure.

DETAILED DESCRIPTION OF ILLUSTRATIVE EMBODIMENTS

Figure 1:
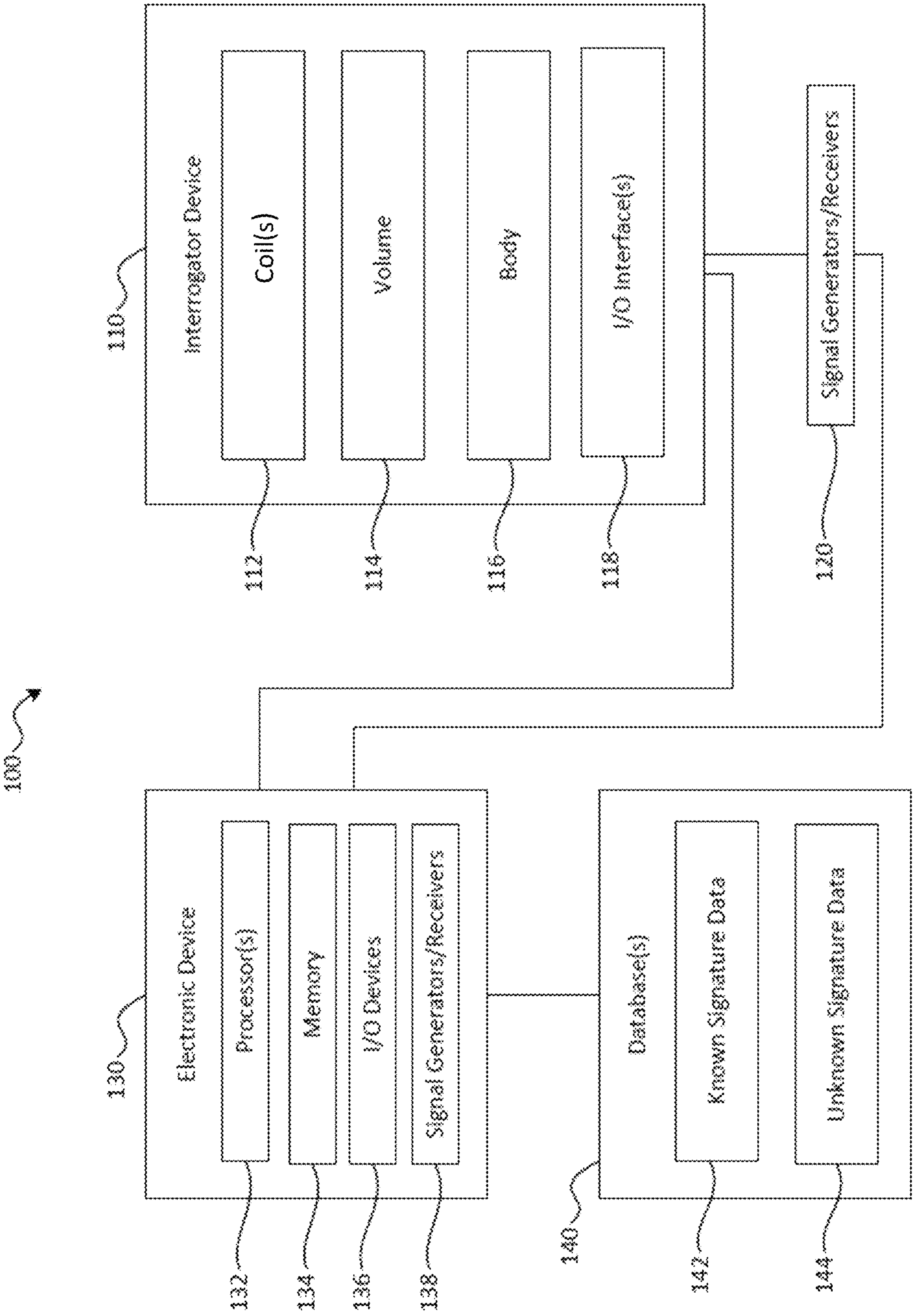
FIG. 1 is a block diagram of a system for identifying an unknown material according to embodiments of the present disclosure.

Referring now to the drawings, and more particularly to FIG. 1, an embodiment of a system operable to perform interrogation of a material (e.g., an unknown material) and to identify one or more characteristics of the material is shown as a system 100. For example, various components of system 100 may cooperate to allow an unknown material to be identified. In some embodiments, the material comprises water, alcohol, coffee, a soft drink, milk, oil, blood, or a combination thereof. It is noted however, that the exemplary materials described in the various embodiments of the present disclosure are provided for purposes of illustration, rather than by way of limitation. Thus, the present disclosure is not to be limited to the particular materials described herein, as the concepts of the various embodiments of the present disclosure can be readily applied to identification of other materials.

Where the unknown material is a liquid, the system 100 may interrogate a sample of the unknown liquid, and, as described in more detail below, based on the analysis, may identify one or more characteristics of the liquid, such as one or more types of liquid contained within the sample. For example, an exemplary system 100 configured according to embodiments of the present disclosure has been demonstrated to be operable to detect and/or identify the presence of various concentrations of alcohol in de-ionized water, as described in more detail below with reference to FIGS. 6-9. In some embodiments, other types of analysis may be performed by the system 100, such as to determine the moisture content of soil or when a liquid changes from a first state (e.g., a liquid) to a second state (e.g., a solid). Additional types and description of the analysis that may be performed using the system 100 are described below.

As shown in FIG. 1, interrogator device 110 comprises one or more coils 112, a volume 114, a body 116, and one or more input/output (I/O) interfaces 118. In alternate embodiments one or more single strip antenna(e) may be used in combination or as a replacement for the coils 112. Body 116 may define an interior channel, and volume 114 may be the space within the interior channel. A material that is to be tested/interrogated by system 100 may be placed directly within volume 114 (e.g., in the interior channel). In some embodiments, the material may be placed inside a container, such as a bottle, and the container placed in the volume 114. Interrogating a sample that has been placed in a container may allow the sample to be analyzed without corrupting or altering the sample, such by contamination of the sample with residue within the interior channel. This may result in analysis of samples with a higher degree of integrity and reduce the likelihood that the contents of the sample are incorrectly identified. This may also enable system 100 to be utilized for testing samples that need to remain sealed, as described in more detail below. In some embodiments, the volume 114 may be sized and dimensioned to accommodate a variety of container sizes. In an additional or alternative embodiment, the volume 114 may be sized and dimensioned to accommodate a single container size, such as a test tube or another type of container specifically sized and dimensioned to be received in the interior channel of body 116. Additionally, it is noted that utilizing samples placed in containers may reduce the upkeep and maintenance of the system 100. For example, if the material is placed directly within the volume 114, the interior channel of the body 116 may need to be cleaned prior to interrogating/analyzing an additional sample of material, whereas when the material is placed in a container, the interior channel of the body 116 may not need to be cleaned prior to interrogating/analyzing an additional sample of material. This may increase the speed at which different samples may be analyzed by system 100, which may provide performance enhancements in some applications of system 100, as described in more detail below.

In some embodiments, each of coil(s) 112 may be coupled to body 116. For example, each of coil(s) 112 may be wrapped around an exterior surface of body 116. In some embodiments, an insulating material or cover may be placed over or around the outer surface of body 116 and coil(s) 112. The insulating material or cover may help maintain coil(s) 112 in a desired alignment and prevent damage to the coil(s). In some embodiments, the coil(s) 112 may comprise two or more coils. In some embodiments, at least one of coil(s) 112 comprises two or more turns (e.g., four or more turns). In some embodiments, a maximum transverse dimension of volume 114 may be about or substantially 4 centimeters (cm) or larger. In some embodiments, body 116 comprises a pipe through which the material flows. For example, in an industrial liquid treatment or processing facility, such as a wastewater treatment facility or a chemical processing or manufacturing facility, body 115 may be a pipe through which a liquid or liquids flow, and coil(s) 112 may be wrapped around the pipe to perform analysis of the liquid flowing through the pipe.

As shown in FIG. 1, one or more I/O interfaces 118 may communicatively couple the interrogator device to device 130 and/or the one or more signal generators/receivers 120. More particularly, in some embodiments, I/O interface(s) 118 may couple each of coil(s) 112 to a respective one of the signal generators/receivers 138 of electronic device 130, or, in an additional or alternative embodiment, I/O interface(s) 118 may couple each of the one or more coils 112 to a respective one of the one or more signal generators/receivers 120. The one or more signal generators/receivers may be configured to excite each of coil(s) 112 with a respective source signal, as described in more detail below. The exciting of coil(s) 112 may induce a behavior at each of the one or more coils, and the behavior of each of coil(s) 112 in response to the excitement may be monitored by the respective ones of the one or more signal generators/receivers. One or more parameters representative of the behavior of each of coil(s) 112 may be monitored during the exciting of the coils. For example, exciting the coil(s) 112 with the respective source signal(s) may induce electromagnetic fields for each of the coil(s), and one or more parameters associated with coil(s) 112 and their respective electromagnetic field(s) may be observed, as described in more detail below.

In some embodiments, a matching circuit 122 may be coupled in series with the coil(s). The matching circuit 122 may be used to match the impedance between two points of the interrogator device 100, such that power transfer is optimized to the coil(s) 112. Optimizing power transfer to the coils(s) 112 may increase the sensitivity of the signatures by generating more precise parameters. For example, a Pi matching circuit may be used to generate higher quality factors in resonance when identifying de-ionized water. The matching circuit 122 may enhance sensitivity to other parameters used by the interrogator 100, as described in more detail below.

Electronic devices 130 may include a processor(s) 132, a memory 134, I/O devices 136, and the one or more signal generators/receivers 138. In some embodiments, memory 134 may store instructions that, when executed by the processor(s) 132, cause processor(s) 132 to perform operations to analyze a material, for example, as described in more detail below. In some embodiments, the instructions comprise a software program that may be executed by processor(s) 132 to control operations of system 100 during interrogation and/or analysis of an unknown material in accordance with embodiments of the present disclosure, as described in more detail below. For example, the software program may provide one or more graphical user interfaces (GUIs) that allow a user to configure one or more aspects of the interrogation and/or analysis, such as to configure one or more frequencies utilized to excite coil(s) 112 during interrogation and/or analysis of a sample of unknown material. Additionally, the one or more GUIs may include GUIs that enable the user to view one or more aspects of the analysis, such as to view information representative of one or more parameters observed during the analysis, as described in more detail below. Thus, the software program may provide a suite of tools and functionality that enable analysis of a material in accordance with embodiments of the present disclosure.

In some embodiments, signal generators/receivers 138 may be configured to excite coil(s) 112 and to generate information representative of one or more parameters of coil(s) 112 observed during the excitement of the coil(s) 112. In other embodiments the coil(s) may be used in addition to or replaced with antenna(e). In an additional or alternative embodiment, electronic device 130 may not include signal generators/receivers 138, and instead, may be communicatively coupled to one or more external signal generators/receivers 120 that is/are configured to excite coil(s) 112 and to provide to electronic device 130 information representative of one or more parameters of coil(s) 112 during the excitement. In some embodiments, signal generator(s)/receiver(s) 138 and/or signal generator(s)/receiver(s) 120 may comprise a vector network analyzer (VNA) configured to excite coil(s) 112 and provide information representative of observed parameters to electronic device 130. In some embodiments, irrespective of whether the signal generator(s)/receiver(s) are integral with or external to the electronic device, they may operate under control of electronic device 130. For example, the software program stored as instructions at memory 134 may provide one or more GUIs and tools to configure the analysis and interrogation of the material within interrogator device 110.

During the interrogation/monitoring of a material within interrogator device 110, one or more parameters may be observed for each of coil(s) 112 (e.g., based on the electromagnetic fields induced by the exciting of each of coil(s) 112). For example, in some embodiments, the one or more parameters observed during the monitoring may include: a self-resonance frequency, a reflection coefficient, a transmission coefficient, or a combination thereof. In some embodiments, the resonant frequencies may be indicated by the reflection and transmission coefficients. In some embodiments, the one or more signal generators/receivers may generate a data set that represents the one or more parameters observed during the monitoring as scattering parameters (S-parameters), as described in more detail below. The data set may be stored at a database, such as database 140, as unknown signature data 144, and may include values for each of the one or more parameters observed during the monitoring. For example, where the monitoring is performed with respect to scattering parameters, the data set may include a plurality of scattering parameters values observed over a range of frequencies, thus, providing a plurality of data points in a frequency range of interest (e.g., a frequency range at which the coils are excited during a particular analysis of a material or a particular portion of the analysis). It is noted that one or more of the observed parameters may vary depending on the configuration of each of coil(s) 112 (e.g., the number of wraps, dielectric materials proximate to each of the one or more coils 112, etc.) and the frequency of the source signal. In embodiments where the material is placed within volume 114 while inside a container, the container may be required to be a container specially purposed for use with system 100 (e.g., because interrogation of the same liquid in different containers comprised of different materials may cause coil(s) 112 to exhibit different parameters). Processor 132 of electronic device 130 may analyze the data set to determine a signature associated with a material within volume 114. For example, in some embodiments, the signature may be determined based on the one or more parameters observed during the monitoring. After determining the signature for the material undergoing interrogation, the processor 132 may retrieve one or more candidate signatures (e.g., from a data set of candidate signatures 142) from the data base 140, and compare the signature for the material undergoing interrogation to the one or more candidate signatures to identify one or more characteristics of the material. In some embodiments, the data set of candidate signatures may comprise signatures generated by observing the behavior of coil(s) 112 during interrogation of known materials. Thus, comparing the candidate signatures of the data set of candidate signatures 142 may enable a signature for an unknown material to be matched with a signature of a known material in order to identify the material. In some embodiments, the data set of candidate signatures may comprise a plurality of signatures for each known material. For example, multiple candidate signatures for a known material may be generated, where at least two of the candidate signatures are generated by interrogating a sample of the known material at different frequencies. The behavior of coil(s) 112 may vary depending on the frequency, and generating more candidate signatures at different frequencies may increase the reliability of material identifications performed by system 100. Additionally, in some embodiments, multiple signatures for a known material may be generated at a single frequency, which may provide more reliable analysis under conditions where other variables may affect the analysis, such as changed in the temperature of liquid and/or the ambient environment where the testing is performed. In some embodiments, the one or more characteristics may include an alcohol content of the material, a moisture content of the material (e.g., a moisture content of a sample of soil), a solids content of the material (e.g., a liquid material is transitioning to a solid, when the transition is complete, and the like), a plasma content of the material (e.g., a plasma content of a sample of blood), a temperature of the material, another characteristic, or a combination thereof.

In an embodiment, statistical analysis techniques may be utilized to perform the comparison of the unknown signature data 144 to the one or more candidate signatures 142. Such techniques may be utilized to determine whether the unknown signature data 144 matches a particular one of the one or more candidate signatures 142 to within a threshold tolerance or to within a threshold confidence interval. In an embodiment, the threshold tolerance and/or threshold confidence interval may be configured to provide a desired degree of certainty with respect to identifying the material. For example, testing of samples of different liquid materials using a device configured according to the embodiment illustrated in FIG. 1 has demonstrated that the system of FIG. 1 can identify a material as being pure (e.g., contains only one liquid) or contaminated (e.g., contains a primary liquid or material, such as milk, and one or more additional and different liquids and/or materials, such as alcohol, that have been mixed within primary liquid or material) with almost 100% accuracy. In an embodiment, the threshold tolerance and/or confidence interval may be configurable depending on a particular application of, and accuracy requirements for, the interrogation system.

In some embodiments, the one or more candidate signatures may correspond to signatures representative of at least one known material that were determined based one or more parameters observed while the at least one known material was disposed within volume 114 of interrogator device 110. In some embodiments, the one or more candidate signatures may be selected based at least in part on the frequency or frequencies used to excite coil(s) 112. For example, when coil(s) 112 is/are excited using a first set of frequencies, candidate signatures that were generated for known materials based on exciting the one or more coils at the first set of frequencies may be selected for comparison to the signature of the unknown material. In some embodiments, the frequency or frequencies at which the one or more coils are excited may be varied during the monitoring. For example, data representative of the behavior of the induced electromagnetic fields may be observed at a first set of one or more frequencies, and then the one or more frequencies may be modified and additional data representative of the behavior of the induced electromagnetic fields may be observed. Obtaining data at multiple frequencies may enable a more accurate identification of the material undergoing interrogation, such as to rule out known signatures that do not exhibit similar behaviors at one or more of the frequencies used to interrogate an unknown material and/or to identify known signatures that exhibit similar behaviors at one or more of the frequencies used to interrogate an unknown material. This may provide a coarse level of filtering that reduces the pool of known or candidate signatures that may correspond to the signature of the material undergoing interrogation. In some embodiments, comparing, at each of the set of frequencies, the determined parameter (or behavior) with the corresponding known parameter (e.g., known signature) comprises comparing a Smith chart of the determined parameter with a Smith chart of the corresponding known parameter, as described in more detail below. Additional aspects of embodiments for interrogating a material and techniques for identifying the material (and/or characteristics of the material) based on parameters observed during the interrogating are described below.

From the foregoing it is shown that embodiments of system 100 provide techniques for non-invasively interrogating and identifying a material (e.g., an unknown material) and/or characteristics of the interrogated material. That is, embodiments of the present disclosure enable interrogation and analysis of a sample of a material without corrupting or altering the sample, such by contamination of the sample with residue within the interior channel of body 116. This can result in analysis of samples with a higher degree of integrity and reduce the likelihood that the contents of the sample are incorrectly identified. Further, as described in more detail below, embodiments of system 100 have been demonstrated to identify materials with a high degree of reliability. Thus, the present embodiments may, for example, provide an improved technique for identifying unknown materials.

Figure 2:
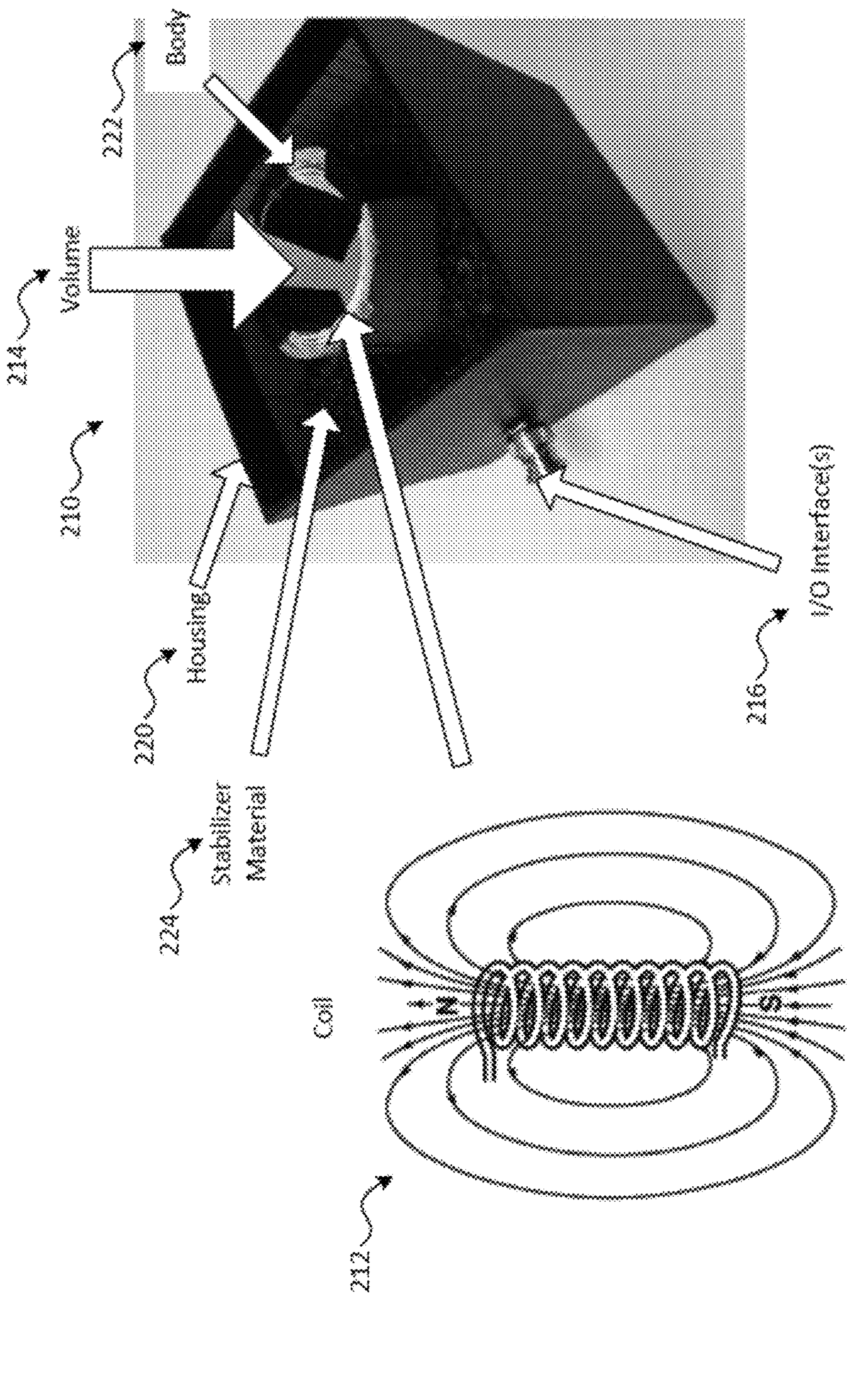
FIG. 2 is an illustrative embodiment of an interrogator device according to embodiments of the present disclosure.

FIG. 2 depicts an embodiment of the present interrogator devices and is shown as an interrogator device 210 (and may, for example, correspond to or be used in place of interrogator device 110 in system 100 of FIG. 1). In the embodiment shown, interrogator device 210 may comprise a housing 220, a coil 212, a body 222 defining an interior channel within a volume 214, and one or more I/O interfaces 216. In some embodiments, a stabilizer material 224 may be utilized to stabilize the orientation of body 222 within housing 220. Coil 212 may be wrapped around the body 222, and may be coupled to I/O interface(s) 216. During analysis, a sample of a material may be disposed within volume 214 (e.g., within the interior channel defined by body 222), coil 212 may be excited, and one or more parameters associated with an electromagnetic field associated with coil 212 may be observed. The unknown material may then be identified based on the observed parameters of the induced electromagnetic field of coil 212, as described in more detail below.

Figure 3A:
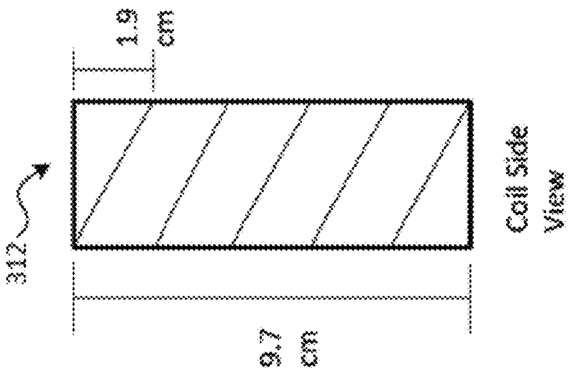
FIG. 3A is a diagrams illustrating a side view of a body and coil arrangement according to an embodiment of the present disclosure.
Figure 3B:
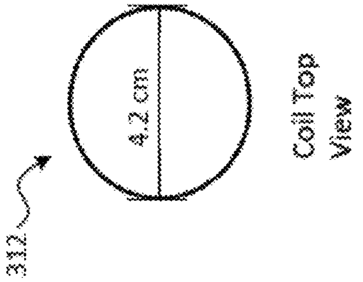
FIG. 3B is a diagrams illustrating a top view of a body and coil arrangement according to an embodiment of the present disclosure.
Figure 3C:
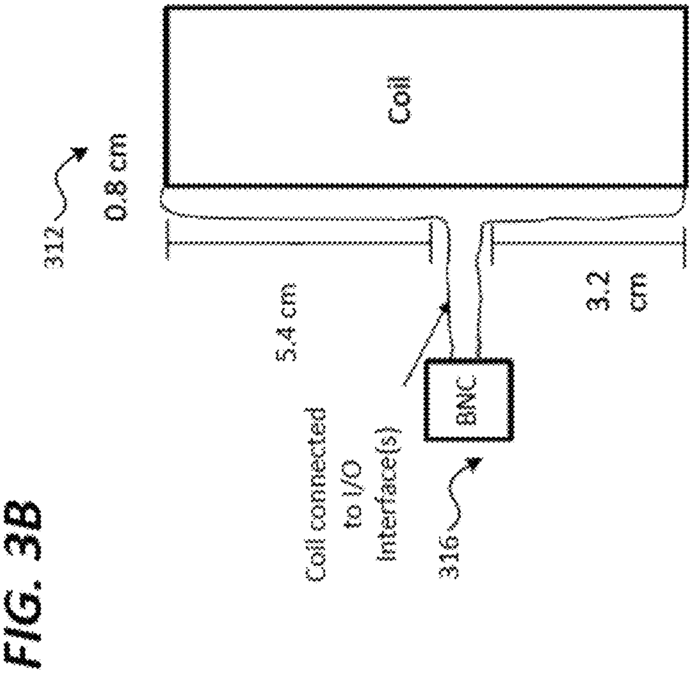
FIG. 3C is a diagrams illustrating a schematic view of a body and coil arrangement according to an embodiment of the present disclosure.

FIGS. 3A-3C illustrate respectively side, top, and schematic views of a body and coil arrangement according to one of the present embodiments. As shown in FIGS. 3A and 3B, the body (e.g., body 116 of FIG. 1) may have a height of approximately 9.7 centimeters (cm) and a width of approximately 4.2 cm. As shown in FIG. 3A, the coil (e.g., a coil 112 of FIG. 1) may comprise a plurality of wraps that surround the body and are spaced approximately 1.9 cm apart. It is noted that in additional or alternative embodiments, a plurality of coils may be provided, and each of the plurality of coils may have the same number of wraps or a different number of wraps. For example, an embodiment illustrating a body surrounded by two coils is illustrated with reference to FIG. 22, described in more detail below. In some embodiments, each of the plurality of coils may have a different spacing between consecutive wraps. As illustrated in FIG. 3C, the coil may be coupled to an I/O interface (e.g., I/O interface 118 of FIG. 1). The I/O interface may communicatively couple the coil to a signal generator/receiver (e.g., one of signal generator/receivers 138 of FIG. 1 or one of the signal generator/receivers 120 of FIG. 1).

Referring to FIG. 3D, the plurality of coils (e.g., 312*a*, 312*b*, and 312*c*) may each have a different radius. The plurality of coils may be arranged such that the plurality of coils each encircle the body 116, while, in alternate embodiments, the body 116 may encircle the plurality of coils. The plurality of coils may be arranged such that the coil with the largest radius will encircle the other coils in the plurality of coils. Different arrangements may be utilized by increasing or decreasing the number of coils in the plurality of coils, along with the distance from the plurality of coils to the body. The different arrangements can generate multiple signatures and may enable a more accurate identification of the material undergoing interrogation, such as to rule out known signatures that do not exhibit similar behaviors at a particular arrangement used to interrogate an unknown material and/or to identify known signatures that exhibit similar behaviors at a particular arrangement used to interrogate an unknown material. The parameters for a certain material determined at an arrangement may be used to cross check the parameters found in the material at other arrangements in order to generate more signatures. Generating more signatures at different arrangements may increase the reliability of material identifications performed by system 100.

Figure 4:
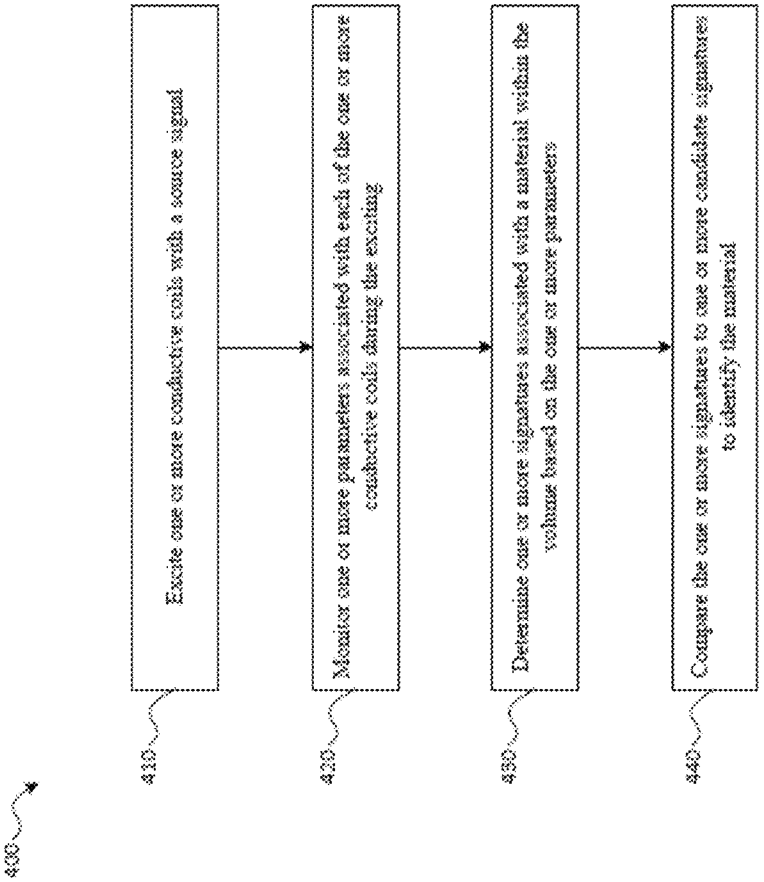
FIG. 4 is a flow diagram of an exemplary method for identifying an unknown material according to embodiments of the present disclosure.

Referring to FIG. 4, a flow diagram of an exemplary method for identifying an unknown material according to embodiments of the present disclosure is shown as a method 400. In some embodiments, method 400 may be stored as instructions in a memory (e.g., memory 134 of FIG. 1), and the instructions, when executed by a processor (e.g., processor 132 of FIG. 1), may cause the processor to perform the operations of method 400. At step 410, the method includes exciting one or more conductive coils with a source signal. As described above with reference to FIGS. 1-3, in some embodiments, the one or more conductive coils may surround a body defining an interior channel having a volume, and an unknown material may be retained within the volume during the interrogation/analysis. At step 420, the method includes monitoring one or more parameters associated with each of the one or more conductive coils during the exciting. As described above with reference to FIG. 1, and in more detail below with reference to FIGS. 5-20, in some embodiments, the one or more parameters associated with each of the one or more conductive coils may comprise: a scattering parameter (e.g., one or more S11, S12, S21, S22 parameters), a resonance frequency, or a combination thereof.

In some embodiments, a frequency of the source signal used to excite the coil(s) may be between approximately 200 megahertz (MHz) and approximately 400 MHz. In additional or alternative embodiments, the frequency range of the source signal may include frequencies below 200 MHz and/or frequencies above 400 MHz. In some embodiments, step 410 may further comprise varying a frequency of the source signal at which at least one of the one or more coils is excited, and step 420 may further comprise determining, during the monitoring, a resonance frequency associated with each of the one or more conductive coils. In some embodiments, the resonance frequency associated with each of the one or more conductive coils may be determined at least by: setting the frequency of the source signal at which each of the one or more conductive coils is excited to each of a set of frequencies; determining, for each frequency of the set of frequencies, one or more scattering parameters associated with each of the one or more conductive coils; and identifying, as the resonance frequency, the frequency of the set of frequencies at which the magnitude of scattering parameters are the smallest. For example, the source signal may be swept from a first frequency to a second frequency and one or more parameters may be observed as the frequency is swept. In some embodiments, multiple frequency sweeps may be performed, such as sweeping from the second frequency to a third frequency and one or more parameters may be observed as the frequency is swept. It is noted that embodiments may sweep the frequency of the source signal two or more times, or not at all depending on a particular configuration of the interrogation system. Thus, embodiments of the present disclosure should not be limited to a particular number of frequencies or frequency sweeps that may occur during interrogation/analysis of a material.

At step 430, the method includes determining one or more signatures associated with a material within the volume based on the one or more parameters, and, at step 440, the method includes comparing the one or more signatures to one or more candidate signatures to identify the material. In some embodiments, the one or more signatures may be represented as Smith Charts. In an additional or alternative embodiment, the signatures may correspond to plots of observed resonant frequencies of various scattering parameters (e.g., resonant frequencies observed based on one or more S11, S12, S21, S22, and/or the like parameters). In some embodiments, the amplitude and phase of the one or more parameters (e.g., one or more S-parameters) are measured over a range of frequencies during the monitoring (e.g., at 420), and then the one or more signatures are generated by plotting the measurements in a Smith Chart. In some embodiments, when the measurements are plotted in the Smith Chart, the shape and location of the curve of the Smith Chart may be used to determine whether the one or more signatures of the material within the volume can be identified as a particular known material. For example, if the unknown material is purported to be milk, the Smith Chart or Smith Charts generated by interrogation of the unknown material may be compared with one or more signatures corresponding to Smith Charts generated from liquid known to be milk. Because the shape and location of the curves of different materials on the Smith Chart are different, a person may be able to identify the unknown material as milk (e.g., when the shape and location of the curves of the different Smith Charts match) or determine that the unknown material is not milk (e.g., when the shape and location of the curves of the different Smith Charts do not match). Further, in some embodiments, an electronic device (e.g., the electronic device 130 of FIG. 1) may be programmed to perform pattern recognition operations that compare the shape and location of the curve in one or more signatures of the unknown material to one or more candidate signatures (e.g., signatures of known materials). Utilizing an electronic device programmed to perform pattern recognition on the shape and location of curves present in different Smith Charts may provide a finer degree of certainty (e.g., the pattern recognition performed by the electronic device may distinguish differences that may be too subtle for the human eye to catch). This may increase the accuracy of material identifications performed in accordance with embodiments.

In some embodiments, identification of the material may indicate one or more characteristics of the material. In some embodiments, the one or more characteristics of the material may include a temperature of the material. In an additional or alternative embodiment, the one or more characteristics of the material includes a moisture content of the material. For example, where the unknown material is a soil sample, the method may be operable to determine a moisture content of the soil. The moisture content of the soil may be determined by observing the one or more parameters representative of the behavior of the coils in response to excitation (e.g., the one or more parameters may change as the moisture content of the soil changes). It is noted that in some applications of embodiments of the present disclosure, the interrogator device may not include the body. For example, where the unknown material is a soil sample, the coil(s) may be placed at a desired depth within the soil to monitor the moisture content of the soil. In such an embodiment, the coils may be coated to prevent damage to the coils. It is noted that such configurations may provide improved performance over comparable technologies suitable for performing similar applications. For example, moisture sensors for measuring soil moisture content are limited to a small area local to the moisture sensor, whereas moisture sensors constructed according to embodiments of the present disclosure may provide for detection of soil moisture content over a much larger area, reducing the number of sensors required to cover a desired area. In another example, moisture sensors for measuring soil moisture came become inaccurate when the soil has other material; other material may include but is not limited to, organic matter, other types of soil and/or air. This may provide improved performance in applications where the moisture sensors are utilized to control sprinkler systems. Additionally, the cost to deploy a soil content moisture monitoring system configured according to embodiments may be significantly lower than existing moisture sensor systems.

In an additional or alternative embodiment, the one or more characteristics of the material may indicate a solids content of the material. For example, where the material comprises a liquid and solid, the method may be operable to determine a solids content of the material. The solids content may be determined by observing the one or more parameters of a liquid and generating a signature known to be of the liquid only, and then comparing the known signature to the signature of the liquid containing solid particles. Such techniques may be suitable for analysis of liquids containing nanoparticles, such as certain medications. For example, nanoparticles utilized in certain medicines must be thoroughly mixed to ensure an even distribution of the nanoparticles. The even distribution of the nanoparticles may be important for the medication to be effective, such as by ensuring that each dose contains a sufficient quantity of the nanoparticles. However, if the medication is not mixed effectively, nanoparticle concentrations at the top of the liquid may be lower than nanoparticle concentrations at the bottom of the liquid. Embodiments of the present disclosure may enable a signature of a liquid containing nanoparticles that is known to have been mixed to provide an even distribution of the nanoparticles to be generated. Subsequent mixtures of the liquid may be interrogated according to embodiments and the signature of the subsequent mixtures may be compared to the signature of the sufficiently mixed liquid to determine whether the subsequent mixtures comprise an even distribution of the nanoparticles. For example, mixtures comprising an uneven distribution of nanoparticles may exhibit different signatures than the mixture comprising the even distribution of the nanoparticles.

In an additional or alternative embodiment, the one or more characteristics of the material may indicate a plasma content of the material. For example, where the material comprises blood, the method may be operable to determine a plasma content of the blood. For example, samples of blood containing different plasma concentrations may exhibit different signatures when analyzed using method 400. Signatures of samples of blood containing an unknown plasma concentration may be compared to samples of blood containing known plasma concentrations to determine the plasma concentration of the unknown samples. Additionally or alternatively, embodiments may be utilized to determine whether blood is suitable for use in medical procedures. For example, donated blood is generally believed to have a particular shelf-life when stored under particular storage conditions, and after the particular shelf-life has passed, the blood is either disposed of or expensive and time consuming chemical processes must be performed to see if the blood is suitable for use in a medical procedure. Embodiments of the present disclosure may enable donated blood to be interrogated at the time the blood is stored to generate a signature for that particular blood, and when the blood is to be used, the blood could be interrogated a second time and the signature generated during the second interrogation may be compared to the signature generated when the blood was initially stored. If the signatures match, or match to within a threshold tolerance, the blood may be determined suitable for use in a medical procedure without requiring the costly and time consuming chemical analysis. This may enable blood to be stored for longer than the particular shelf-life presently utilized today, which may help ease the demand for blood donations and increase the supply of blood available for medical procedures. Further, the interrogation provided by embodiments of the present disclosure may be performed quickly (e.g., within a few seconds), allowing the determination that the blood is suitable for medical use to be performed quickly.

In an additional or alternative embodiment, the one or more characteristics of the material may be used to identify a liquid. For example, as described in more detail below, a device operating in accordance with the method has been demonstrated to be operable to identify unknown liquids containing water, alcohol, coffee, a soft drink, milk, oil, blood, or a combination thereof. Identification of liquids may provide useful applications in many industries. For example, at airports, mothers often try to bring breastmilk onto an airplane, but are forced to throw the breastmilk out when passing through airport security. Embodiments of the present disclosure enable a signature for milk to be generated, and then the signature known to be milk may be compared to a signature generated from a sample of breastmilk in order to confirm that the sample is indeed breastmilk. In some embodiments, the breastmilk may be required to be in a specialized container specially purposed for being analyzed by an interrogation system configured according to embodiments. This allows the sample to be interrogated non-intrusively, allowing the breastmilk to remain suitable for feeding a child (e.g., the container does not need to be opened during the analysis). Further, as described below, embodiments enable identification of whether a liquid, such as milk, has been diluted with another liquid. Thus, the analysis techniques of embodiments are sophisticated enough to detect attempts to conceal one type of liquid in another type of liquid, such as milk. Additional aspects of methods for interrogating and identifying an unknown material in accordance with embodiments of the present disclosure are illustrated and described below with reference to FIGS. 23-30.

Figure 5:
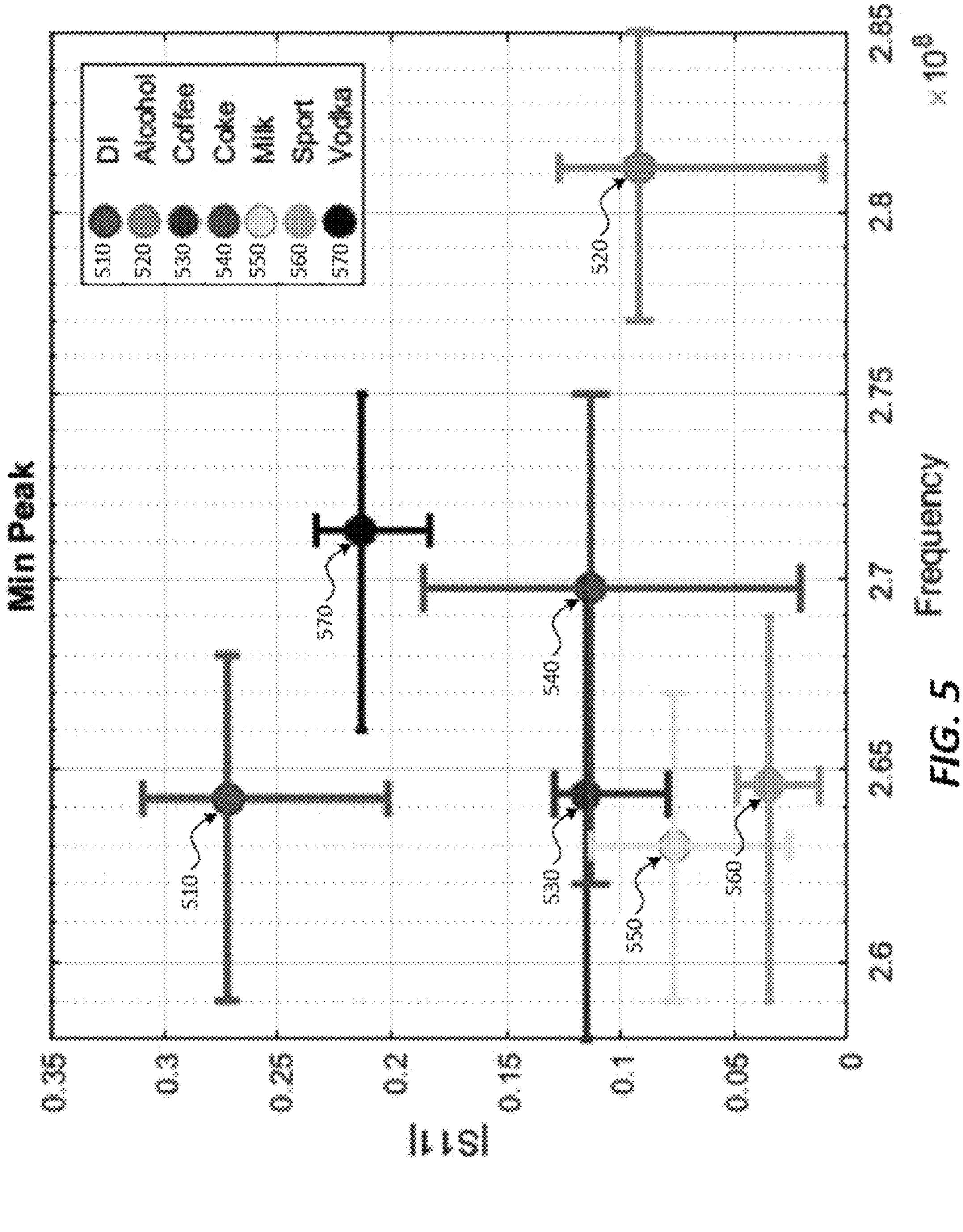
FIG. 5 is a graph illustrating various characteristics of different liquids that have been interrogated according to embodiments of the present disclosure.

Referring to FIG. 5, a graph illustrating various characteristics of different liquids that have been interrogated according to embodiments of the present disclosure is shown. As illustrated in FIG. 5, S-parameters, and in particular the |S11| parameter, have different minimum peaks for different liquids. For example, in FIG. 5, minimum peaks for deionized (DI) water 510, alcohol 520, coffee 530, a soda 540, milk 550, a sports drink 560, and vodka 570 are shown. As illustrated in FIG. 5, each of these liquids exhibits a minimum peak that is distinguishable from the minimum peaks of the other liquids in terms of the frequency at which the |S11| minimum peak occurs and/or the magnitude of the minimum peak. During interrogation of an unknown liquid according to embodiments of the present disclosure, an unknown liquid may be identified as one of the listed types of liquids by observing the minimum |S11| peak at different frequencies.

For example, the unknown liquid may be placed within volume 114 of interrogator device 110 and coil(s) 112 may be excited at one or more frequencies by the signal generator/receiver 138 of the electronic device 130. signal generator/receiver 138 of electronic device 130 may monitor the behavior of coil(s) 112 during the excitement to determine one or more parameters, such as one or more S-parameters, representative of coil(s) 112 during the excitement. If the one or more determined parameters includes an |S11| min peak having a magnitude of approximately 0.11 at an interrogation frequency of approximately 2.71, the unknown liquid likely contains a soda drink, such as soda drink 540, and electronic device 130 of FIG. 1 may identify the liquid as containing a soda drink. In some embodiments, the liquid may be identified as containing a soda drink by creating a signature based on the observed parameters, and then compare the signature observed during interrogation of the unknown liquid (e.g., during the exciting of coil(s) 112 by signal generator/receiver 138) to one or more signatures of known liquids to determine whether the signature generated based on parameters observed during interrogation of the unknown liquid matches any of the one or more signatures of the known liquids. In some embodiments, the one or more signatures of the known liquids may be stored in a database (e.g., as known characteristic data 142 at database 140 of FIG. 1). It is noted that the liquid identification techniques of embodiments are capable of identifying additional liquids than those shown in FIG. 5, and that the liquids and their corresponding minimum |S11| peaks are shown for purposes of illustration, rather than by way of limitation.

Figure 6:
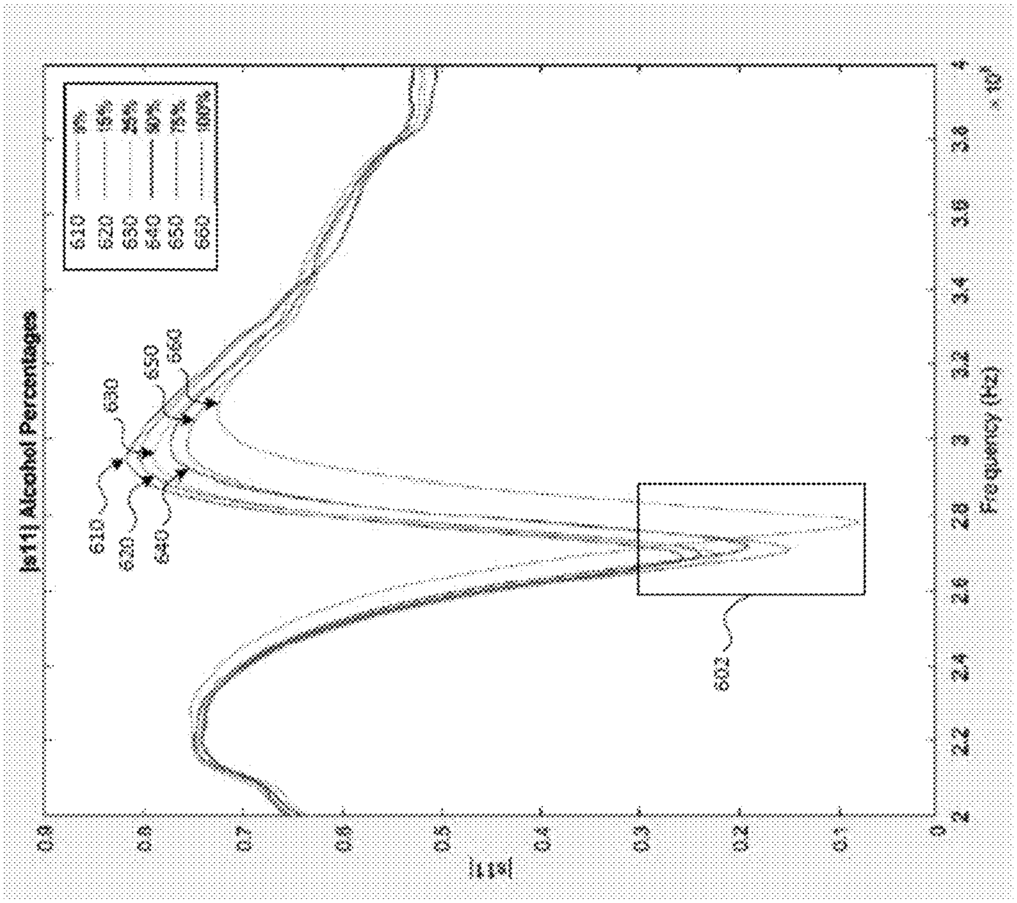
FIG. 6 is a chart illustrating characteristics observed during interrogation of liquids containing alcohol at different concentrations according to embodiments of the present disclosure.

Referring to FIG. 6, a chart illustrating characteristics observed during interrogation of liquids containing alcohol at different concentrations according to embodiments of the present disclosure are shown. In some embodiments, the information illustrated in FIG. 6 was observed using the system 100 of FIG. 1 and illustrates a plot of values representing the log magnitude for various observed values of an S-parameter (e.g., S11) during interrogation of a liquid by a device configured according to the embodiment illustrated in FIG. 1, as described in more detail below. For example, liquids containing different concentrations of alcohol may be placed within volume 114 of interrogator device 110 and coil(s) 112 may be excited at one or more frequencies by signal generator/receiver 138 of electronic device 130. Signal generator/receiver 138 of electronic device 130 may monitor the behavior of coil(s) 112 during the excitement to determine one or more parameters, such as one or more S-parameters, representative of coil(s) 112 during the excitement, as described above with reference to FIGS. 1-4. In FIG. 6, observed |S11| values for various concentrations of alcohol are shown at a range of frequencies (e.g., from approximately 2 Hz to approximately 4 Hz). The various concentrations of alcohol include a 5% concentration of alcohol 610, a 15% concentration of alcohol 620, a 25% concentration of alcohol 630, a 50% concentration of alcohol 640, a 75% concentration of alcohol 650, a 100% concentration of alcohol 660. As shown at box 602, minimum |S11| peaks for the different concentrations of alcohol 610-660 are observed at frequencies of approximately 2.7-2.8 Hz and have an |S11| magnitude ranging from approximately 0.1 to 0.27. In some embodiments, this information may be used to generate one or more signatures that may be stored (e.g., as part of known characteristic data 142 of FIG. 1) at a database (e.g., database 140 of FIG. 1). Once stored, these signatures may be compared to signatures of an unknown liquid to determine whether the liquid contains alcohol at one of the various concentrations illustrated in FIGS. 6-9.

Figure 7:
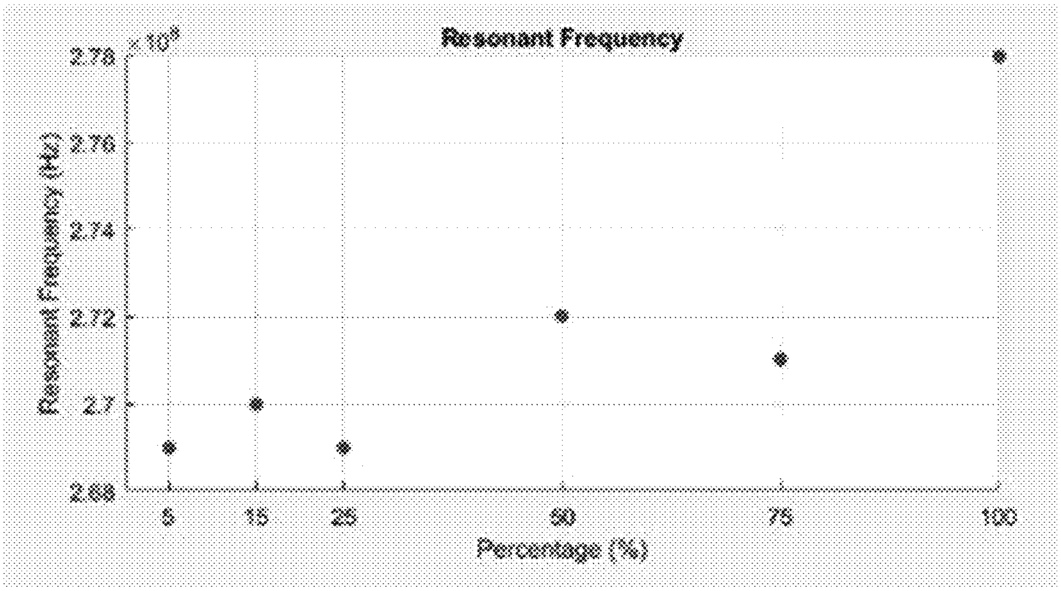
FIG. 7 is a diagram illustrating a plot of resonant frequencies observed during interrogation of liquids containing alcohol at different concentrations.

Referring to FIG. 7, a diagram illustrating a plot of resonant frequencies observed during interrogation of liquids containing alcohol at different concentrations is shown. In some embodiments, the information illustrated in FIG. 7 was generated based on information observed using system 100 of FIG. 1 (e.g., placing liquids containing different concentrations of alcohol within volume 114 of interrogator device 110, exciting coil(s) 112 at one or more frequencies by signal generator/receiver 138 of electronic device 130, and monitoring the behavior of coil(s) 112 during the excitement to determine one or more parameters). In some embodiments, the points plotted in FIG. 7 correspond to the different concentrations of alcohol illustrated with reference to FIG. 6. In some embodiments, the resonant frequencies illustrated in FIG. 7 may be utilized to generate signatures representative of the various concentrations of alcohol and the signatures generated based on the resonant frequency data illustrated in FIG. 7 may be stored (e.g., as part of known characteristic data 142 of FIG. 1) at a database (e.g., database 140 of FIG. 1). Once stored, these signatures may be compared to signatures of an unknown liquid to determine whether the liquid contains alcohol at one of the various concentrations illustrated in FIGS. 6-9.

Figure 8:
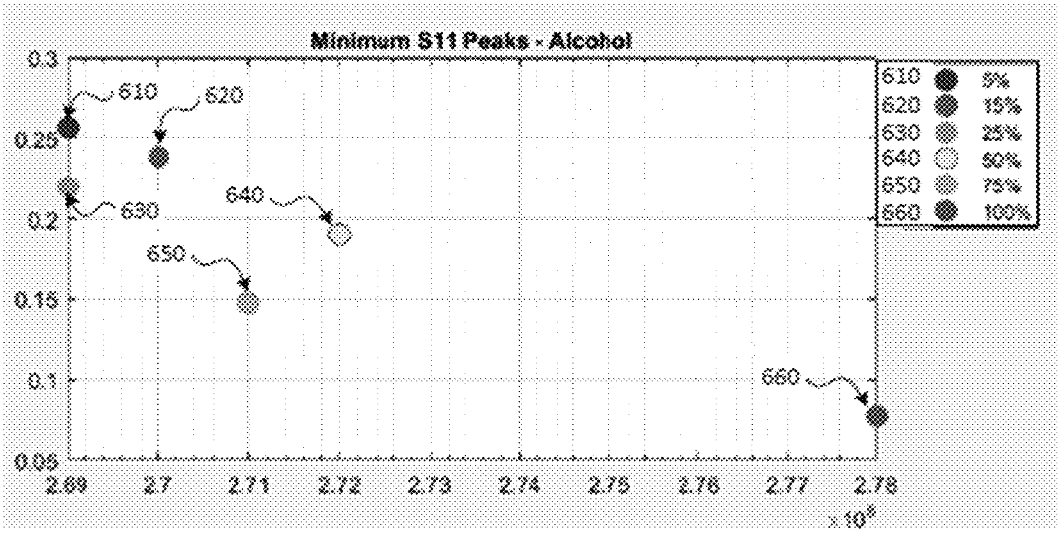
FIG. 8 is a diagram illustrating a plot of the minimum |S11| peaks observed during interrogation of liquids containing alcohol at different concentrations.

Referring to FIG. 8, a diagram illustrating a plot of the minimum |S11| peaks observed during interrogation of liquids containing alcohol at different concentrations is shown. In some embodiments, the information illustrated in FIG. 8 was generated based on information observed using system 100 of FIG. 1 (e.g., placing liquids containing different concentrations of alcohol within volume 114 of interrogator device 110, exciting coil(s) 112 at one or more frequencies by signal generator/receiver 138 of electronic device 130, and monitoring the behavior of coil(s) 112 during the excitement to determine one or more parameters). As illustrated in FIG. 8, a liquid containing an approximately 5% concentration of alcohol will exhibit a minimum |S11| peak having a magnitude of approximately 0.25 at a frequency of approximately 2.69 Hz, a liquid containing an approximately 15% concentration of alcohol will exhibit a minimum |S11| peak having a magnitude of approximately 0.24 at a frequency of approximately 2.7 Hz, a liquid containing an approximately 25% concentration of alcohol will exhibit a minimum |S11| peak having a magnitude of approximately 0.22 at a frequency of approximately 2.69 Hz, a liquid containing an approximately 50% concentration of alcohol will exhibit a minimum |S11| peak having a magnitude of approximately 0.19 at a frequency of approximately 2.72 Hz, a liquid containing an approximately 75% concentration of alcohol will exhibit a minimum |S11| peak having a magnitude of approximately 0.15 at a frequency of approximately 2.71 Hz, and a liquid containing an approximately 100% concentration of alcohol will exhibit a minimum |S11| peak having a magnitude of approximately 0.06 at a frequency of approximately 2.78 Hz. In some embodiments, the minimum |S11| peaks illustrated in FIG. 8 may be utilized to generate signatures representative of the various concentrations of alcohol and the signatures generated based on the resonant frequency data illustrated in FIG. 8 may be stored (e.g., as part of known characteristic data 142 of FIG. 1) at a database (e.g., database 140 of FIG. 1). Once stored, these signatures may be compared to signatures of an unknown liquid to determine whether the liquid contains alcohol at one of the various concentrations illustrated in FIGS. 6-9.

Figure 9:
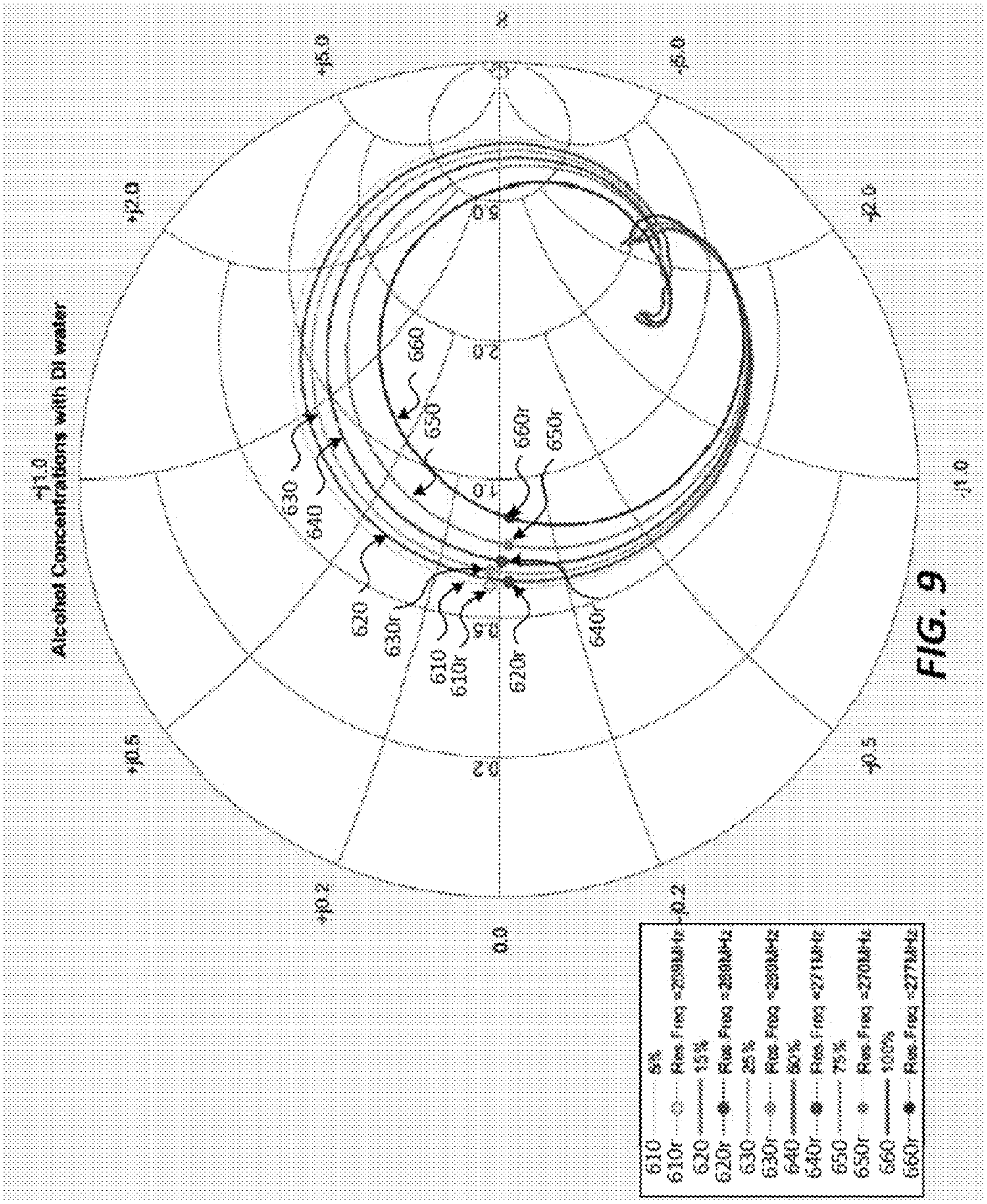
FIG. 9 is a diagram illustrating Smith charts generated based on observations during interrogation of liquids containing alcohol at different concentrations.

Referring to FIG. 9, a diagram illustrating Smith charts generated based on observations during interrogation of liquids containing alcohol at different concentrations is shown. In some embodiments, the information illustrated in FIG. 9 was generated based on information observed using system 100 of FIG. 1. As illustrated in FIG. 9, each of the different concentrations of alcohol is uniquely represented on a Smith chart, and the resonant frequencies (e.g., the resonant frequencies illustrated in FIG. 7) are illustrated as circles having labels corresponding to their counterpart concentrations with an "r" appended to the end of the label (e.g., the circle 610*r* represents the resonant frequency corresponding to a 5% concentration of alcohol 610, etc.). In some embodiments, the various Smith charts for each concentration of alcohol illustrated in FIG. 9 may be utilized to generate signatures representative of the various concentrations of alcohol, and the signatures generated based on the Smith charts illustrated in FIG. 9 may be stored (e.g., as part of known characteristic data 142 of FIG. 1) at a database (e.g., database 140 of FIG. 1). Once stored, these signatures may be compared to signatures of an unknown liquid to determine whether the liquid contains alcohol at one of the various concentrations illustrated in FIGS. 6-9. As shown in FIG. 9, Smith chart 660 corresponding to a sample of pure alcohol can be visually distinguished from samples of alcohol that have been diluted. In some embodiments, when determining whether a liquid purported to be alcohol is analyzed, a Smith chart known to be generated from pure alcohol and a Smith chart of the sample purported be alcohol may be displayed at a display device, and an operator may be able to determine whether the sample is what it is purported to be simply by viewing the displayed Smith charts. In additional or alternative embodiments, a system, such as the system 100 of FIG. 1, may compare the Smith charts and provide an output that indicates whether the sample is what it is purported to be.

Figure 10:
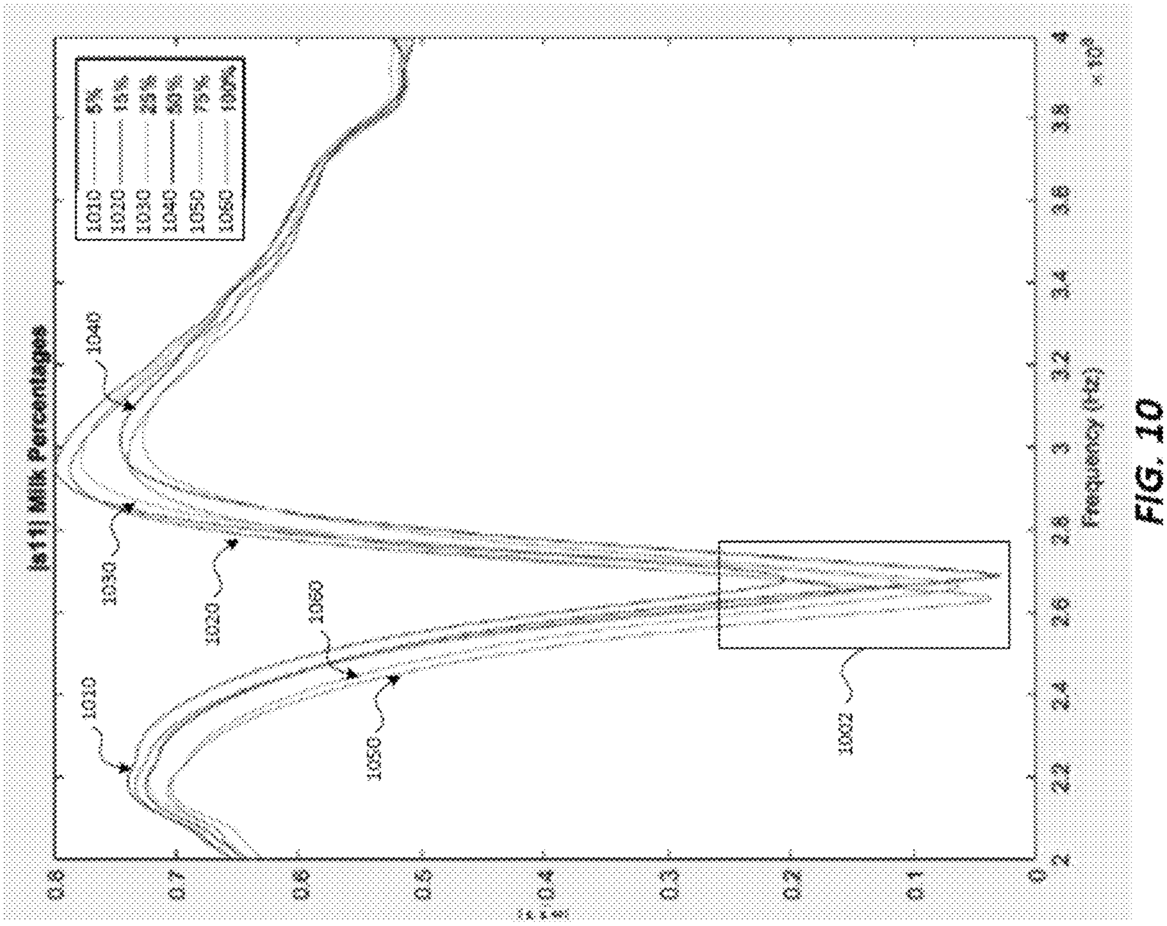
FIG. 10 is a chart illustrating characteristics observed during interrogation of liquids containing milk at different concentrations according to embodiments of the present disclosure.

Referring to FIG. 10, a chart illustrating characteristics observed during interrogation of liquids containing milk at different concentrations according to embodiments of the present disclosure are shown. In some embodiments, the information illustrated in FIG. 6 was observed using the system 100 of FIG. 10 and illustrates a plot of values representing the log magnitude for various observed values of an S-parameter (e.g., S11) during interrogation of a liquid by a device configured according to the embodiment illustrated in FIG. 1, as described in more detail below. For example, liquids containing different concentrations of milk may be placed within volume 114 of interrogator device 110 and coil(s) 112 may be excited at one or more frequencies by signal generator/receiver 138 of electronic device 130. Signal generator/receiver 138 of electronic device 130 may monitor the behavior of coil(s) 112 during the excitement to determine one or more parameters, such as one or more S-parameters, representative of coil(s) 112 during the excitement, as described above with reference to FIGS. 1-4. In FIG. 10, observed |S11| values for various concentrations of milk are shown at a range of frequencies (e.g., from approximately 2 Hz to approximately 4 Hz). In some embodiments, the information illustrated in FIG. 10 was observed using system 100 of FIG. 1. The various concentrations of milk include a 5% concentration of milk 1010, a 15% concentration of milk 1020, a 25% concentration of milk 1030, a 50% concentration of milk 1040, a 75% concentration of milk 1050, a 100% concentration of milk 1060. As shown at box 1002, minimum |S11| peaks for the different concentrations of milk 1010-1060 are observed at frequencies of approximately 2.6-2.7 Hz and have an |S11| magnitude ranging from approximately 0.03 to 0.2. In some embodiments, this information may be used to generate one or more signatures that may be stored (e.g., as part of known characteristic data 142 of FIG. 1) at a database (e.g., database 140 of FIG. 1). Once stored, these signatures may be compared to signatures of an unknown liquid to determine whether the liquid contains milk at one of the various concentrations illustrated in FIGS. 10-13.

Figure 11:
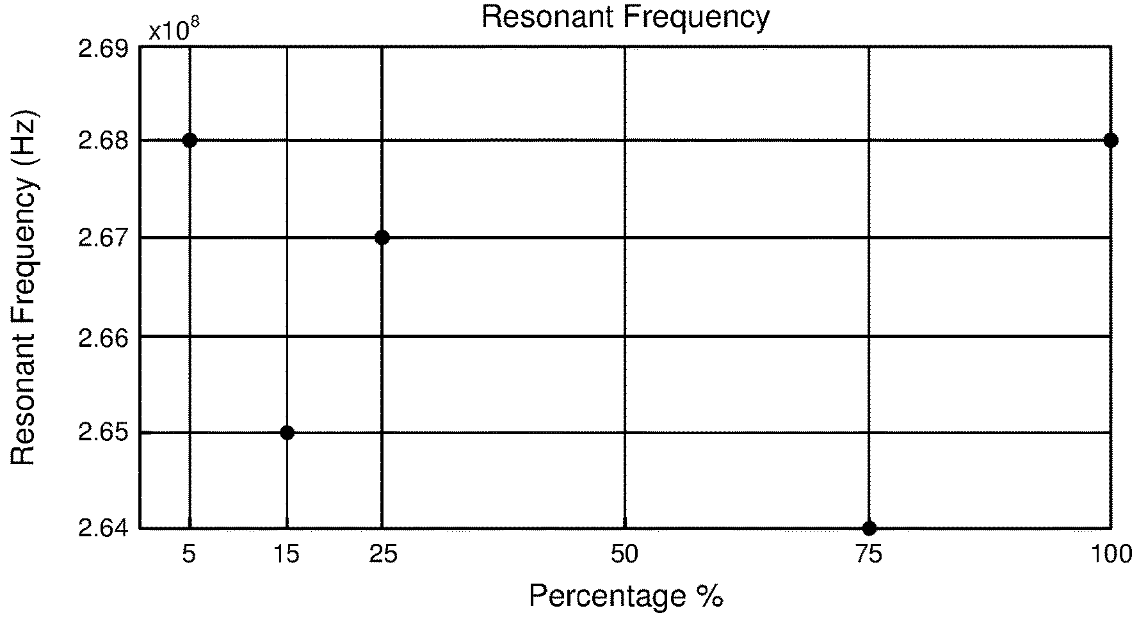
FIG. 11 is a diagram illustrating a plot of resonant frequencies observed during interrogation of liquids containing milk at different concentrations.

Referring to FIG. 11, a diagram illustrating a plot of resonant frequencies observed during interrogation of liquids containing milk at different concentrations is shown. In some embodiments, the information illustrated in FIG. 11 was generated based on information observed using system 100 of FIG. 1 (e.g., placing liquids containing different concentrations of milk within volume 114 of interrogator device 110, exciting coil(s) 112 at one or more frequencies by signal generator/receiver 138 of electronic device 130, and monitoring the behavior of coil(s) 112 during the excitement to determine one or more parameters). In some embodiments, the points plotted in FIG. 11 correspond to the different concentrations of milk illustrated with reference to FIG. 10. In some embodiments, the resonant frequencies illustrated in FIG. 11 may be utilized to generate signatures representative of the various concentrations of milk and the signatures generated based on the resonant frequency data illustrated in FIG. 11 may be stored (e.g., as part of known characteristic data 142 of FIG. 1) at a database (e.g., database 140 of FIG. 1). Once stored, these signatures may be compared to signatures of an unknown liquid to determine whether the liquid contains milk at one of the various concentrations illustrated in FIGS. 10-13.

Figure 12:
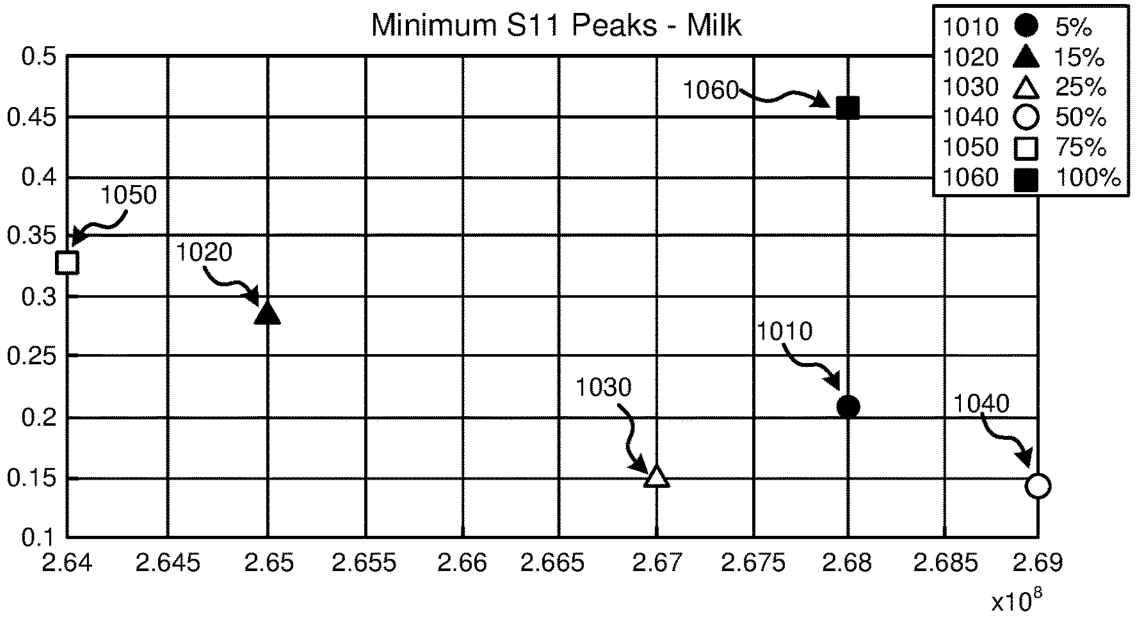
FIG. 12 is a diagram illustrating a plot of the minimum |S11| peaks observed during interrogation of liquids containing milk at different concentrations.

Referring to FIG. 12, a diagram illustrating a plot of the minimum |S11| peaks observed during interrogation of liquids containing milk at different concentrations is shown. In some embodiments, the information illustrated in FIG. 12 was generated based on information observed using system 100 of FIG. 1 (e.g., placing liquids containing different concentrations of milk within volume 114 of interrogator device 110, exciting coil(s) 112 at one or more frequencies by signal generator/receiver 138 of electronic device 130, and monitoring the behavior of coil(s) 112 during the excitement to determine one or more parameters). As illustrated in FIG. 12, a liquid containing an approximately 5% concentration of milk 1010 will exhibit a minimum |S11| peak having a magnitude of approximately 0.21 at a frequency of approximately 2.68 Hz, a liquid containing an approximately 15% concentration of milk 1020 will exhibit a minimum |S11| peak having a magnitude of approximately 0.28 at a frequency of approximately 2.65 Hz, a liquid containing an approximately 25% concentration of milk 1030 will exhibit a minimum |S11| peak having a magnitude of approximately 0.15 at a frequency of approximately 2.67 Hz, a liquid containing an approximately 50% concentration of milk 1040 will exhibit a minimum |S11| peak having a magnitude of approximately 0.14 at a frequency of approximately 2.69 Hz, a liquid containing an approximately 75% concentration of milk 1050 will exhibit a minimum |S11| peak having a magnitude of approximately 0.33 at a frequency of approximately 2.64 Hz, and a liquid containing an approximately 100% concentration of milk 1060 will exhibit a minimum |S11| peak having a magnitude of approximately 0.46 at a frequency of approximately 2.68 Hz. In some embodiments, the minimum |S11| peaks illustrated in FIG. 12 may be utilized to generate signatures representative of the various concentrations of milk and the signatures generated based on the resonant frequency data illustrated in FIG. 12 may be stored (e.g., as part of known characteristic data 142 of FIG. 1) at a database (e.g., database 140 of FIG. 1). Once stored, these signatures may be compared to signatures of an unknown liquid to determine whether the liquid contains milk at one of the various concentrations illustrated in FIGS. 10-13.

Figure 13:
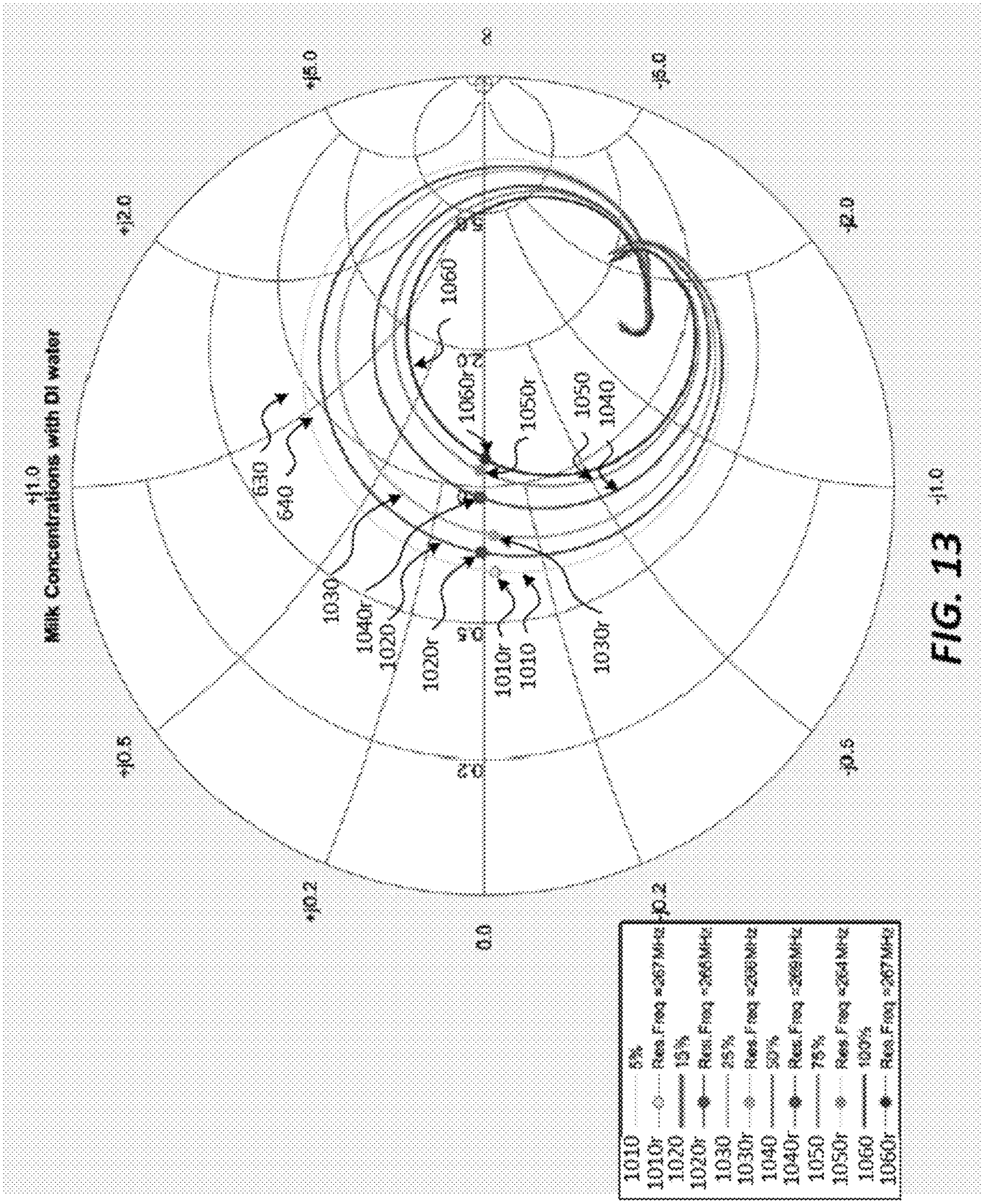
FIG. 13 is a diagram illustrating Smith charts generated based on observations during interrogation of liquids containing milk at different concentrations.

Referring to FIG. 13, a diagram illustrating Smith charts generated based on observations during interrogation of liquids containing milk at different concentrations is shown. In some embodiments, the information illustrated in FIG. 13 was generated based on information observed using system 100 of FIG. 1 (e.g., placing liquids containing different concentrations of milk within volume 114 of interrogator device 110, exciting coil(s) 112 at one or more frequencies by signal generator/receiver 138 of electronic device 130, and monitoring the behavior of coil(s) 112 during the excitement to determine one or more parameters). As illustrated in FIG. 13, each of the different concentrations of milk is uniquely represented on a Smith chart, and the resonant frequencies (e.g., the resonant frequencies illustrated in FIG. 11) are illustrated as circles having labels corresponding to their counterpart concentrations with an “r” appended to the end of the label (e.g., the circle 1010*r* represents the resonant frequency corresponding to a 5% concentration of milk 1010, etc.). In some embodiments, the various Smith charts for each concentration of milk illustrated in FIG. 13 may be utilized to generate signatures representative of the various concentrations of milk and the signatures generated based on the Smith charts illustrated in FIG. 13 may be stored (e.g., as part of known characteristic data 142 of FIG. 1) at a database (e.g., database 140 of FIG. 1). Once stored, these signatures may be compared to signatures of an unknown liquid to determine whether the liquid contains milk at one of the various concentrations illustrated in FIGS. 10-13. As shown in FIG. 13, Smith chart 1060 corresponding to a sample of pure milk can be visually distinguished from samples of milk that have been diluted. In some embodiments, when determining whether a liquid purported to be milk is analyzed, a Smith chart known to be generated from pure milk and a Smith chart of the sample purported be milk may be displayed at a display device, and an operator may be able to determine whether the sample is what it is purported to be simply by viewing the displayed Smith charts. In additional or alternative embodiments, a system, such as system 100 of FIG. 1, may compare the Smith charts and provide an output that indicates whether the sample is what it is purported to be.

Figure 14:
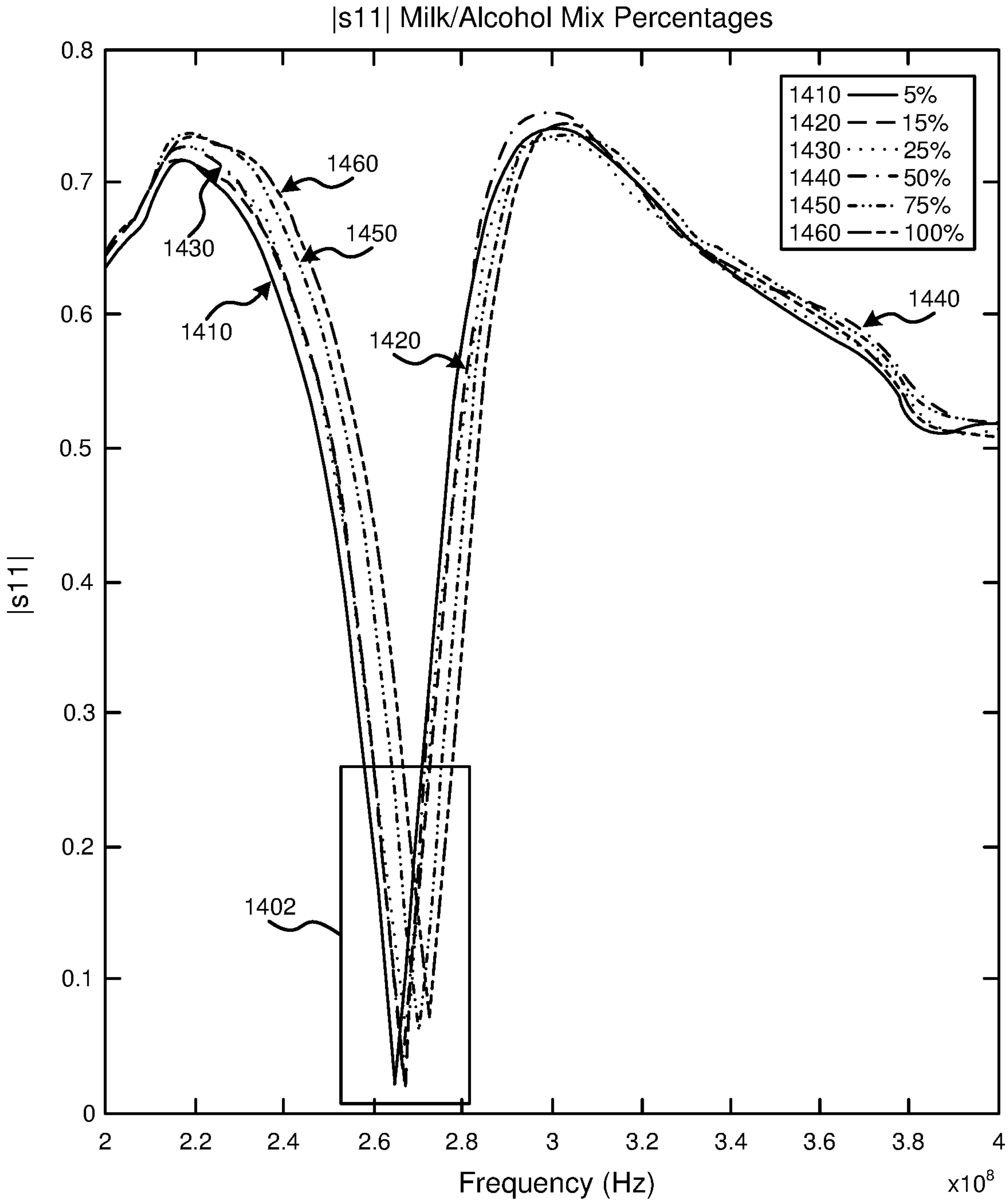
FIG. 14 is a chart illustrating characteristics observed during interrogation of liquids containing different milk/alcohol mixes according to embodiments of the present disclosure.

Referring to FIG. 14, a chart illustrating characteristics observed during interrogation of liquids containing different milk/alcohol mixes according to embodiments of the present disclosure is shown. In some embodiments, the information illustrated in FIG. 6 was observed using the system 100 of FIG. 14 and illustrates a plot of values representing the log magnitude for various observed values of an S-parameter (e.g., S11) during interrogation of a liquid by a device configured according to the embodiment illustrated in FIG. 1, as described in more detail below. For example, liquids containing different milk and alcohol percentages may be placed within volume 114 of interrogator device 110 and coil(s) 112 may be excited at one or more frequencies by signal generator/receiver 138 of electronic device 130. Signal generator/receiver 138 of electronic device 130 may monitor the behavior of coil(s) 112 during the excitement to determine one or more parameters, such as one or more S-parameters, representative of coil(s) 112 during the excitement, as described above with reference to FIGS. 1-4. In FIG. 14, observed |S11| values for liquids containing various milk and alcohol percentages are shown at a range of frequencies (e.g., from approximately 2 Hz to approximately 4 Hz). As shown in FIG. 14, the magnitude of the observed minimum |S11| peaks ranged from approximately 0.02 to approximately 0.08, as shown in box 1402, and occur approximately between 2.6 Hz and 2.8 Hz. As illustrated in FIG. 14, a liquid containing a 5% milk/alcohol mix is represented at 1410, a liquid containing a 15% milk/alcohol mix is represented at 1420, a liquid containing a 25% milk/alcohol mix is represented at 1430, a liquid containing a 50% milk/alcohol mix is represented at 1440, a liquid containing a 75% milk/alcohol mix is represented at 1450, and a liquid containing a 100% milk/alcohol mix is represented at 1460.

Figure 15:
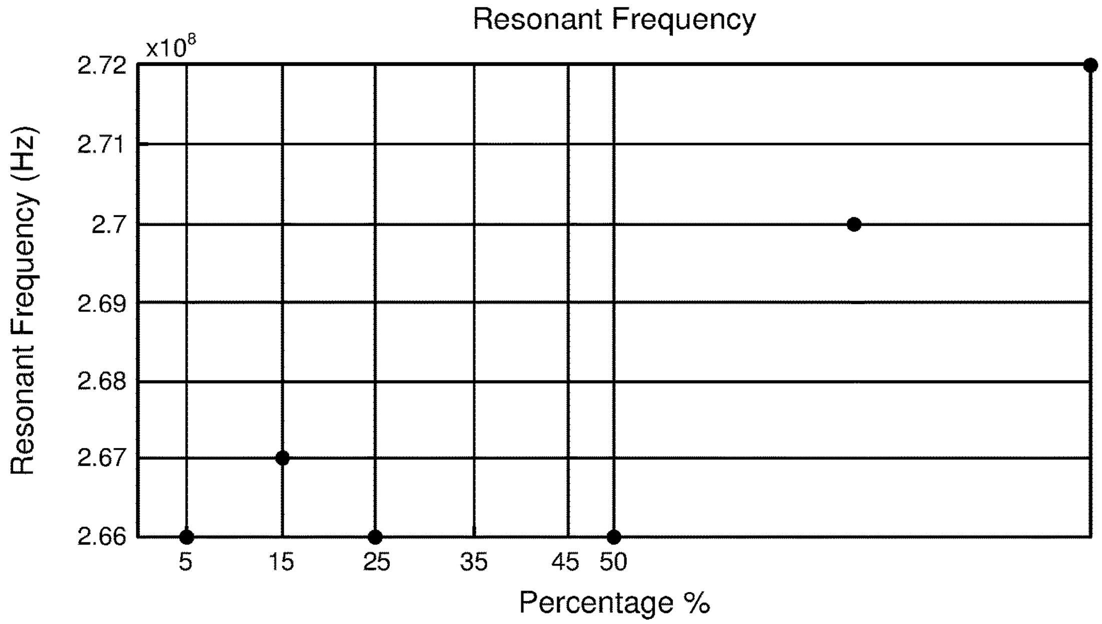
FIG. 15 is a diagram illustrating a plot of resonant frequencies observed during interrogation of liquids containing different milk/alcohol mixes according to embodiments.

Referring to FIG. 15, a diagram illustrating a plot of resonant frequencies observed during interrogation of liquids containing different milk/alcohol mixes according to embodiments is shown. In some embodiments, the information illustrated in FIG. 15 was generated based on information observed using system 100 of FIG. 1 (e.g., placing liquids containing different milk/alcohol mixes within volume 114 of interrogator device 110, exciting coil(s) 112 at one or more frequencies by signal generator/receiver 138 of electronic device 130, and monitoring the behavior of coil(s) 112 during the excitement to determine one or more parameters). In some embodiments, the points plotted in FIG. 15 correspond to, and represent the resonant frequencies of, the liquids of different milk/alcohol mixes illustrated with reference to FIG. 14. In some embodiments, the resonant frequencies illustrated in FIG. 15 may be utilized to generate signatures representative of the various liquids containing the different milk/alcohol mixes. These signatures may then be compared against signatures of liquids containing known milk/alcohol mixes to identify the components of the liquids under observation (e.g., identify liquids containing particular milk/alcohol mixes).

Figure 16:
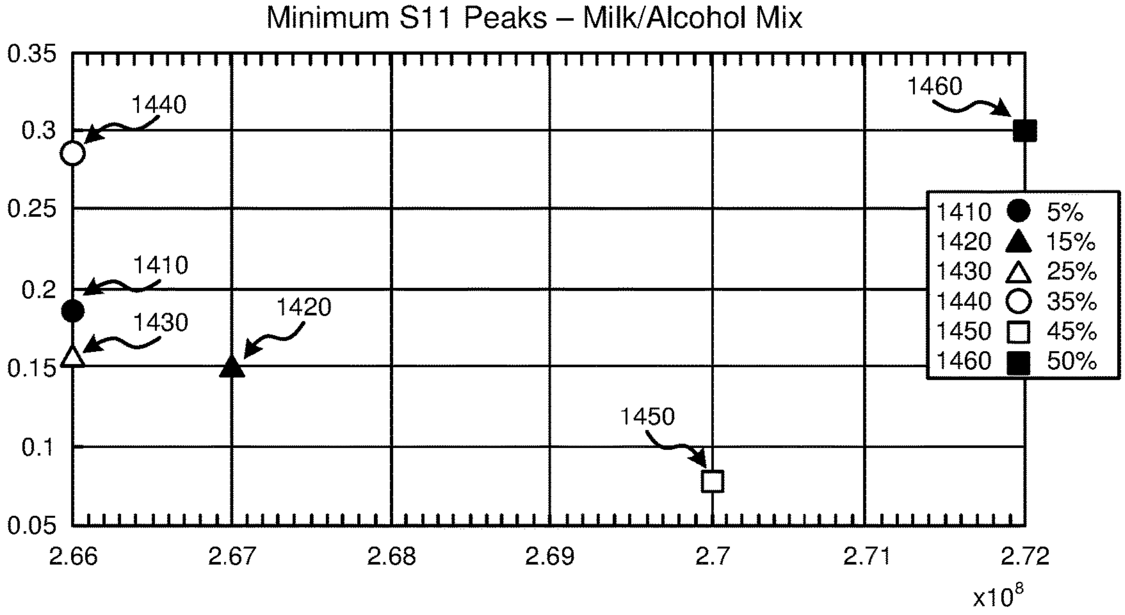
FIG. 16 is a diagram illustrating a plot of the minimum |S11| peaks observed during interrogation of liquids containing different milk/alcohol mixes.

Referring to FIG. 16, a diagram illustrating a plot of the minimum |S11| peaks observed during interrogation of liquids containing different milk/alcohol mixes is shown. In some embodiments, the information illustrated in FIG. 16 was generated based on information observed using system 100 of FIG. 1 (e.g., placing liquids containing different milk/alcohol mixes within volume 114 of interrogator device 110, exciting coil(s) 112 at one or more frequencies by signal generator/receiver 138 of electronic device 130, and monitoring the behavior of coil(s) 112 during the excitement to determine one or more parameters). As illustrated in FIG. 16, a liquid containing an approximately 5% concentration of milk/alcohol mix 1410 will exhibit a minimum |S11| peak having a magnitude of approximately 0.18 at a frequency of approximately 2.66 Hz, a liquid containing an approximately 15% concentration of milk/alcohol mix 1420 will exhibit a minimum |S11| peak having a magnitude of approximately 0.15 at a frequency of approximately 2.67 Hz, a liquid containing an approximately 25% concentration of milk/alcohol mix 1430 will exhibit a minimum |S11| peak having a magnitude of approximately 0.16 at a frequency of approximately 2.66 Hz, a liquid containing an approximately 50% concentration of milk/alcohol mix 1050 will exhibit a minimum |S11| peak having a magnitude of approximately 0.14 at a frequency of approximately 2.69 Hz, a liquid containing an approximately 75% concentration of milk 1050 will exhibit a minimum |S11| peak having a magnitude of approximately 0.33 at a frequency of approximately 2.64 Hz, and a liquid containing an approximately 100% concentration of milk 1060 will exhibit a minimum |S11| peak having a magnitude of approximately 0.46 at a frequency of approximately 2.68 Hz. In some embodiments, the minimum |S11| peaks illustrated in FIG. 16 may be utilized to generate signatures representative of the various milk/alcohol mixes and the signatures may be stored (e.g., as part of known characteristic data 142 of FIG. 1) at a database (e.g., database 140 of FIG. 1). Once stored, these signatures may be compared to signatures of an unknown liquid to determine whether the liquid contains a milk/alcohol mixture corresponding to one of the various milk/alcohol mixes illustrated in FIGS. 14-17.

Figure 17:
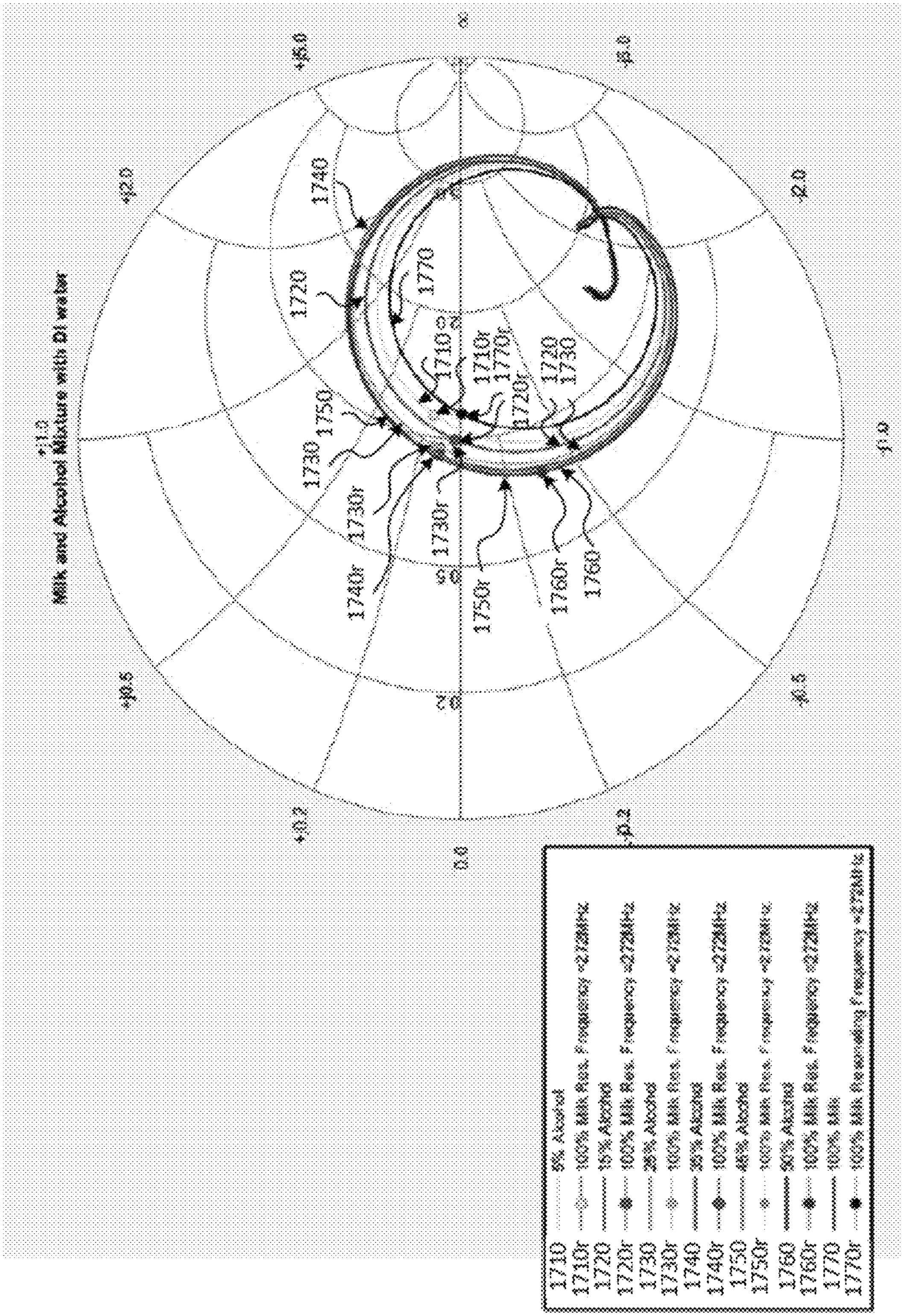
FIG. 17 is a diagram illustrating Smith charts generated based on observations during interrogation of liquids containing different milk/alcohol mixes.

Referring to FIG. 17, a diagram illustrating Smith charts generated based on observations during interrogation of liquids containing different milk/alcohol mixes is shown. In some embodiments, the information illustrated in FIG. 17 was generated based on information observed using system 100 of FIG. 1 (e.g., placing liquids containing different milk/alcohol mixes within volume 114 of interrogator device 110, exciting coil(s) 112 at one or more frequencies by signal generator/receiver 138 of electronic device 130, and monitoring the behavior of coil(s) 112 during the excitement to determine one or more parameters). As illustrated in FIG. 17, each of the different milk/alcohol mixes is uniquely represented on a Smith chart, the resonant frequencies (e.g., the resonant frequencies illustrated in FIG. 15 that are the frequencies when the S-parameters curves pass the horizontal axis) and the S-parameter locations at the original resonant frequency of 272 MHz, which are illustrated as circles having labels corresponding to their counterpart concentrations with an "r" appended to the end of the label (e.g., the circle 1410*r* represents the resonant frequency corresponding to a 5% milk/alcohol mixes 1410, etc.). As shown in FIGS. 15-17, the resonant frequency observed for milk shifts as the concentration of alcohol in the milk/alcohol mix increases. This can be observed by comparing the resonant frequency of milk illustrated by the curve 1760 of FIG. 17 (e.g., the resonating frequency of a milk in a mixture containing 50% milk and 50% alcohol) with the resonating frequency represented by the curve 1770 (e.g., the resonating frequency of a 100% concentration of milk) of FIG. 17. Comparing the locations of the circle 1770*r* (e.g., the resonating frequency of a milk in a mixture containing 100% milk) with the locations of the same frequency of 272 MHz on the Smith Chart may be used to identify the liquid content. In some embodiments, the various Smith Charts for each milk/alcohol mix illustrated in FIG. 17 may be utilized to generate signatures representative of the various milk/alcohol mixes and the signatures generated based on the shape of the Smith Chart curves illustrated in FIG. 17 may be stored (e.g., as part of known characteristic data 142 of FIG. 1) at a database (e.g., database 140 of FIG. 1). Once stored, these signatures may be compared to signatures of an unknown liquid to determine whether the liquid contains a milk/alcohol mix corresponding to one of the mixes illustrated with reference to FIGS. 14-17.

Figure 18A:
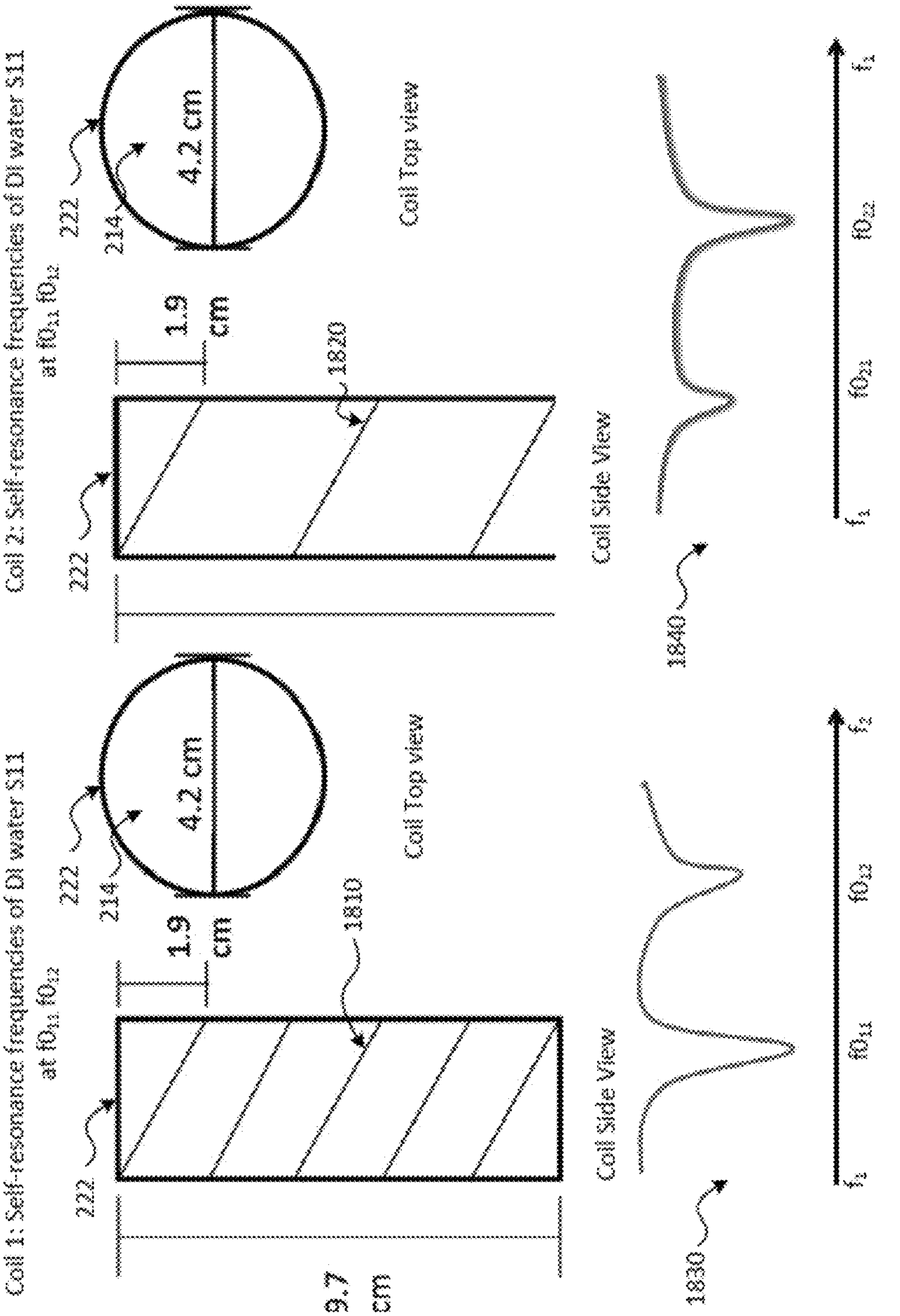
FIG. 18A is a diagram illustrating aspects of an embodiment of an interrogator comprising a plurality of coils according to the present disclosure.
Figure 21:
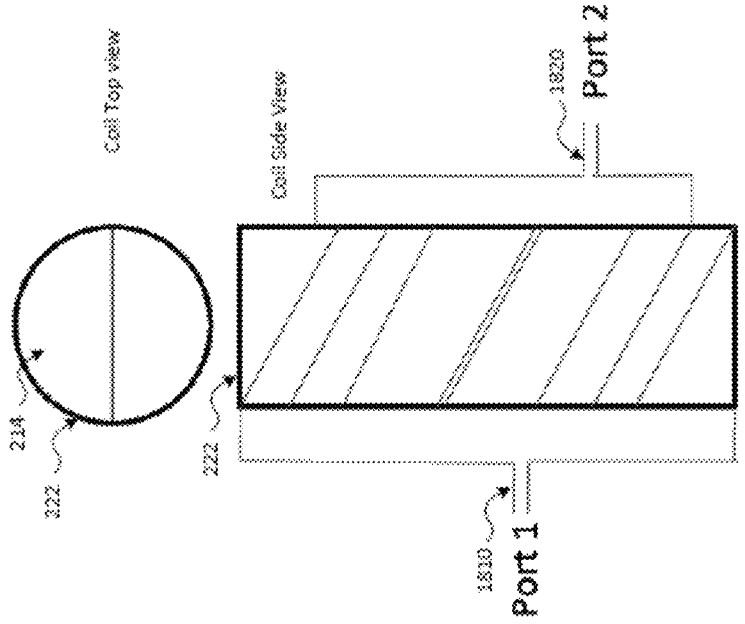
FIG. 21 is a diagram illustrating an embodiment of an interrogator device having a body surrounded by 2 coils.

Referring to FIG. 18A, a diagram illustrating aspects of an embodiment of the present sample-interrogators comprising a plurality of coils according to the present disclosure is shown. In FIG. 18A, body 222 of FIG. 2 is shown, and, as described above with reference to FIGS. 1 and 2, the body 222 may define an interior channel or opening that provides a volume, such as volume 214 of FIG. 2. In the particular embodiment illustrated in FIG. 18A, body 222 has a height of approximately 9.7 centimeters (cm) and a diameter of approximately 4.2 cm. A first coil 1810 and a second coil 1820 may be provided, and each of the coils 1810, 1820 may surround the body 222. For example, and referring briefly to FIG. 21, a diagram illustrating an embodiment of an interrogator device having a body surrounded by two coils is shown. As illustrated in FIG. 21, the different coils may comprise a different number of wraps (e.g., may wrap around body 222 a different number of times), and may have a different spacing between wraps. It is noted however, that the particular configuration of coils 1810, 1820 shown in FIG. 21 is provided for purposes of illustration, rather than by way of limitation, and in some embodiments, more than two coils may be used, a plurality of coils with the same number of wraps with the same or different spacing between two or more of the plurality of coils may be used, or other configurations depending on a particular purpose or configuration of the interrogation device. Thus, embodiments of the present disclosure are not to be limited to a particular number of coils, a particular number of wraps, or a particular spacing between wraps.

Additionally, as shown in FIG. 21, each of the coils may provide a port. The port may provide an I/O interface for coupling the coils to an interrogation device, such as electronic device 130 of FIG. 1 which includes the one or more signal generators/receivers 138. Signal generator(s)/receiver(s) 138 may provide a respective source signal to each of coils 1810, 1820 via the respective ports to excite the coils, and may measure one or more parameters characteristic of the behavior of coils 1810, 1820 in response to the exciting of the coils, such as scattering parameters with representative reflection coefficients (e.g., S11 and S22 parameters), and transmission coefficients (e.g., S12 and S21), and resonance frequencies, the curve shapes and locations on the Smith Chart, or a combination thereof for each of coils 1810, 1820. These parameters may be used to generate signatures that may be stored in a database (e.g., database 140 of FIG. 1) as either sample data 144 (e.g., when the liquid within volume 214 is an unknown liquid to be identified) or known characteristics data 142 (e.g., when liquid within volume 214 is a known liquid or mixture of liquids).

Figure 18B:
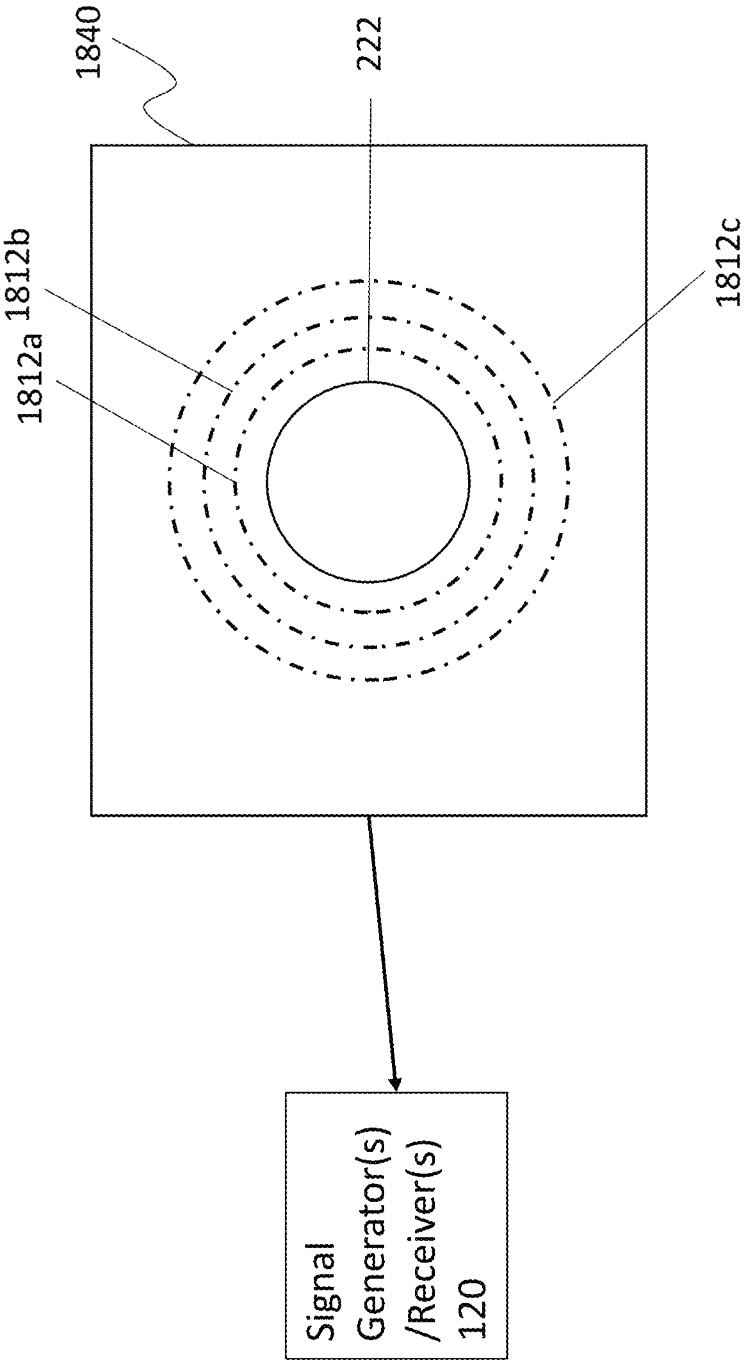
FIG. 18B is a diagram illustrating aspects of an embodiment of an interrogator comprising a plurality of coils according to the present disclosure.

In a similar embodiments to the interrogator having a plurality of coils as shown in FIG. 18, an alternative embodiment may include a plurality of coils such that each coil is positioned at a different lateral distance from a body 222. Alternatively, one or more single strip antenna(e) may be used in combination or as a replacement for the coils 112. Referring to FIG. 3D, the plurality of coils (e.g., 1812*a*, 1812*b*, and 1812*c*) may have a different radius then the rest of the plurality of coils. The plurality of coils may be arranged such that the plurality of coils each encircle the body 222, while, in alternate embodiments, the body 222 may encircle the plurality of coils. The plurality of coils may be arranged such that the coil with the largest radius will encircle the other coils in the plurality of coils. Different arrangements may be utilized by increasing or decreasing the number of coils in the plurality of coils, along with the distance from the plurality of coils to the body. As described in more detail above, signal generator(s)/receiver(s) may provide a signal to excite the coils, and may measure one or more parameters of the coils to generate signatures that can be stored in a database. It is noted however, that the particular configuration of coils 1812*a*, 1812*b*, and 1812*c* shown in FIG. 18B is provided for purposes of illustration, rather than by way of limitation, and in some embodiments, more or less than three coils may be used, a plurality of coils with the same or different spacing between the plurality of coils may be used, or other configurations depending on a particular purpose or configuration of the interrogation device. Thus, embodiments of the present disclosure are not to be limited to a particular number of coils or a particular spacing between coils. It is noted that in additional or alternative embodiments, a plurality of antenna(e) may be provided, and each of the plurality of antenna(e) may have a different radius and may be encircle the body in increasing distances relative to their radii. In other embodiments, the plurality of antenna(e) are encircled by the body.

Figure 19:
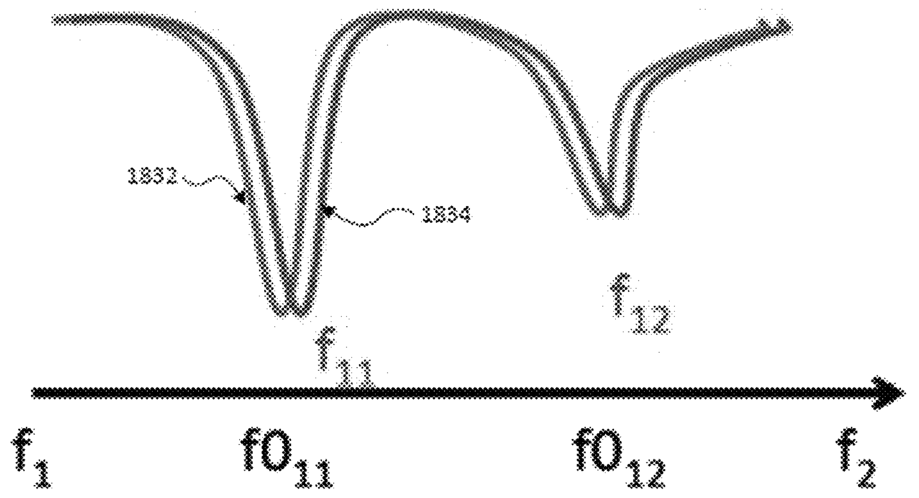
FIG. 19 is a diagram illustrating aspects of an embodiment for performing classification of a liquid using a signature generated according to embodiments.
Figure 20:
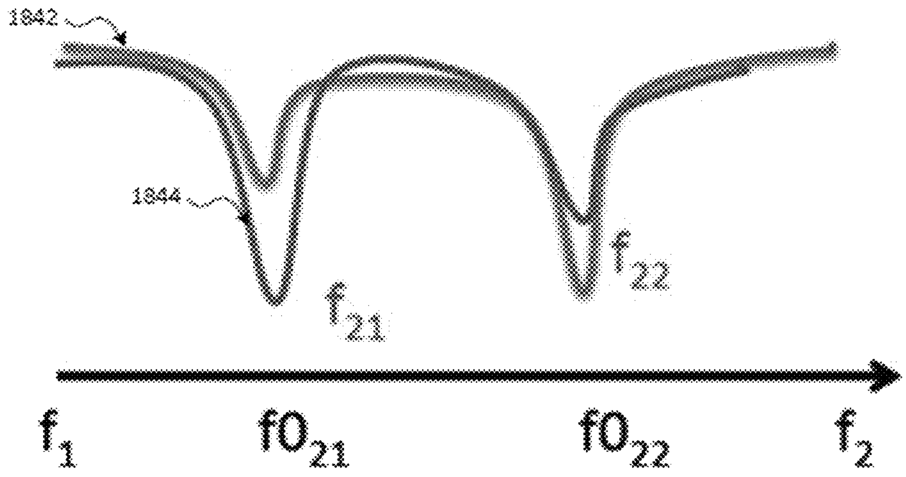
FIG. 20 is a diagram illustrating additional aspects of an embodiment for performing classification of a liquid using a signature generated according to embodiments.

Additionally, as shown in FIG. 18B, a switch 1840 may be used to selectively activate one or more coils of the plurality of coils. For example, switch 1840 may selectively activate coil 1812*a* to generate a signature as described above. In another example, switch 1840 may selectively activate coils 1812*a*, and 1812*c* to generate a signature. The switch may be configures such that it can selectively activate and deactivate any coil in the plurality of coils to act individually or in combination with any other coil(s) in the plurality of coils. In some embodiments, not pictured, phase matching the plurality of coils may occur. In some embodiments a matching circuit may be coupled in series with the coil(s). The matching circuit may be used to match the impedance between two points of the interrogator device 100, such that power transfer is optimized to the coil(s) 112. Optimizing power transfer to the coils(s) 112 may increase the sensitivity of the signatures by generating more precise parameters. For example, a Pi matching circuit may be used to generate higher quality factors in resonance when identifying de-ionized water. The matching circuit may enhance sensitivity to other parameters used by the interrogator 100, as described in more detail below Referring back to FIG. 18A, as illustrated at 1830 and 1840, each of coils 1810 may have multiple resonant frequencies, shown at 1830 with respect to first coil 1810 and 1840 with respect to second coil 1820. As shown in FIG. 18A, first coil 1810 may have resonant frequencies at f011 and f012, as shown at 1830, and second coil 1820 may have resonant frequencies at f021 and f022, as shown at 1840 when the known material is deionized water. One or more signatures may be generated based on these observed parameters, and then those signatures may be used to identify an unknown liquid (e.g., determine whether the unknown liquid is deionized water). For example, and referring to FIGS. 19 and 20, when an unknown liquid is interrogated using the coil configuration illustrated in FIG. 18A, the first coils 1810 may have resonant frequencies 1834 and the second coil 1820 may have resonant frequencies of 1844. As shown in FIGS. 19 and 20, when the unknown liquid is interrogated, the resonant frequencies of the coil 1810 illustrated at 1834 may be shifted by f11 and f12 relative to those of 1832 (e.g., the resonant frequencies of the first coil 1810 as observed during interrogation of DI water), and the resonant frequencies of the coil 1820 illustrated at 1844 may be shifted by f21 and f22 relative to those of 1842 (e.g., the resonant frequencies of the second coil 1820 as observed during interrogation of DI water). In some embodiments, these frequency shifts and the corresponding magnitudes of the S-parameters at the resonant frequencies may be used to identify the unknown liquid by comparing this data to information stored in a database (e.g., the database 140 of FIG. 1). In some embodiments, the comparison of the frequency shifts and corresponding magnitudes of the S-parameters at the resonant frequencies may be performed using Smith Charts, as described below with reference to FIG. 22.

Figure 22:
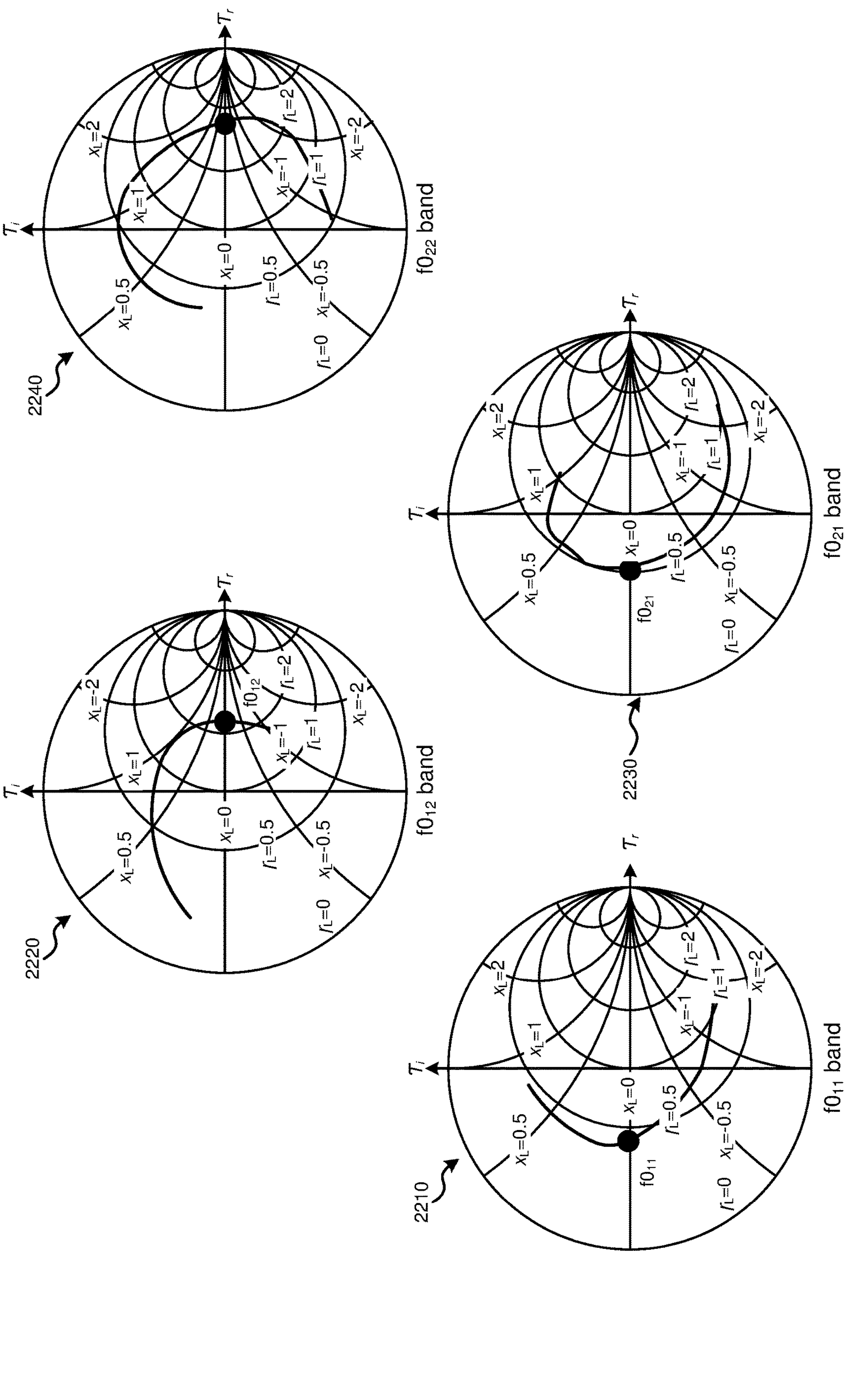
FIG. 22 is a diagram illustrating an embodiment of an additional technique for identifying an unknown liquid using Smith Charts and the related resonant frequencies according to the present disclosure.

Referring to FIG. 22, a diagram illustrating an embodiment of an additional technique for identifying an unknown liquid according to the present disclosure is shown. In some embodiments, the Smith Charts illustrates in FIG. 22 may be generated using an interrogation device configured according to the embodiments illustrated with reference to FIGS. 18A and 21 (e.g., an interrogation device comprising two coils, such as the coils 1810 and 1820 of FIGS. 18A and 21). In FIG. 22, a first Smith chart 2210, a second Smith chart 2220, a third Smith chart 2230, a fourth Smith chart 2240 are shown. First Smith chart 2210 may represent the resonant frequency observed at f011 during excitement of first coil 1810 and/or second coil 1820 of FIG. 18A, second Smith chart 2220 may represent the resonant frequency observed at f012 during excitement of first coil 1810 and/or second coil 1820 of FIG. 18A, third Smith chart 2230 may represent the resonant frequency observed at f021 during excitement of first coil 1810 and/or second coil 1820 of FIG. 18A, and fourth Smith chart 2240 may represent the resonant frequency observed at f022 during excitement of first coil 1810 second coil 1820 of FIG. 18A. In some embodiments, f012 may depend on or be effected by excitation of coil 2, and/or f021 may depend on or be effected by excitation of coil 1. In some embodiments, Smith charts associated with the resonant frequencies observed during interrogation of an unknown liquid may be compared to the Smith charts illustrated in FIG. 22 to identify the unknown liquid. If the shapes and locations of the curves in the Smith Charts and/or resonant frequencies match to within a threshold tolerance, the unknown liquid may be identified as the known liquid used to produce Smith charts 2210-2240. If the shapes and locations of the curves in the Smith charts and/or resonant frequencies generated for the unknown liquid do not match Smith charts 2210-2240 to within the threshold tolerance, the Smith charts generated for the unknown liquid may be compared to Smith charts generated for additional known liquids to identify the unknown liquid. Embodiments utilizing a plurality of coils, such as the embodiments described with reference to FIGS. 18-22, may provide improved accuracy when identifying unknown liquids. For example, using two coils may enable more features or parameters to be observed during interrogation of the liquid, providing more points of comparison for signature identification and matching purposes.

Figure 23:
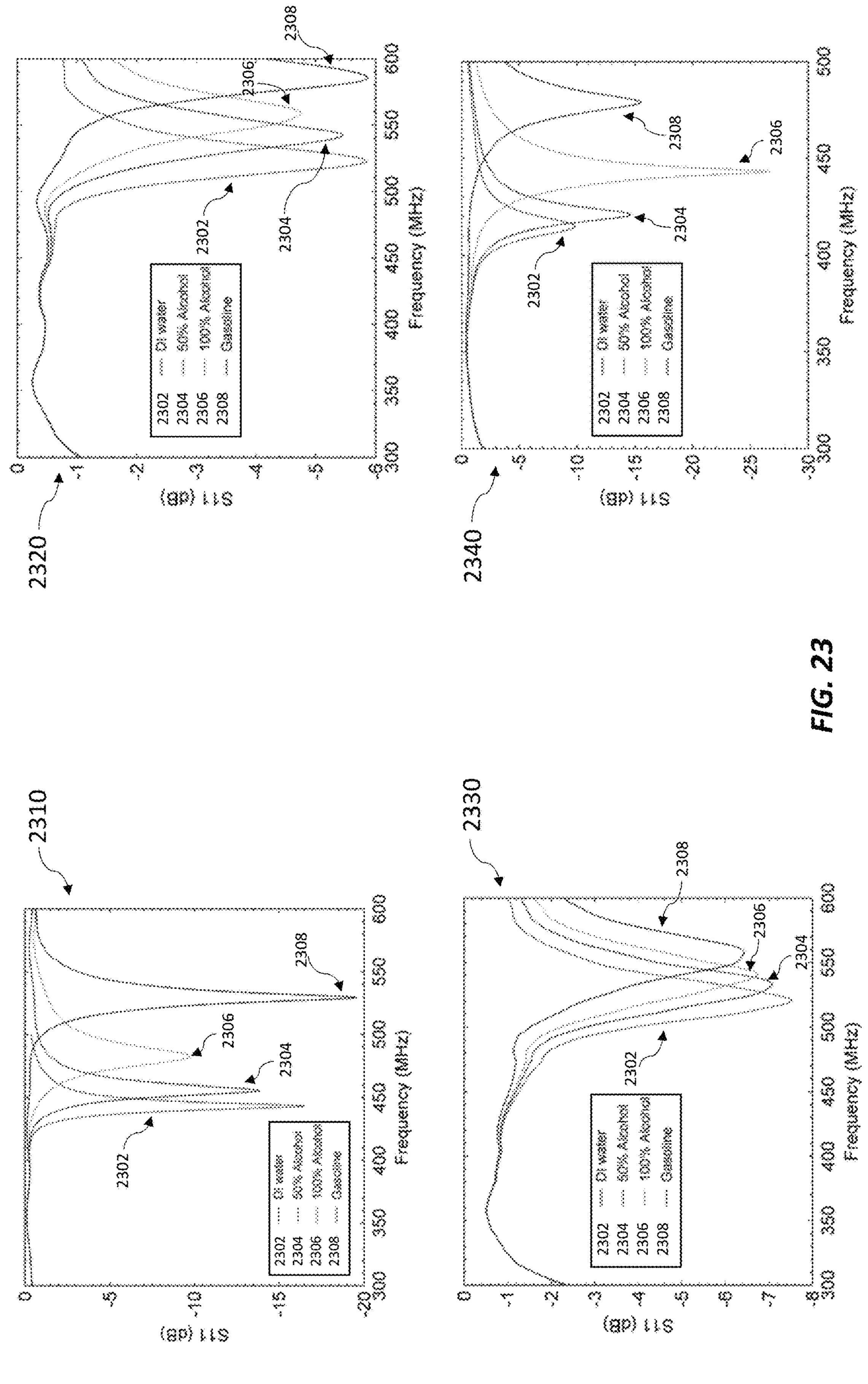
FIG. 23 is a diagram illustrating an embodiment of an additional technique for identifying an unknown liquid using a different arrangements of the coils according to the present disclosure
Figure 24:
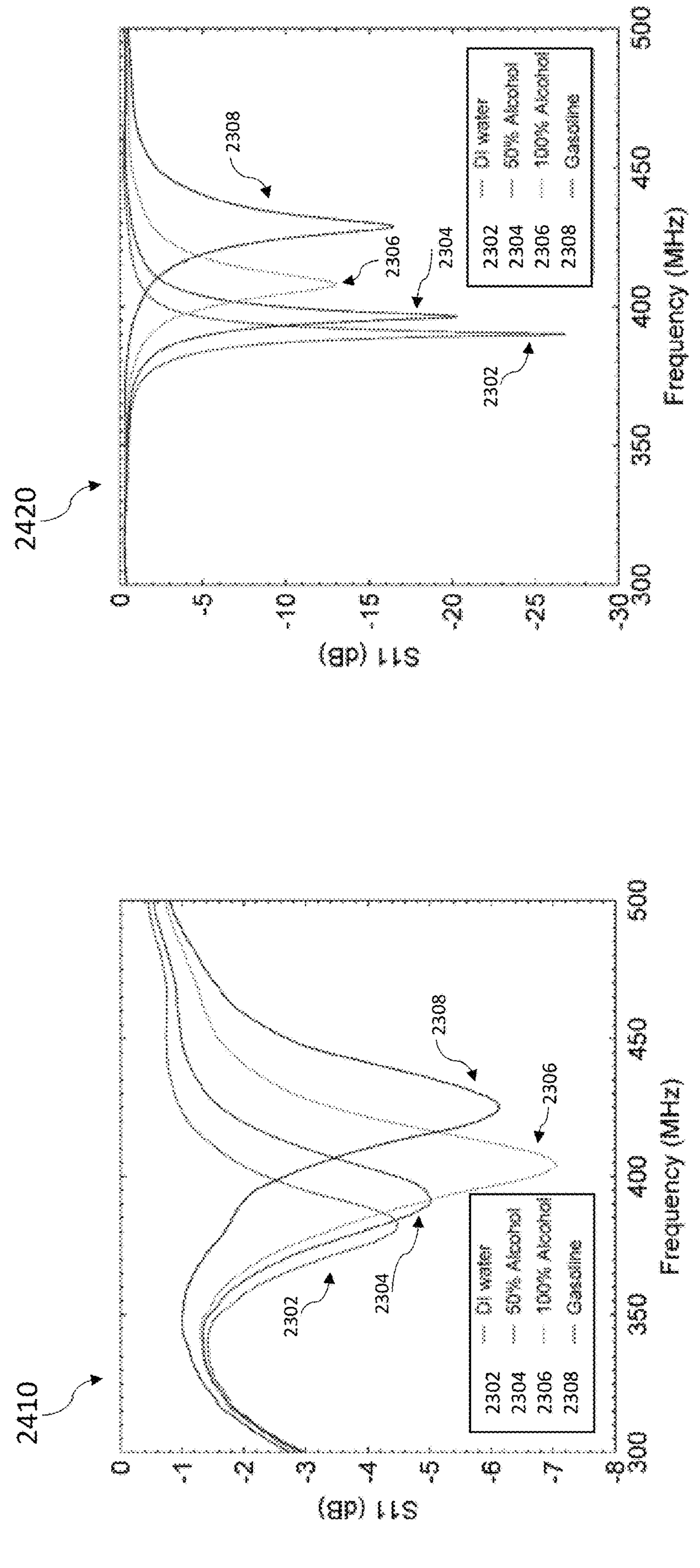
FIG. 24 is a diagram illustrating an embodiment of an additional technique for identifying an unknown liquid using a plurality of coils according to the present disclosure

Referring to FIG. 23, charts illustrating characteristics observed during interrogation of a material using coil(s) according to the present disclosure are shown. In some embodiments, the charts illustrated in FIG. 23 may be generated using an interrogation device configured according to the embodiment illustrated in FIG. 18B (e.g., an interrogation devices having three coils each encircling the body and a switch configured to selectively activate the coil(s)). In FIG. 23, a first chart 2310, a second chart 2320, a third chart 2330, and a fourth chart 2340 are shown, where each chart represents a different arrangement of coils in the system. The charts may display the a plot of various observed parameter values (e.g., values of an S-parameter—S11) during interrogation of a liquid across a range of frequencies (e.g., from approximately 300 MHz to 600 MHz). First chart 2310 may represent the S11 parameters observed during interrogation of a liquid at an arrangement using the coil 1812*a* of FIG. 18B. Second chart 2320 may represent the S11 parameters observed during interrogation of a liquid at an arrangement using the coil 1812*b* of FIG. 18B. Third chart 2330 may represent the S11 parameters observed during interrogation of a liquid at an arrangement using the coil 1812*c* of FIG. 18B. Forth chart 2340 may represent the S11 parameters observed during interrogation of a liquid at an arrangement using coil 1812*b* and 1812*c* of FIG. 18B. As described above, parameters may be observed at one or more frequencies during interrogation. In some embodiments the use of switch 1840, of FIG. 18B, may allow generation of multiple charts possible without removal or reconfiguration of the interrogator. The interrogation may be performed for several liquids using each arrangement of the interrogator. For example, liquids containing different alcohol percentages may be placed within the interrogator device and the measured parameters of each liquid may be charted for each arrangement. More specifically, DI water 2302, may be plotted with several other liquids containing alcohol (50% alcohol 2304, 100% alcohol 2306, and gasoline 2308). As FIG. 23 shows, the resonant frequencies for each liquid can be distinguished by the interrogator using the methods described above for each arrangement 2310, 2320, 2330, and 2340. In other embodiments, characteristics observed during interrogation may also be configured to display Smith charts Referring to FIG. 24, charts illustrating characteristics observed during interrogation of a material using a plurality of coils according to the present disclosure are shown. In some embodiments the charts illustrated in FIG. 24 may be generated using an interrogation device configured according to the embodiment illustrated in FIG. 18B (e.g., an interrogation devices having three coils each encircling the body). In FIG. 24 a first chart 2410 and a second chart 2420 are shown. First chart 2410 may represent the S11 parameters observed during interrogation of a liquid at an arrangement using the plurality of coils 1812*a*, 1812*b* and 1812*c* of FIG. 18B. In some embodiments phase matching may be used to increase the sensitivity of the coils. Second chart 2420 may represent the S11 parameters observed during interrogation of a liquid at an arrangement using the plurality of coils 1812*a*, 1812*b* and 1812*c* of FIG. 18B using a phase matching device. For example, a pi matching circuit may be coupled in series with the sensor coils 1812*a*, 1812*b* and 1812*c* of FIG. 18B. Phase matching may be used to increase the accuracy of the signatures generated by the interrogator. For example, a matching circuit may improve the S11 parameters, thus improving the signatures, by generating high quality factors when using multiple coils.

Figure 25:
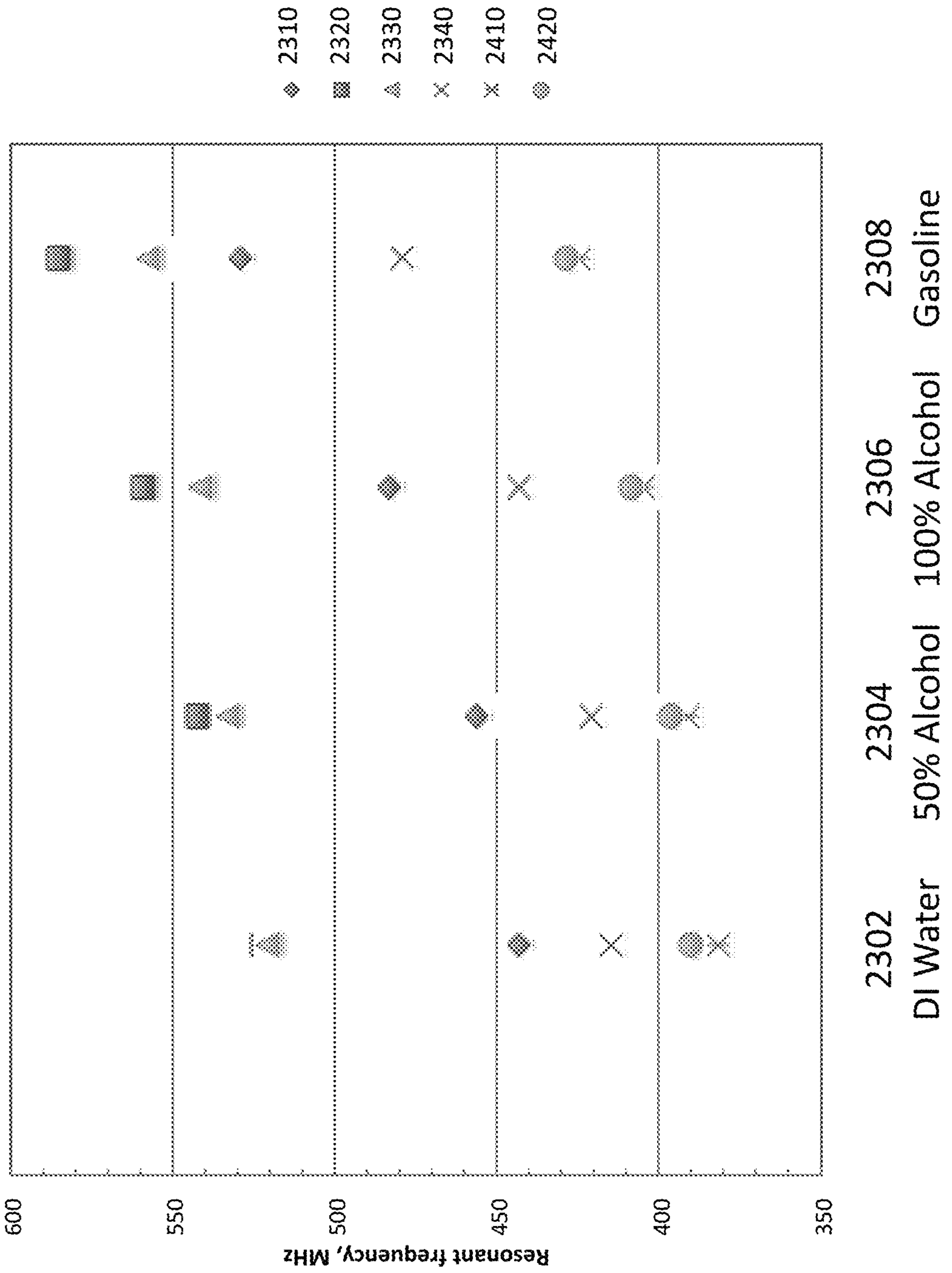
FIG. 25 is a chart of the observed parameters measured during various arrangements.

The different arrangements of the plurality of coils can generate multiple signatures and may enable a more accurate identification of the material undergoing interrogation, such as to rule out known signatures that do not exhibit similar behaviors at a particular arrangement used to interrogate an unknown material and/or to identify known signatures that exhibit similar behaviors at a particular arrangement used to interrogate an unknown material. For example, as illustrated by FIG. 25, six resonance frequencies can be generated from the six arrangements in accordance with the embodiment illustrated in FIG. 18. The new signatures may be added to the data base to increase the reliability of material identifications performed by the interrogator.

Figure 26:
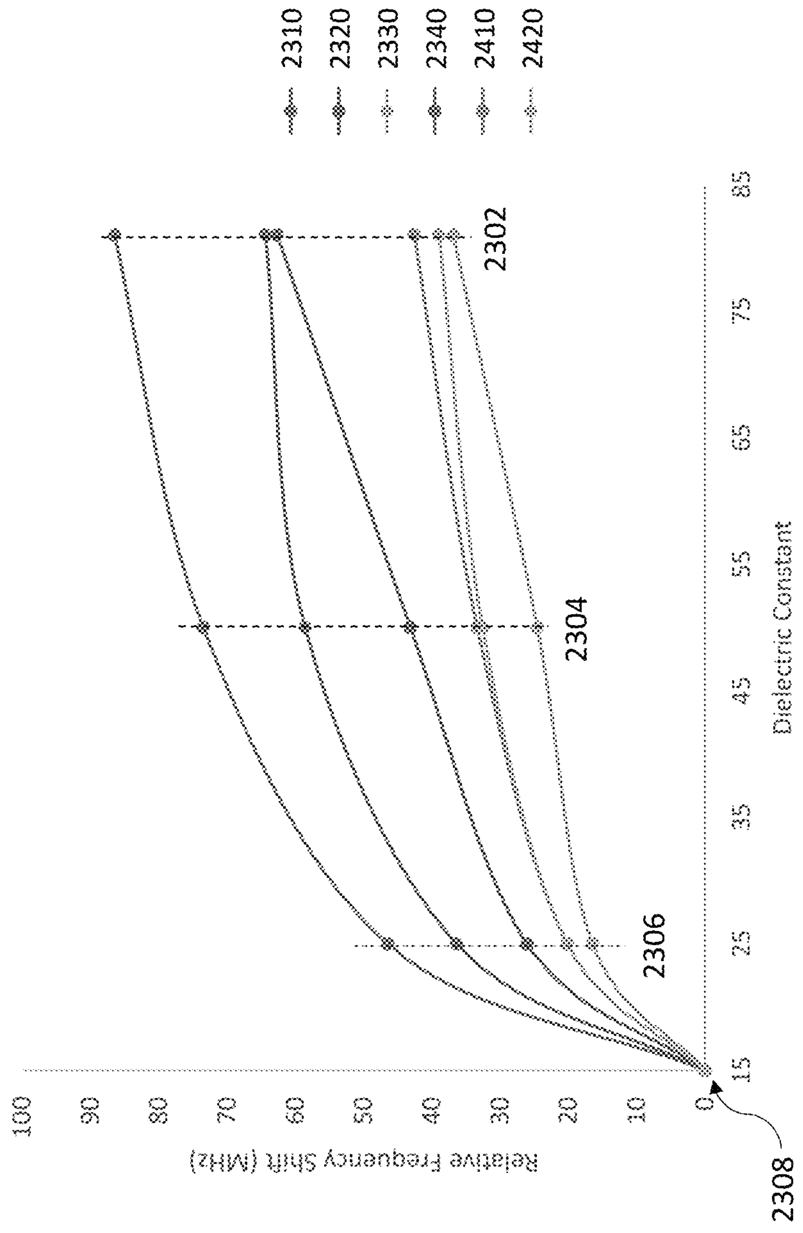
FIG. 26 is a chart showing the use of parameters of several liquids to cross check the observed parameters in order to generate more signatures.

Referring to FIG. 26, the parameters for a certain material determined at an arrangement may be used to cross check the parameters found in the material at other arrangements in order to generate more signatures. The parameters for a liquid measured in certain arrangements may be used as a reference point to generate signatures based on the observed parameters of other liquids in the same arrangement. For example, using the parameters found in FIG. 25, the resonant frequency of gasoline generated for all six arrangements (2310, 2320, 2330, 2340, 2410, 2420) may be set as a reference point and the relative frequency shifts of the other liquids (DI water 2302, 50% Alcohol 2304, and 100% Alcohol 2306) may be used as a signature for those arrangements.

Figure 27:
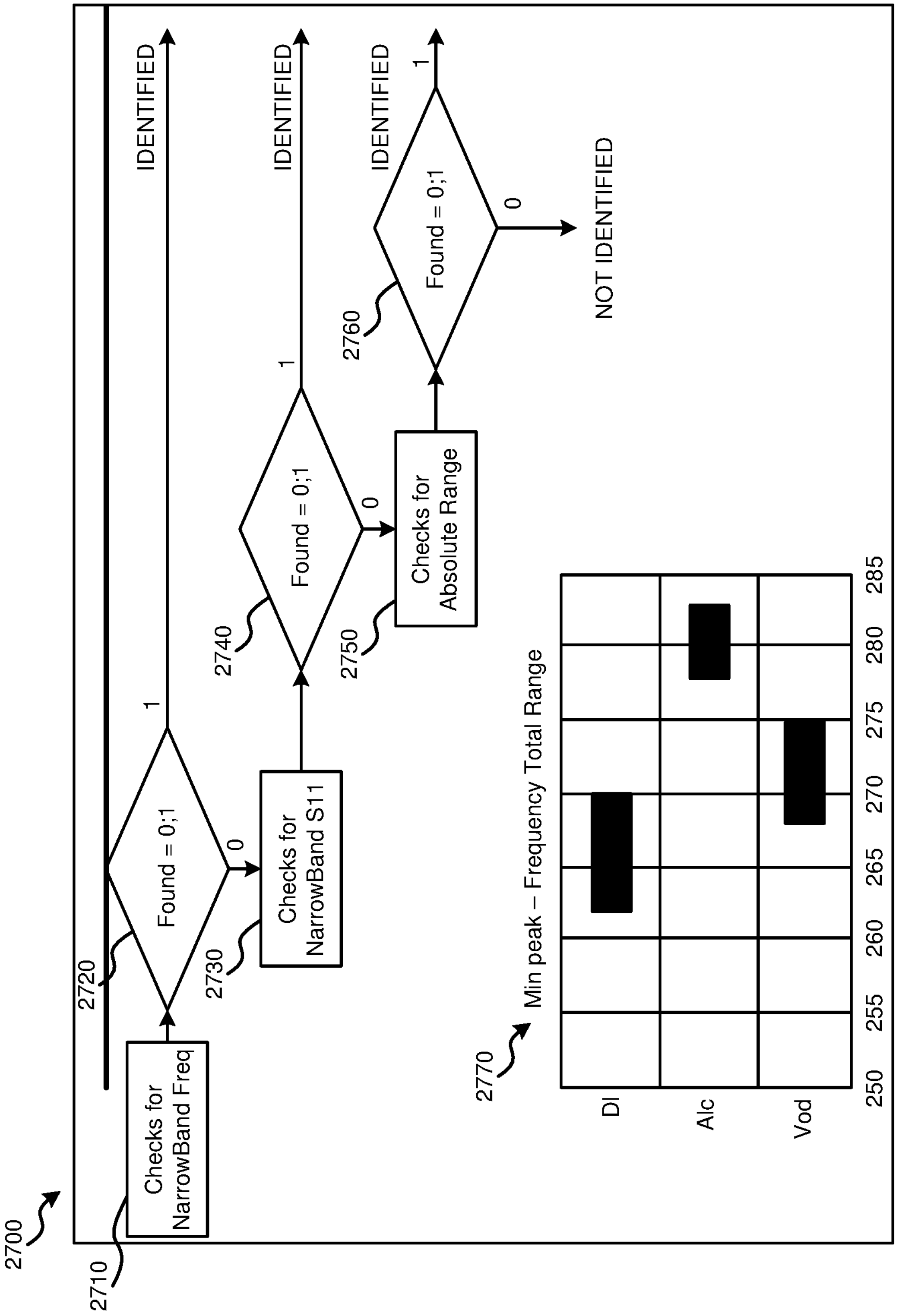
FIG. 27 is a flow diagram of exemplary method for identifying an unknown material in accordance with embodiments of the present disclosure.

Referring to FIG. 27, a flow diagram of exemplary method for identifying an unknown material in accordance with embodiments of the present disclosure is shown as a method 2700. In some embodiments, the method 2700 may correspond to step 440 of method 400 illustrated and described above with reference to FIG. 4. At step 2710, method 2700 includes checking for the presence of a minimum peak within a particular narrowband frequency range. At step 2720, a determination is made as to whether the minimum peak is present within a particular narrowband frequency range (e.g., a narrowband frequency range where a known material exhibits a minimum peak). If the minimum peak is present within the particular narrowband frequency range, the unknown material is identified as the material corresponding to the particular narrowband frequency range (e.g., the known material that exhibits a minimum peak at the particular narrowband frequency range), otherwise, the method 2700 continues to step 2730 where the presence of a minimum |S11| peak within a particular narrowband frequency range is checked. At step 2740, a determination is made as to whether the minimum |S11| peak is present within a particular narrowband frequency range (e.g., a narrowband frequency range where a known material exhibits a minimum |S11| peak). If the minimum |S11| peak is present within the particular narrowband frequency range, the unknown material is identified as the material corresponding to the particular narrowband frequency range (e.g., the known material that exhibits a minimum |S11| peak at the particular narrowband frequency range), otherwise the method 2700 continues to step 2750. At step 2750, the method 2700 checks an absolute frequency range for the presence of a minimum peak, and, at step 2760, if the minimum peak is found within a particular absolute range, the material is identified. Otherwise, the material cannot be identified (e.g., because the material does not exhibit characteristics of a known material or combination of materials). In FIG. 27, a minimum peak total frequency range 2770 for various materials is shown and includes a minimum peak total frequency range for DI, alcohol, and vodka.

Figure 28:
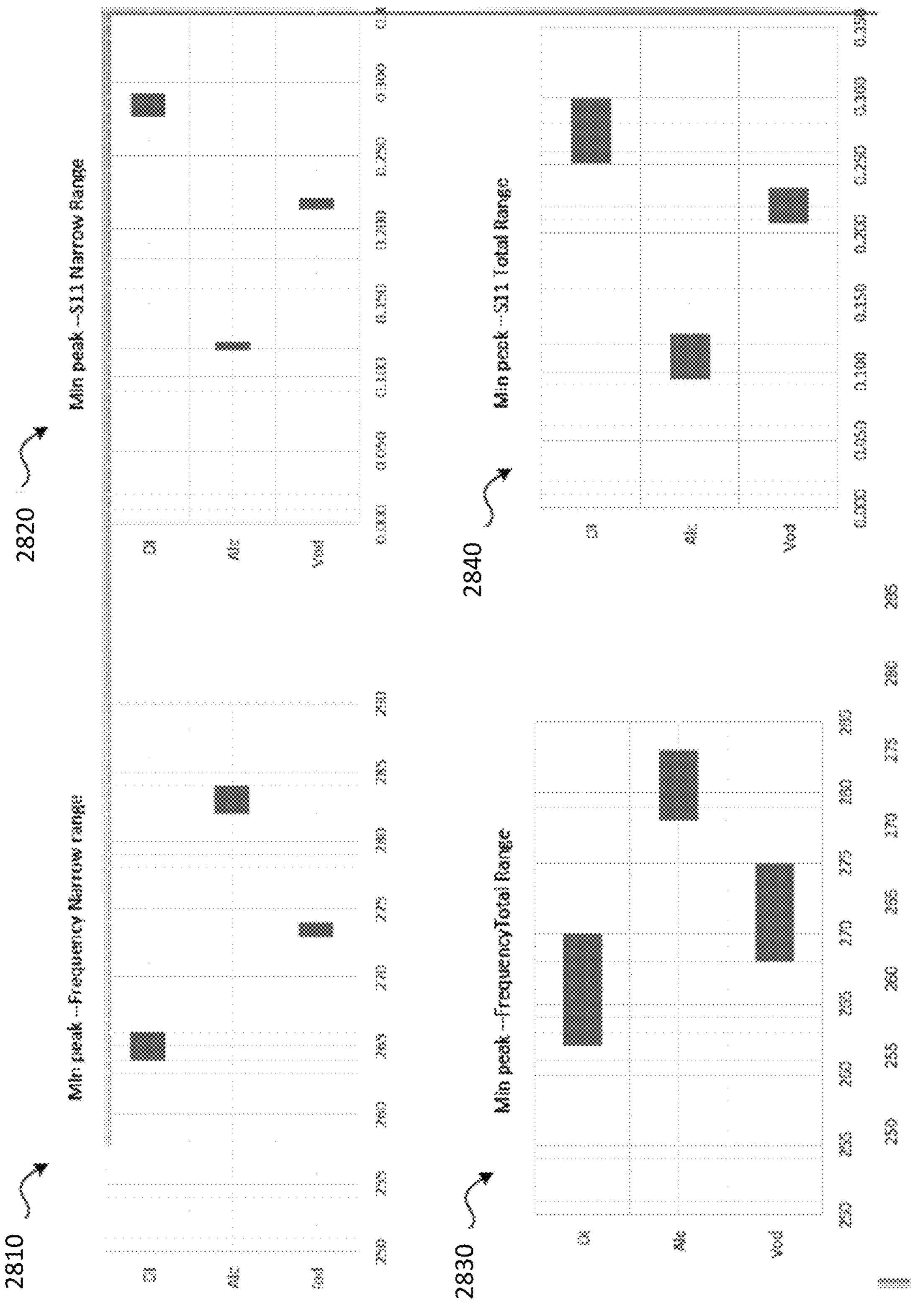
FIG. 28 is a diagram that illustrates additional aspects of frequency ranges that may be used to identify a material according to embodiments.

FIG. 28 is a diagram that illustrates additional aspects of frequency ranges that may be used to identify a material according to embodiments. For example, in FIG. 28, a minimum peak frequency narrow range 2810, a minimum |S11| peak narrow range 2820, a minimum peak frequency total range 2830, and a minimum |S11| peak total range 2840 are shown. Minimum peak frequency total range 2830 may be the same as minimum peak total frequency range 2770 illustrated in FIG. 27. Minimum peak frequency narrow range 2810 may be utilized in steps 2710 and 2720 of the method, minimum |S11| peak narrow range 2820 may be utilized in steps 2730 and 2740 of the method, and minimum |S11| peak total range 2840 may be utilized in steps 2750 and 2760 of the method. Thus, method 2700 may utilize the different frequency ranges to filter characteristics of an unknown material to identify the unknown material, such as to classify an unknown liquid as DI, alcohol, or vodka. For example, the various frequency ranges illustrated in FIG. 28 demonstrate that different liquids consistently exhibit certain properties when interrogated in accordance with embodiments of the present disclosure. This indicates that embodiments of the present disclosure are operable to identify liquids with a high degree of accuracy.

Figure 29:
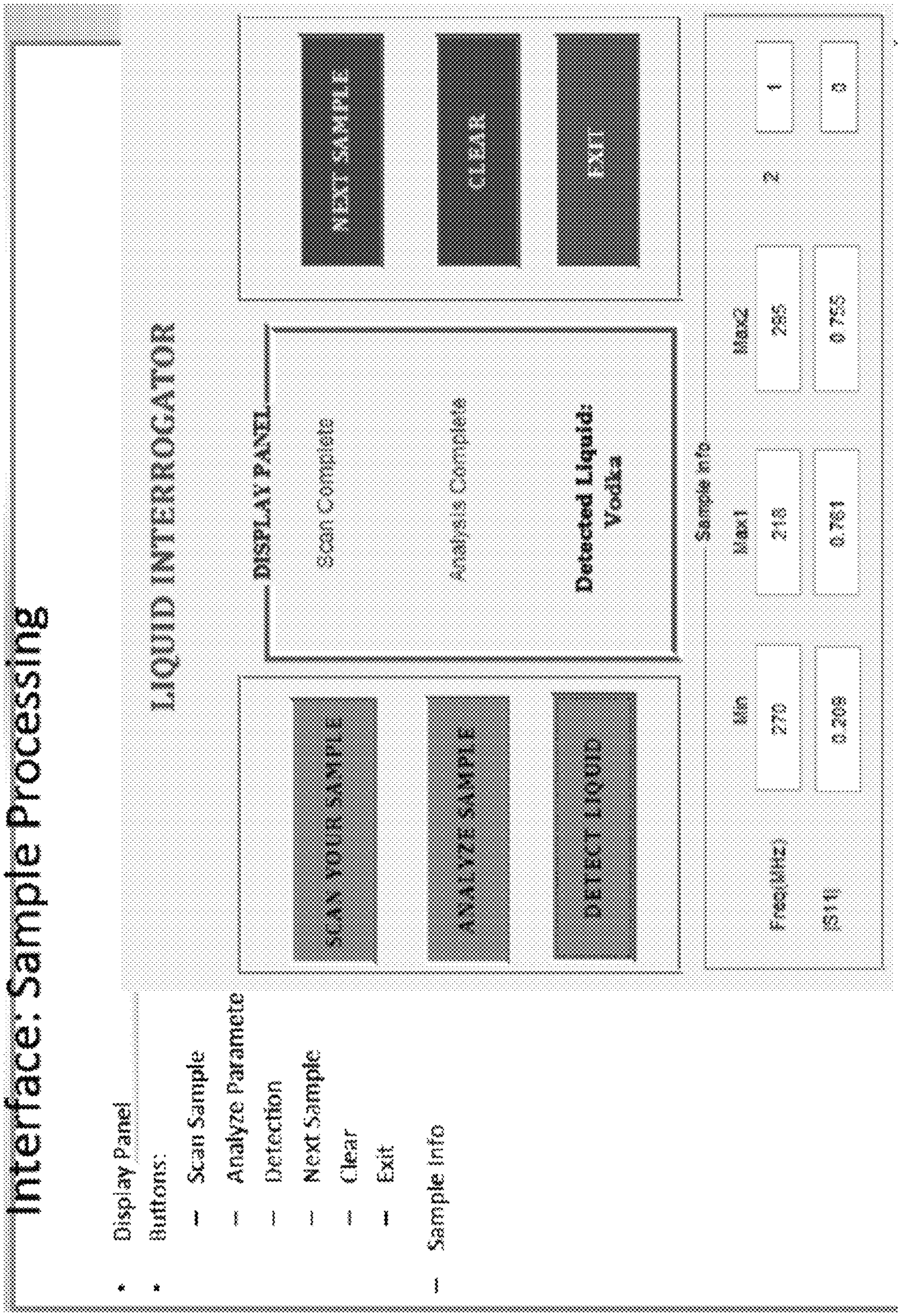
FIG. 29 is a diagram illustrating aspects of a graphical user interface (GUI) for configuring a system for interrogation of a sample of an unknown material.
Figure 30:
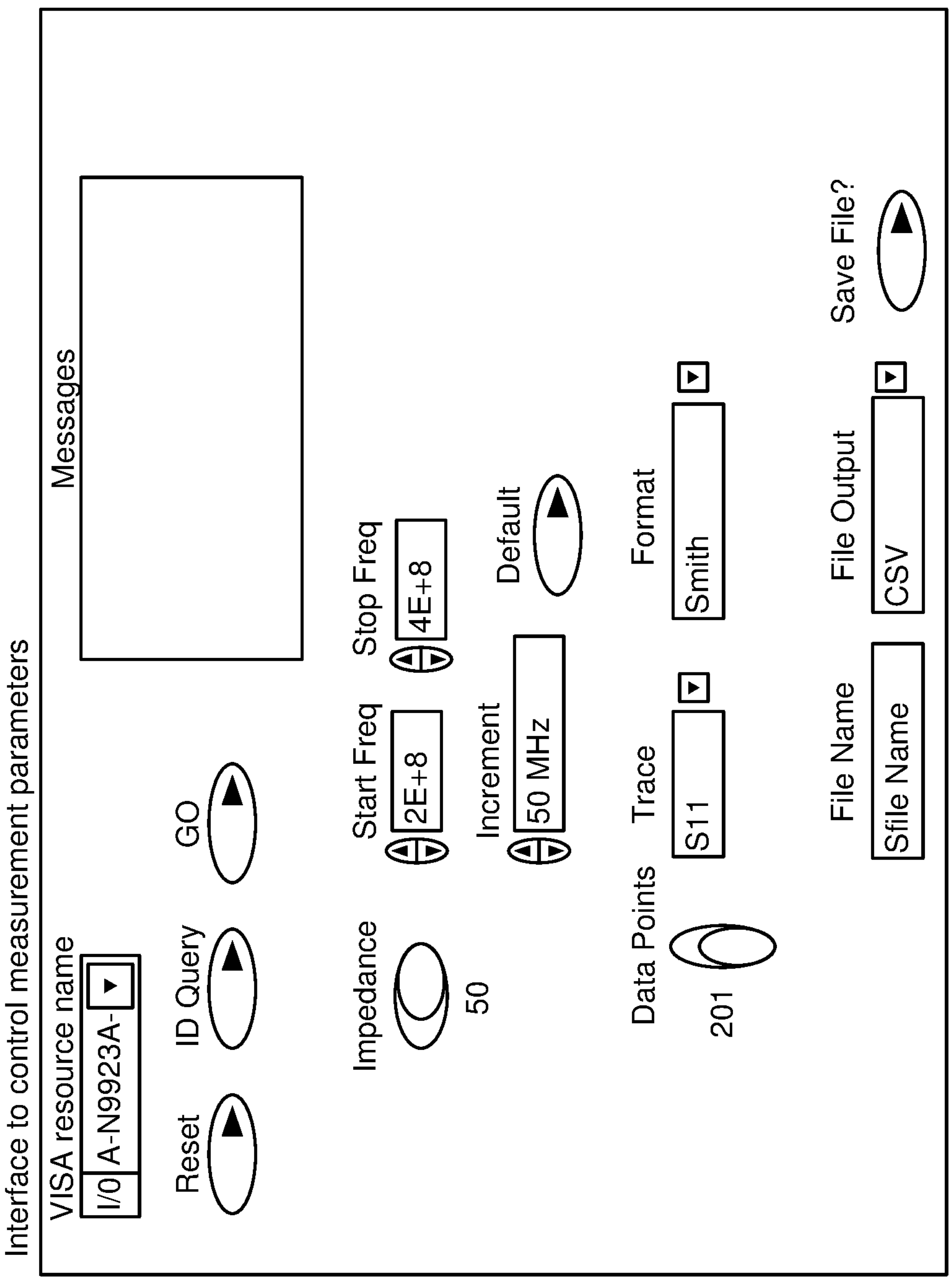
FIG. 30 is another diagram illustrating aspects of a graphical user interface (GUI) for configuring a system for interrogation of a sample of an unknown material.
Figure 32:
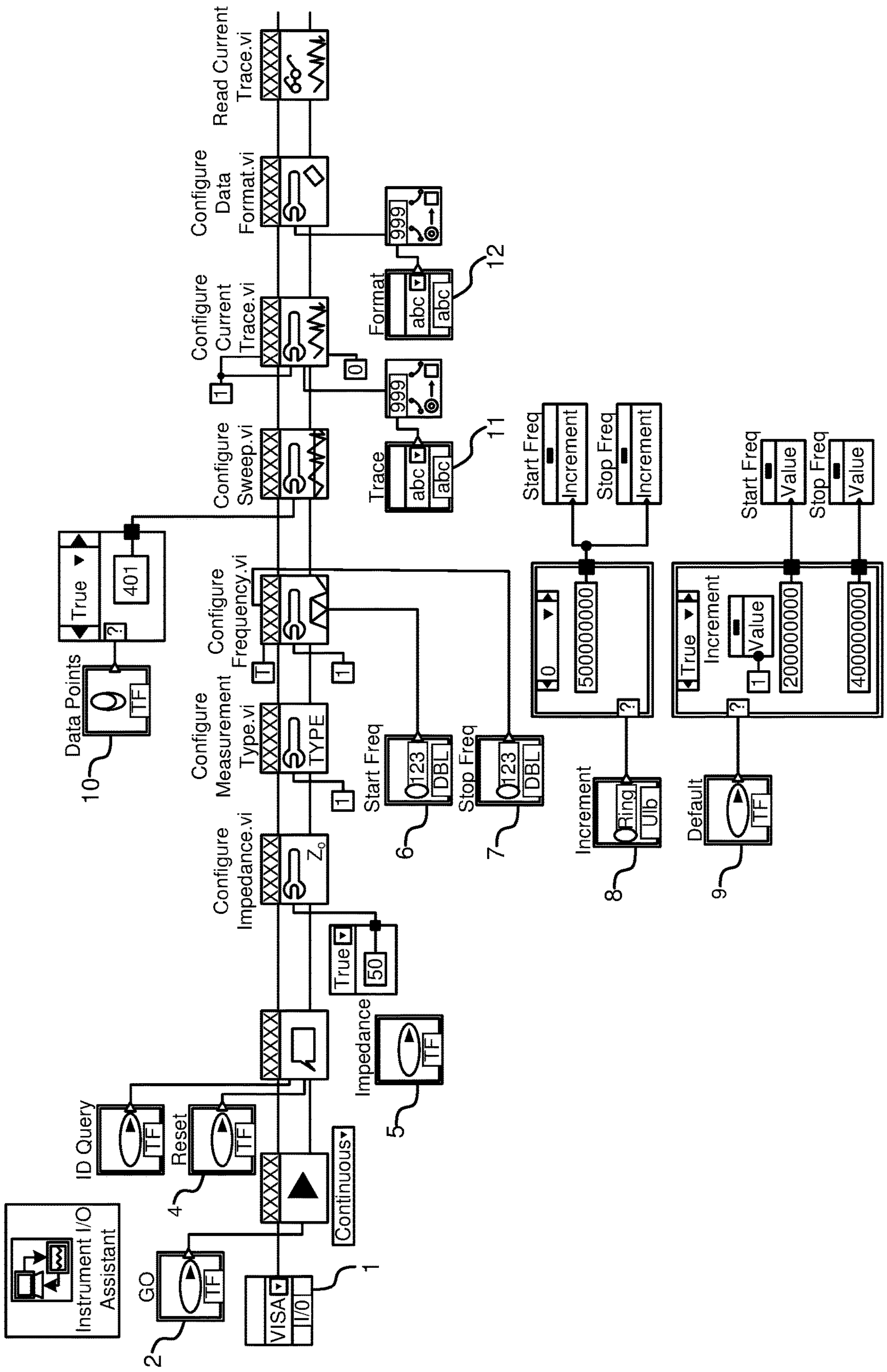
FIG. 32 is a diagram illustrating aspects of functional relationships and software modules that may be implemented in an interrogation system configured according to embodiments.
Figure 33:
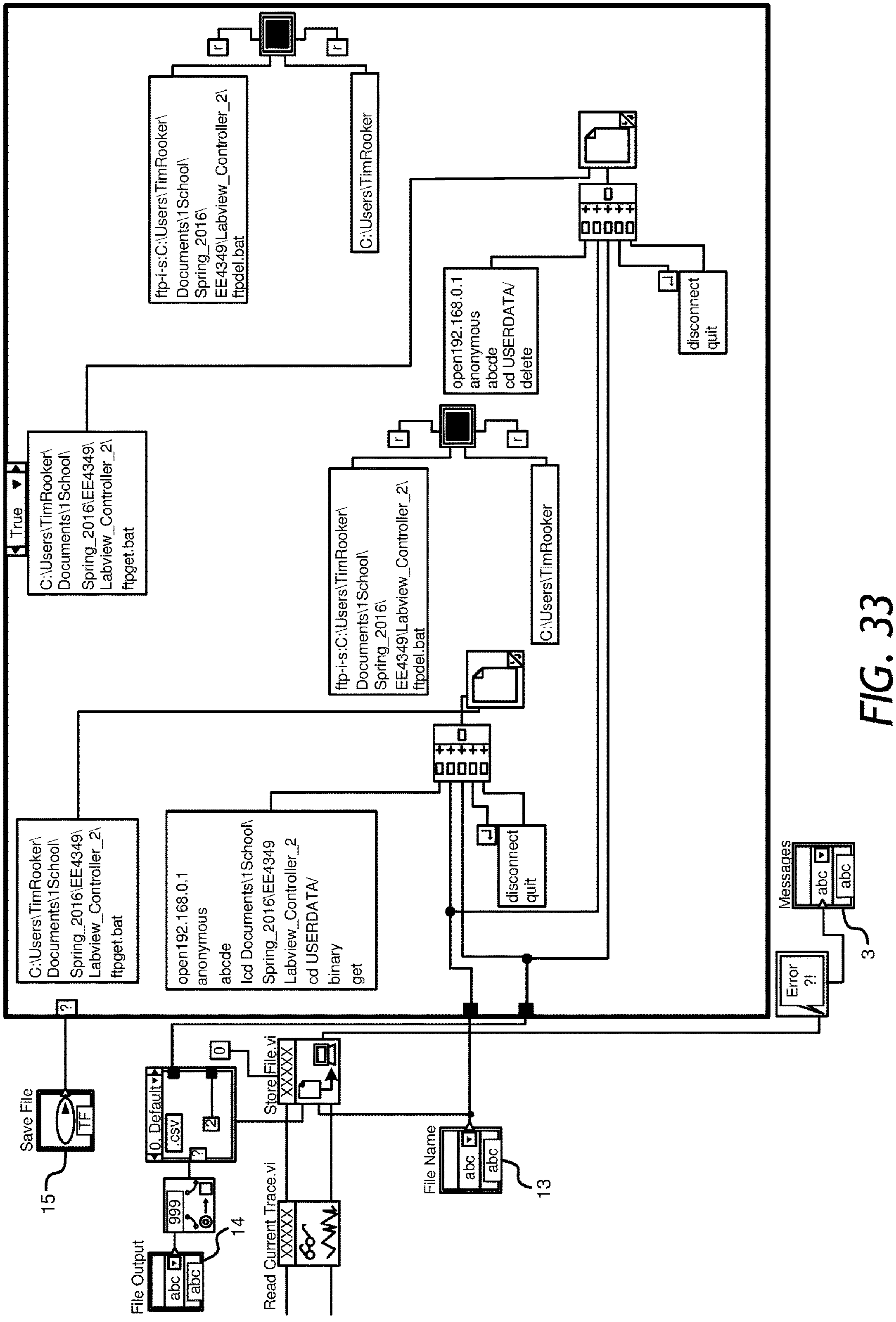
FIG. 33 is a diagram illustrating aspects of functional relationships and software modules that may be implemented in an interrogation system configured according to embodiments.
Figure 34:
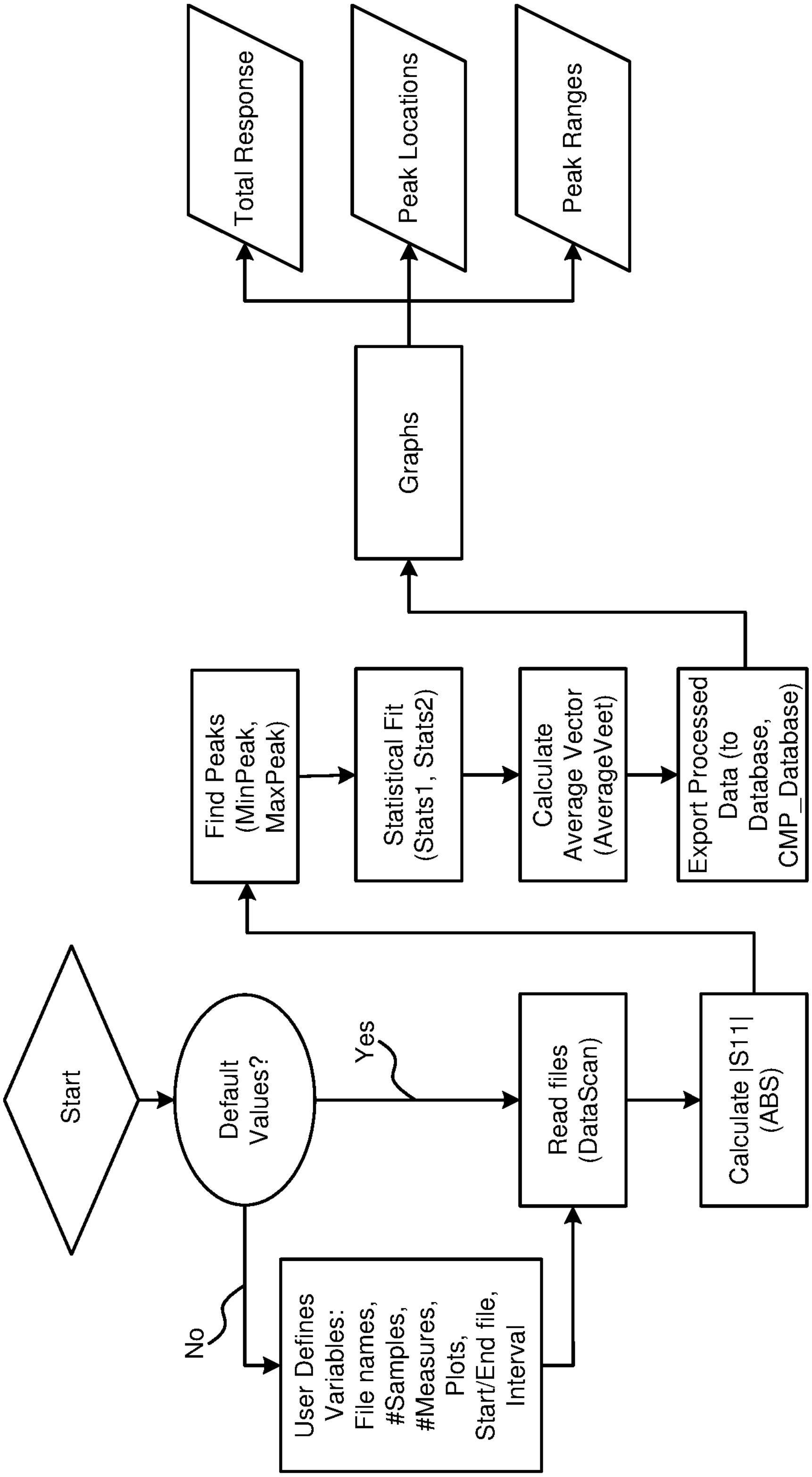
FIG. 34 is a diagram illustrating aspects of functional relationships and software modules that may be implemented in an interrogation system configured according to embodiments.

Referring to FIGS. 29-31, various aspects of a graphical user interface (GUI) for configuring a system for interrogation of a sample of an unknown material are shown. FIG. 29 illustrates an exemplary operations interface that may be utilized to execute the interrogation of a sample and compare signatures of the sample to one or more signatures in an existing database, such as the database 140 of FIG. 1. FIG. 30 illustrates an exemplary interface for configuring various parameters, such as the frequency ranges, S-parameters, port impedance, and sampling data points, for interrogating a sample. The exemplary interface illustrated in FIG. 30 also facilitates configuration of a desired Smith chart format. FIG. 31 illustrates various aspects of the exemplary interface illustrated in FIG. 30, and includes labels that identify the different functions provided by the exemplary interface. In FIGS. 32 and 33, diagrams illustrating various functional relationships of software modules that may be implemented in an interrogation system configured according to embodiments to provide the GUIs illustrated with reference to FIGS. 29-31 are shown. In some embodiments, the software modules may be stored as an application and/or instructions in a memory, such as memory 134 of FIG. 1. FIG. 30 is a flow diagram illustrating an exemplary method for identifying an unknown liquid according to an embodiment of the present disclosure.

Testing has shown that an interrogation system according to embodiments of the present disclosure is operable to noninvasively recognize or identify milk, milk mixed with water, milk mixed with alcohol, water, DI water, alcohol, liquor, coffee, carbonated drinks, such as sodas, and the like. Blind testing was also performed and resulted in accurate identification of one or more of these liquids. Additionally, testing has demonstrated that an interrogation system according to embodiments of the present disclosure is operable to recognize chemical reactions of two or more solutions within a container undergoing interrogation by an interrogation device according to embodiments of the present disclosure. For example, the signatures of the individual original solutions may be different from the solution that results after they are mixed together. Once the chemical reactions have completed, the changes in the S-parameters and/or in the Smith Chart become stable and the temporal variations can be used to identify the completion of chemical reactions. The similar principle is applied for detection of temperature changes in a liquid. For example, the signatures in the s-parameters and/or Smith Chart are different between water and ice. Thus, the temporal variations of the measurement can be used to identify the temperature changes in a solution. Further, monitoring has demonstrated that an interrogation system according to embodiments of the present disclosure is operable to test soil conditions, test solid particles in a solution, identify whole blood and plasma, test lubricants and oil, and the like, as explained above. For example, testing of soils conditions has been demonstrated by placing coils directly in samples of different soils and connecting the coils to an electronic device (e.g., to form an interrogation system similar to the system 100 of FIG. 1). When water was applied to the soils, the signatures in the S-parameter and Smith Chart changed to indicate the moisture content of the soil samples. Additionally, analysis of whole blood and plasma with different viscosity and biochemical contents, such as glucose and iron, results in different signatures, thereby allowing conditions of blood or plasma to be identified by embodiments of the present disclosure. Further, signatures for lubricants and oils with various moisture contents and impurity particles may also be used to monitor the quality of the lubricant/oil in order to determine if they should be replaced (e.g., to protect mechanical components that utilize the lubricant/oil). The embodiments of the present disclosure enable such applications to be performed continuously in situ, thus, providing a real-time monitoring system. Embodiments of an interrogation system according to the present disclosure may further be constructed to receive a finger and detect pulses, pulse rates and/or blood chemistry. For example, as blood travels through the blood vessels and veins in the finger, changes in signatures generated by an interrogation system of embodiments configured to interrogate a finger may be observed and may be used to determine the pulse. In some embodiments, interrogation systems may be formed on flexible substrates that may be deformed to wrap around a cylinder or body part, such as a finger, or may be formed as a solid object, such as a ring, that may be worn to provide real-time pulse monitoring. Additionally, some embodiments of the present interrogation systems may be extended to frequency rages in microwaves or millimeter waves for miniature containers (e.g., micro or nano-droplets).

EXAMPLES

The present invention will be described in greater detail by way of specific examples. The following examples are offered for illustrative purposes only and are not intended to limit the invention in any manner. Those of skill in the art will readily recognize a variety of noncritical parameters that can be changed or modified to yield essentially the same results.

An interrogator 100, having one coil with 5 turns wrapped around the body 116 was used to calculate the moisture content of three different soil samples: ASTM fine graded soil 3200, top soil 3210, and potting soil 3220. A commercial TDR sensor was also used to calculate the moisture content of the soils. The results for each sensor were generated and then compared. The sensors calculated the moisture content of each soil for five target moisture concentrations. The soil was dried in an oven to eliminate water content and then prepared by mixing water to the soil based on the weight ratio of the target water content. The mixed soil was then loaded into a compaction mold 3230 and compressed using a soil compaction hammer 3240. For the TDR soil calculations, data was recorded four times at the same soil location using Insitu MRP Test software. For the interrogator soil calculations, data was recorded ten times at the same soil location using VNA. After the calculations were made by the sensors, the water content of the soil was then measured again using dry density measurement to verify the target moisture concentration. The process was repeated for each soil at the five different target moisture concentrations.

Soil 1: ASTM Fine Graded (50-70) Sand

ASTM fine graded (50-70) sand was used to generate the test results at five target moisture concentrations: 2%, 5%, 8%, 11%, and 14%. The results of the moisture content calculations for the interrogator and TDR are shown below in Table 1. Taking the average for all five target concentrations, the interrogator results have approximately a twelve percent error when calculating the target water percentages. The TDR results are less accurate having, on average, approximately forty one percent error when calculating the target water percentages. The more accurate results of the interrogator are at least in part due to the frequency verification values. The frequency shift of the first, second and third feature verification can indicate the water percentages in the soil. The feature verification values can be used as parameters or signatures to verify the moisture content as described above.

TABLE 1

Results of ASTM Soil Calculations

| Soil | Target Water Percentage | Interrogator Results (%) | TDR Results (%) | Feature Verification 1 | Feature Verification 2 | Feature Verification 3 |
|---|---|---|---|---|---|---|
| ASTM soil | 2 | 1.87 | 4.9 | 334.5 | 484.65 | 665.39 |
| ASTM soil | 5 | 4.48 | 6.46 | 301.95 | 441.6 | 593.5 |
| ASTM soil | 8 | 6.97 | 7.97 | 261.7 | 386.65 | 513.28 |
| ASTM soil | 11 | 8.81 | 9.94 | 250.5 | 370.2 | 494.1 |
| ASTM soil | 14 | 12.54 | 10.73 | 226 | 333.8 | 440.9 |

Soil 2: Top Soil

Top Soil was used to generate the test results at five target moisture concentrations: 2%, 7%, 12%, 17%, and 22%. The results of the moisture content calculations for the interrogator and TDR are shown below in Table 2. Taking the average for all five target concentrations, the interrogator results have approximately a fourteen percent error when calculating the target water percentages for top soil. The TDR results are less accurate having, on average, approximately forty three percent error when calculating the target water percentages. The results for the top soil are similar to those found to the ASTM soil; however, a soil containing other materials such as organic matter will cause the TDR results to become inaccurate.

TABLE 2

Results of Top Soil Calculations

| Soil | Target Water Percentage | Interrogator Results (%) | TDR Results (%) | Feature Verification 1 | Feature Verification 2 | Feature Verification 3 |
|---|---|---|---|---|---|---|
| Top Soil | 2 | 2.61 | 5.71 | 342.2 | 510.8 | 693.2 |
| Top Soil | 7 | 7.93 | 7.39 | 314.6 | 473.42 | 638.96 |
| Top Soil | 12 | 13.41 | 12.36 | 302.6 | 451.34 | 608.6 |
| Top Soil | 17 | 18.44 | 15.2 | 291.1 | 429.7 | 580.48 |
| Top Soil | 22 | 23.44 | 24.75 | 257.99 | 381.4 | 508.8 |

Soil 2: Potting Soil

Potting Soil was used to generate the test results at five target moisture concentrations: 2%, 7%, 12%, 17%, and 22%. The results of the moisture content calculations for the interrogator and TDR are shown below in Table 1. Potting soil contains a lot of different materials; some common ingredients used in potting soil are peat, composted bark, sand, perlite and recycled mushroom compost. Potting soil is also aerated making calculation of the moisture content difficult. As a result, the Interrogator results have, on average, approximately a forty five percent error when calculating the target water percentages for potting soil. The TDR results fair much worse having over one thousand percent error when calculating the water percentage in potting soil. The introduction of new materials and air have a less harmful effect of the interrogator results partly because the feature verification values can still be used to cross check the results of the interrogator, as described above.

TABLE 3

Results of Potting Soil Calculations

| Soil | Target Water Percentage | Interrogator Results (%) | TDR Results (%) | Feature Verification 1 | Feature Verification 2 | Feature Verification 3 |
|---|---|---|---|---|---|---|
| Potting soil | 2 | 5.12 | 55.07 | 238.6 | 409.4 | 597.7 |
| Potting soil | 7 | 8.11 | 108.8 | 233.7 | 405.06 | 580.2 |
| Potting soil | 12 | 10 | 202.17 | 228.1 | 399.32 | 570.19 |
| Potting soil | 17 | 19.89 | 11.85 | 214.1 | 374.19 | 536.1 |
| Potting soil | 22 | 26.75 | 9.81 | 209.27 | 361.38 | 532.8 |

Figure 35:
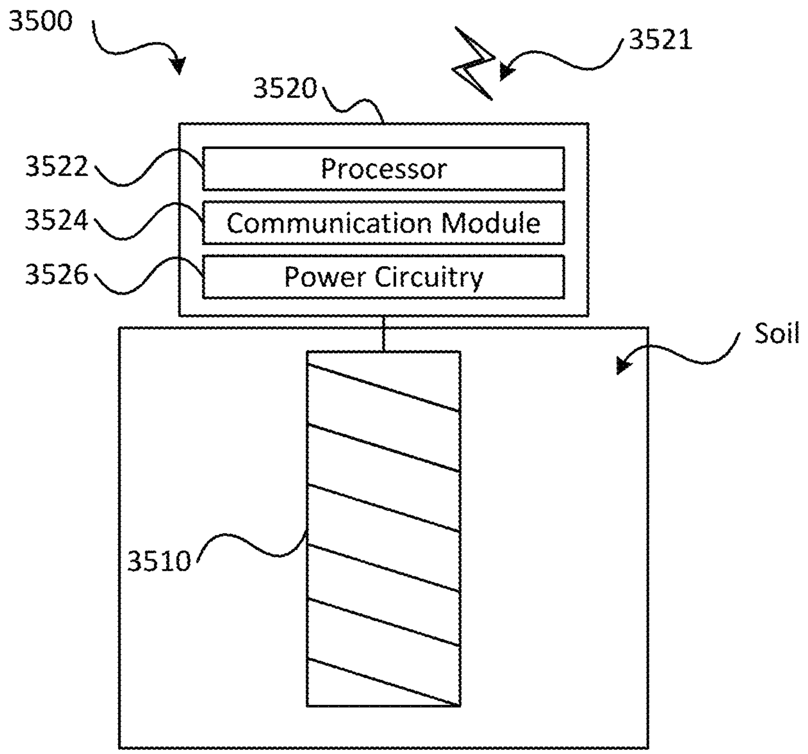
FIG. 35 is a block diagram illustrating aspects of a system for determining an amount of liquid within a volume of a material according to embodiments of the present disclosure.

Referring to FIG. 35, a block diagram of a system for determining an amount of liquid within a volume of a material according to embodiments of the present disclosure is shown as a system 3500. As shown in FIG. 35, the system 3500 includes a resonator 3510 and a reader device 3520. As described in more detail below, the system 3500 may be configured to determine an amount of liquid present in a volume of soil in which the resonator 3510 is disposed.

The reader device 3520 may include a processor 3522, a communication module 3524, and power circuitry 3526. Although not shown in FIG. 35, the reader device 3520 may also include a memory, a power source, and one or more input/output (I/O) ports. The memory may store instructions that, when executed by the processor 3522, cause the processor 3522 to perform the operations described in connection with the reader device 3520 with reference to FIG. 35. Additionally, the memory may be configured to store measurement data, such as information associated with output signals generated by the resonator 3510, resonant frequencies calculated based on output signals generated by the resonator 3510, estimates of the amount of liquid present in the volume, and other information. The reader device 3520 may be configured to timestamp the measurement data stored at the memory to facilitate monitoring of the amount of liquid over time. This may enable the measurement data to be subsequently analyzed and correlated with various events, such as rainfall, activation of an irrigation system, and the like, which may provide insights into how those events impact the amount of liquid within the soil over time.

The communication module 3524 may be configured to communicatively couple the reader device 3520 to the remote device via a wireless communication link 3521 established according to one or more wireless communication or standards (e.g., a transmission control protocol/internet protocol (TCP/IP), an institute of electrical and electronics engineers (IEEE) 802.11 protocol, and an IEEE 802.16 protocol, a $3^{rd}$ generation (3G) protocol, a $4^{th}$ generation (4G)/long term evolution (LTE) protocol, etc.). The reader device 3520 may be configured to periodically transmit the measurement data (e.g., one or more parameters associated with output signals generated by the resonator 3510 and/or moisture content determinations) to a remote device. Additionally or alternatively, the reader device 3520 may be configured to transmit other information to the remote device. For example, the remote device may be a controller coupled to a sprinkler system, and the reader device 3520 may be configured to transmit a control signal the controller when the amount of liquid (e.g., water) in the soil falls below a threshold amount. The controller may activate the sprinkler system in response to receiving the control signal. Further, the reader device 3520 may be directly coupled to an external device (not shown in FIG. 35) via one of the I/O ports (e.g., a universal serial bus (USB) port) so that data stored in the memory of the reader device 3520 may be downloaded directly to the external device.

The reader device 3520 may provide an input signal to the resonator 3510. In embodiments, the power circuitry 3526 may be configured to generate the input signal. For example, the resonator 3510 may include one or more coils, such as the coil(s) 112 of FIG. 1, and the power circuitry 3526 may be configured to excite the one or more coils of the resonator 3510. The input signal may be configured to induce, or otherwise cause, the resonator 3510 to generate an output signal representative of the behavior of the resonator 3510, and the output signal may be detected by the reader device 3520. In embodiments, the output signal may be detected and one or more parameters representative of the behavior of the resonator 3510 in response to the input signal may be identified, as described above. In some embodiments, the power circuitry 3526 may include a matching circuit configured to perform impedance matching with respect to the input signal provided to the resonator 3510.

The reader device 3520 may be configured to analyze the output signals generated by the resonator 3510 to determine the amount of liquid within the soil (e.g., the moisture content of the soil). For example, the output signal may be analyzed by the reader device 3520 to identify one or more parameters (e.g., S-parameters, resonant frequencies, and the like) associated with the output signal, and then, as described in the specific examples above, the one or more parameters associated with the output signal may be used to determine the moisture content of the soil.

As shown above, the system 3500 enables determinations to be made regarding an amount of liquid, such as water, within a volume of soil. The system 3500 provides several advantages over existing technologies, such as the aforementioned TDR devices. For example, the system 3500 may facilitate analysis of moisture content over a larger volume of soil than existing TDR devices. TDR devices typically include a probe connected to electronics. The probe is typically formed from 2 metal rods, and the electronics send a pulse waveform of voltage into the probe. The signal travels down the rods into the soil. At the end of the two rods, the signal returns (reflects) back to the beginning of the rods. The returning pulse waveform is affected by the materials between the two rods and the length of the rods. The soil between the rods has different permittivity depending on how much water it holds. TDR devices utilize a formula and the shape of the returning pulse waveform to calculate the permittivity to determine water content. However, this technique only measures the soil between the rods of the TDR probe, which are typically separated by a small distance (e.g., approximately 2 centimeters (cm) or less). In contrast, the system 3500 is configured to detect moisture contents within the soil based on an overall permittivity of a volume of soil in which the resonator 3510 is disposed. For example, the resonant frequency of the output signal produced by the resonator 3510 may be representative of the permittivity across the volume of soil in which the resonator 3510 is disposed. Thus, the system 3500 may facilitate rapid analysis of moisture content within a larger volume of soil, as described in more detail below with respect to FIGS. 40A-40D.

Figure 36:
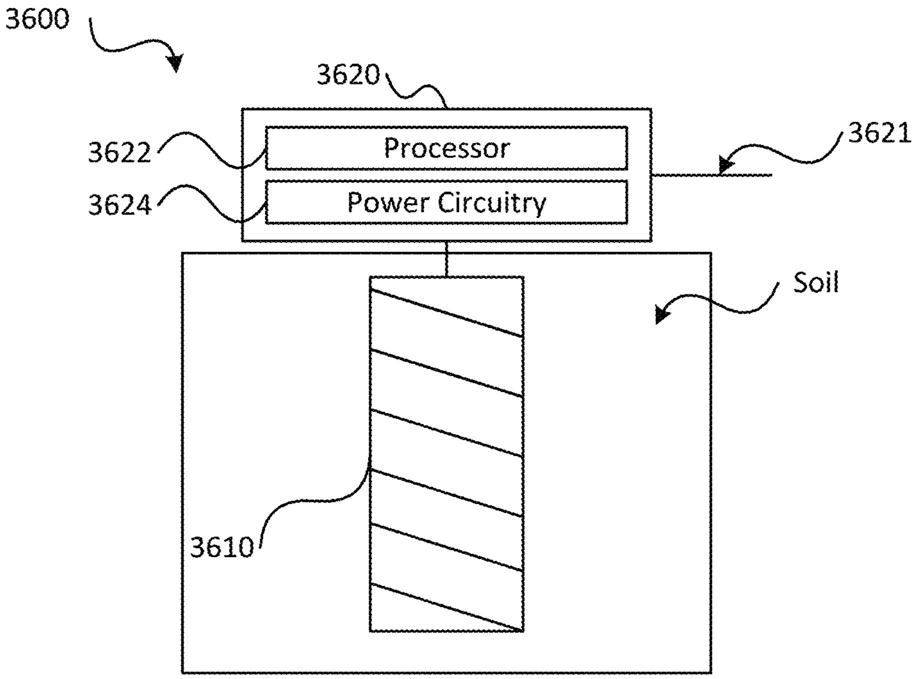
FIG. 36 is a block diagram illustrating aspects of another system for determining an amount of liquid within a volume of a material according to embodiments of the present disclosure.

Referring to FIG. 36, a block diagram illustrating aspects of another system for determining an amount of liquid within a volume of a material according to embodiments of the present disclosure is shown as a system 3600. As shown in FIG. 36, the system 3600 includes a resonator 3610 and a reader device 3620. As described in more detail below, the system 3600 may be configured to determine an amount of liquid present in a volume of soil in which the resonator 3610 is disposed.

The reader device 3620 may include a processor 3622, and power circuitry 3624. Although not shown in FIG. 36, the reader device 3620 may also include a memory, a power source, one or more input/output (I/O) ports, and a communication module. The memory may store instructions that, when executed by the processor 3622, cause the processor 3622 to perform the operations described in connection with the reader device 3620 with reference to FIG. 36. Additionally, the memory may be configured to store measurement data, such as information associated with output signals generated by the resonator 3610, resonant frequencies calculated based on output signals generated by the resonator 3610, estimates of the amount of liquid present in the volume, and other information. The reader device 3620 may be configured to timestamp the measurement data stored at the memory to facilitate monitoring of the amount of liquid over time. This may enable the measurement data to be subsequently analyzed and correlated with various events, such as rainfall, activation of an irrigation system, and the like, which may provide insights into how those events impact the amount of liquid within the soil over time.

The reader device 3620 may include a communication module (not shown in FIG. 36 for simplicity of the figure) configured to communicatively couple the reader device 3620 to the remote device via a wired communication link 3621 established according to one or more wireless communication or standards (e.g., an Ethernet protocol, a TCP/IP protocol, etc.). The reader device 3620 may be configured to periodically transmit the measurement data (e.g., one or more parameters associated with output signals generated by the resonator 3610 and/or moisture content determinations) to a remote device. Additionally or alternatively, the reader device 3620 may be configured to transmit other information to the remote device. For example, the remote device may be a controller coupled to a sprinkler system, and the reader device 3620 may be configured to transmit a control signal to the controller when the amount of liquid (e.g., water) in the soil falls below a threshold amount. The controller may activate the sprinkler system in response to receiving the control signal. Further, the reader device 3620 may be directly coupled to an external device (not shown in FIG. 36) via one of the I/O ports (e.g., a USB port) so that data stored in the memory of the reader device 3620 may be downloaded directly to the external device.

The reader device 3620 may provide an input signal to the resonator 3610. In embodiments, the power circuitry 3624 may be configured to generate the input signal. For example, the resonator 3610 may include one or more coils, such as the coil(s) 112 of FIG. 1, and the power circuitry 3624 may be configured to excite the one or more coils of the resonator 3610. The input signal may be configured to induce, or otherwise cause, the resonator 3610 to generate an output signal representative of the behavior of the resonator 3610, and the output signal may be detected by the reader device 3620. In embodiments, the output signal may be detected as one or more parameters (e.g., S-parameters, resonant frequencies, and the like) representative of the behavior of the resonator 3610 in response to the input signal, as described above. In some embodiments, the power circuitry 3624 may include a matching circuit configured to perform impedance matching with respect to the input signal provided to the resonator 3610.

The reader device 3620 may be configured to analyze the output signals generated by the resonator 3610 to determine the amount of liquid within the soil. For example, the output signal may be analyzed by the reader device 3620 to identify the one or more parameters associated with the output signal, and then, as described above, the identified one or more parameters associated with the output signal may be used to determine the moisture content of the soil.

As shown above, the system 3600 enables determinations to be made regarding an amount of liquid, such as water, within a volume of soil. The system 3600 provides several advantages over existing technologies, such as the aforementioned TDR devices. For example, as explained above with reference to FIG. 35, the system 3600 may facilitate analysis of moisture content over a larger volume of soil than existing TDR devices (e.g., because TDR devices only measure the soil between the narrowly spaced rods of the TDR probe), as described in more detail below with respect to FIGS. 40A-40D.

Figure 37A:
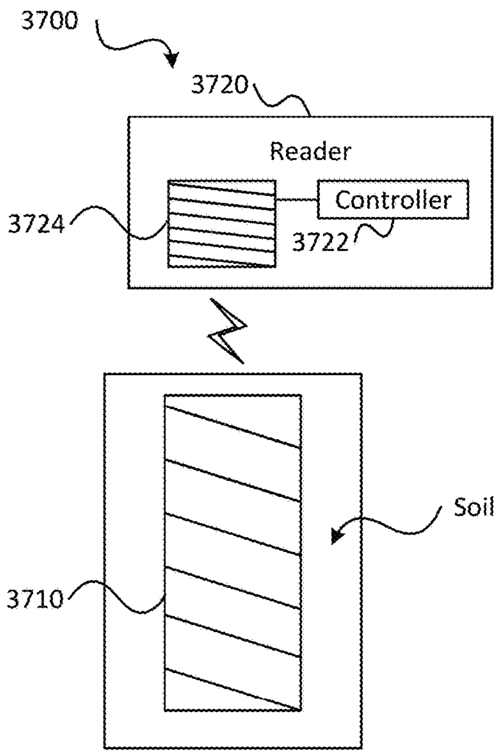
FIG. 37A is a block diagram illustrating aspects of another system for determining an amount of liquid within a volume of a material according to embodiments of the present disclosure.

Referring to FIG. 37A, a block diagram illustrating aspects of another system for determining an amount of liquid within a volume of a material according to embodiments of the present disclosure is shown as a system 3700. As shown in FIG. 37, the system 3700 includes a resonator 3710 and a reader device 3720. As described in more detail below, the system 3700 may be configured to determine an amount of liquid present in a volume of soil in which the resonator 3710 is disposed.

Figure 37B:
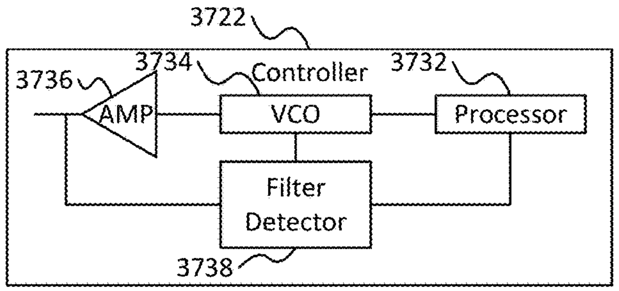
FIG. 37B is a block diagram illustrating aspects of circuitry for use by a system for determining an amount of liquid within a volume of a material according to embodiments of the present disclosure.

The reader device 3720 may include a controller 3722, and a transmitter 3724. Referring briefly to FIG. 37B, a block diagram illustrating aspects of a controller for use by the system 3700 for determining an amount of liquid within a volume of a material according to embodiments of the present disclosure is shown. As shown in FIG. 37B, the controller 3722 may include a processor 3732, a voltage controlled oscillator (VCO) 3734, an amplifier 3736, and a filter detector 3738. The VCO 3734 may be configured to create resonant frequency signals that are then amplified by the amplifier 3736. In embodiments, the processor 3732 may be configured to control the creation of the particular resonant frequency signals by the VCO 3734.

Referring back to FIG. 37A, the controller 3722 may provide the signals generated by the VCO 3734 and the amplifier 3736 to the transmitter 3724 for transmission as an input signal to the resonator 3710. In embodiments, the transmitter 3724 may include a coil and the input signal may be an electromagnetic signal emitted by the transmitter 3724. The reader device 3720 may be used to periodically determine an amount of liquid within a volume of soil. For example, the reader device 3720 may be placed in proximity (e.g., within a few meters) of the location where the resonator 3710 is disposed within the soil, and, once in proximity to the resonator 3710, the reader device 3720 may provide the input signal to the resonator 3710. The input signal may be configured to induce, or otherwise cause, the resonator 3710 to generate an output signal representative of the behavior of the resonator 3710, and the output signal may be detected by the reader device 3720.

The reader device 3720 may be configured to analyze the output signals generated by the resonator 3710 to determine the amount of liquid within the soil. For example and referring back to FIG. 37B, the output signal generated by the resonator 3710 may be detected by the reader device 3720, and the filter detector 3738 may isolate the output signal, which may be provided to the processor 3732 for further processing. The isolated output signal may be analyzed by the reader device 3720 to identify one or more parameters (e.g., S-parameters, resonant frequencies, and the like) associated with the output signal, and then, as described above, the identified one or more parameters may be used to determine the moisture content of the soil.

Although not shown in FIG. 37, the reader device 3720 may also include a memory, a power source, one or more input/output (I/O) ports, and a communication module. The memory may store instructions that, when executed by a processor (e.g., the processor 3732), cause the processor to perform the operations described in connection with the reader device 3720 with reference to FIGS. 37A and 37B. Additionally, the memory may be configured to store measurement data, such as information associated with output signals generated by the resonator 3710, resonant frequencies calculated based on output signals generated by the resonator 3710, estimates of the amount of liquid present in the volume, and other information. The reader device 3720 may be configured to timestamp the measurement data stored at the memory to facilitate monitoring of the amount of liquid over time. This may enable the measurement data to be subsequently analyzed and correlated with various events, such as rainfall, activation of an irrigation system, and the like, which may provide insights into how those events impact the amount of liquid within the soil over time.

As shown above, the system 3700 enables determinations to be made regarding an amount of liquid, such as water, within a volume of soil. The system 3700 provides several advantages over existing technologies, such as the aforementioned TDR devices. For example, the system 3700 may facilitate system deployments that provide improvements with respect to power and power consumption as compared to existing TDR devices. In particular, as illustrated in FIGS. 37A and 37B, the system 3700 facilitates passive sensing by placing a resonator 3710 configured to exhibit a specific resonant frequency (depending on the moisture content of the surrounding soil) in soil without any additional circuitry (other than the resonator 3710). To achieve passive sensing, the reader device 3720 transmits an input signal transmitted that is received by the resonator 3710, causing the resonator 3710 to produce an output signal that is detected by the reader device 3720, where the output signal shows high signal strength at one or more resonant frequencies. Thus, the system 3700 does not require the resonator 3710 to be coupled to a power source, such as a battery, solar panel, or other source of electricity. As explained above, TDR devices require electronics to send the pulse waveform into the probe and detect the shape of the returning pulse. It is difficult to preserve the return pulse shape and transmit it back to a reader because the pulse contains a wide bandwidth of frequencies. Thus, TDR systems require a power source to be coupled to the sensing instrumentation. Additionally, as explained above with reference to FIG. 35, the system 3700 may facilitate analysis of moisture content over a larger volume of soil than existing TDR devices (e.g., because TDR devices only measure the soil between the narrowly spaced rods of the TDR probe), as described in more detail below with respect to FIGS. 40A-40D.

Figure 38:
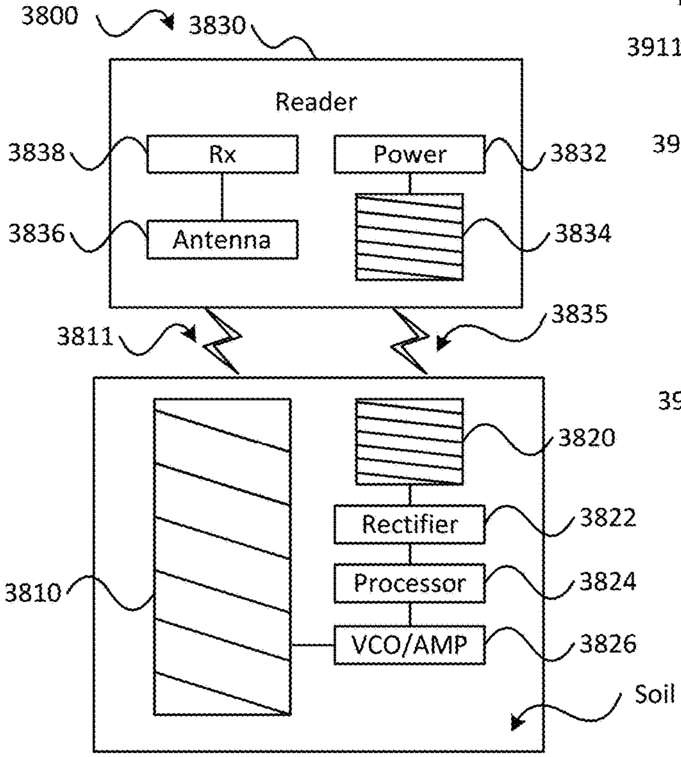
FIG. 38 is a block diagram illustrating aspects of another system for determining an amount of liquid within a volume of a material according to embodiments of the present disclosure.

Referring to FIG. 38, a block diagram illustrating aspects of another system for determining an amount of liquid within a volume of a material according to embodiments of the present disclosure is shown as a system 3800. As shown in FIG. 38, the system 3800 includes a resonator 3810, a reader device 3830, and an activation device that includes a coil 3820, a rectifier 3822, a processor 3724, and a VCO/AMP 3836. As described in more detail below, the system 3800 may be configured to determine an amount of liquid present in a volume of soil in which the resonator 3810 is disposed.

As shown in FIG. 38, the reader device 3830 may include a power circuit 3832, a coil 3834, an antenna 3836, and a receiver module 3838. Although not shown in FIG. 38, the reader device 3830 may also include a processor, a memory, a power source, one or more input/output (I/O) ports, and a communication module. The memory may store instructions that, when executed by the processor, cause the processor to perform the operations described in connection with the reader device 3830 with reference to FIG. 38. Additionally, the memory may be configured to store measurement data, such as information associated with output signals generated by the resonator 3810, resonant frequencies calculated based on output signals generated by the resonator 3810, estimates of the amount of liquid present in the volume, and other information. The reader device 3830 may be configured to timestamp the measurement data stored at the memory to facilitate monitoring of the amount of liquid over time. This may enable the measurement data to be subsequently analyzed and correlated with various events, such as rainfall, activation of an irrigation system, and the like, which may provide insights into how those events impact the amount of liquid within the soil over time.

The power circuit 3832 may activate the coil 3832. Upon activation, the coil 3832 may be configured to emit a wireless signal 3835. The wireless signal 3835 may be received at the coil 3820, and may cause the coil 3820 to provide an input signal to the rectifier 3822. The rectifier 3822 may be configured to generate and provide power to the processor 3824 and the VCO/AMP 3826 based on the signal received from the coil 3820. The processor 3824 and the VCO/AMP 3826 may generate resonant frequency signals that are configured to induce, or otherwise cause, the resonator 3810 to generate an output signal 3811 representative of the behavior of the resonator 3810. In embodiments, the input signals generated by the coil 3834 and the output signal 3811 may have different frequencies. In embodiments, the wireless signal 3835 may be an electromagnetic signal. However, it is noted that the system 3800 may be configured to utilize other types of signals and power generation circuitry in some embodiments. For example, the system 3800 may be modified to utilize power transfer techniques that utilize optical signals (e.g., the reader device 3830 transmits optical signals that include modulated radio frequency signals embedded therein to the activation device), acoustic waves (e.g., ultrasound), or other power transfer techniques.

The output signal 3811 may be detected by the antenna 3836 and the receive module 3838 of the reader device 3830. The reader device 3830 may be configured to analyze the output signal generated by the resonator 3810 to determine the amount of liquid within the soil. For example, the output signal 3811 may be analyzed by the reader device 3830 to identify one or more parameters (e.g., S-parameters, resonant frequencies, and the like) associated with the output signal 3811, and then, as described in the specific examples above, the identified one or more parameters associated with the output signal 3811 may be used to determine the moisture content of the soil.

As described above, the reader device 3830 may be used to periodically determine an amount of liquid within a volume of soil. For example, the reader device 3830 may be placed in proximity (e.g., within a few meters) of the location where the resonator 3810 and coil 3820, which are disposed within the soil, and, once in proximity to the resonator 3810, the reader device 3830 may provide the input signal 3835 to the coil 3820. This effectively turns the "in-ground" components on, resulting in the output signal 3811, which is detected by the reader device 3830, as described above. When the reader device 3830 ceases to provide the input signal 3835, the "in-ground" components turn off (e.g., because the rectifier 3822 is no longer receiving the signal output by the coil 3820).

As shown above, the system 3800 enables determinations to be made regarding an amount of liquid, such as water, within a volume of soil. The system 3800 provides several advantages over existing technologies, such as the aforementioned TDR devices. For example, the system 3800 may facilitate system deployments utilizing passive sensing, as explained above with reference to FIGS. 37A and 37B. It is noted that the passive sensing provided by the system 3800 differs from the passive sensing provided by the system 3700 in the sense that the system 3800 includes additional circuitry is disposed in the ground proximate the resonator 3810; however, this additional circuitry does not store power (e.g., as in a battery) and is not coupled to a constant power source (e.g., as may be provided by a physical connection to an electrical grid). Additionally, unlike a solar panel that produces power whenever it is in the presence of sunlight (e.g., even when the system is not being used for sensing operations), the additional circuitry does not generate power outside of sensing operations (e.g., use of the reader device 3830 to provide the input signal 3835). Thus, the system 3800 may be considered a passive system for determining moisture content. Further, as explained above with reference to FIG. 35, the system 3800 may facilitate analysis of moisture content over a larger volume of soil than existing TDR devices (e.g., because TDR devices only measure the soil between the narrowly spaced rods of the TDR probe), as described in more detail below with respect to FIGS. 40A-40D.

Figure 39:
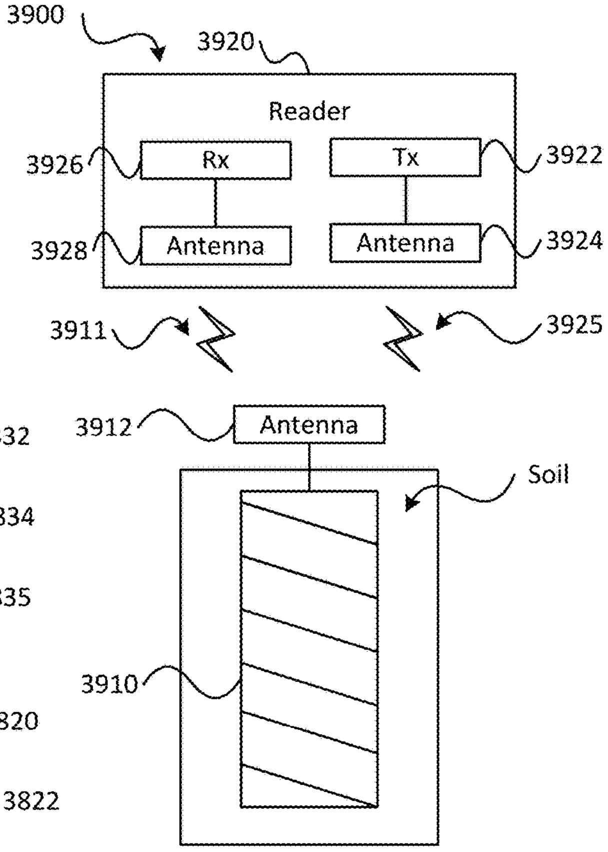
FIG. 39 is a block diagram illustrating aspects of another system for determining an amount of liquid within a volume of a material according to embodiments of the present disclosure.

Referring to FIG. 39, a block diagram illustrating aspects of another system for determining an amount of liquid within a volume of a material according to embodiments of the present disclosure is shown as a system 3900. As shown in FIG. 39, the system 3900 includes a resonator 3910, an antenna 3912, and a reader device 3920. As described in more detail below, the system 3900 may be configured to determine an amount of liquid present in a volume of soil in which the resonator 3910 is disposed.

The reader device 3920 may include a transmitter 3922, a transmit antenna 3924, a receiver 3926, and a receive antenna 3928. Although not shown in FIG. 39 for simplicity of the figure, the reader device 3920 may also include a processor, a memory, a power source, one or more input/output (I/O) ports, and a communication module. The memory may store instructions that, when executed by the processor of the reader device 3920, cause the processor to perform the operations described in connection with the reader device 3920, such as controlling transmission of the input signals 3925 by the transmit module 3922 and the antenna 3924 and processing the output signal(s) 3911 received by the antenna 3928 and the receive module 3926 to determine the moisture content of the soil. Additionally, the memory may be configured to store measurement data, such as information associated with output signals generated by the resonator 3910, one or more parameters (e.g., S-parameters, resonant frequencies, and the like) associated with the output signals generated by the resonator 3910, estimates of the amount of liquid present in the volume, and other information. The reader device 3920 may be configured to timestamp the measurement data stored at the memory to facilitate monitoring of the amount of liquid over time. This may enable the measurement data to be subsequently analyzed and correlated with various events, such as rainfall, activation of an irrigation system, and the like, which may provide insights into how those events impact the amount of liquid within the soil over time.

The transmit module 3922 may be configured to transmit, via the transmit antenna 3924, input signals 3925 configured to induce, or otherwise cause, the resonator 3910 to generate an output signal 3911 representative of the behavior of the resonator 3910. As shown in FIG. 39, the resonator 3910 may be coupled to an antenna 3912. The antenna 3912 may enable reception of the input signals 3925 from a greater distance than if the resonator was not coupled to the antenna 3912. The output signal 3911 may be detected by the reader device 3620. For example, the output signal 3911 may be detected by the receive module 3926 via the receive antenna 3928. Upon receiving the output signal(s) 3911, the reader device 3920 may be configured to analyze characteristics of the output signal(s) 3911 to determine one or more parameters (e.g., S-parameters, resonant frequencies, and the like) associated with the output signal(s) 3911. For example, the receive module 3926, or a processor (not shown in FIG. 39) of the reader device 3920, may be configured to detect return pulses (e.g., the output signal(s) 3911) and analyze the return pulses to identify an output signal 3911 corresponding to a return signal associated with the input signals 3925. In embodiments, the return signals associated with the input signals 3925 may be identified based on a time delay. For example, the receive module 3926 or the processor of the reader device 3920 may be provided with information associated with the frequencies of the input signals 3925 generated by the transmit module 3922, and based on this information, the receive module 3926 or processor may use time delay information and information associated with the input signal frequencies to identify the output signal(s) 3911 corresponding to particular responses by the resonator 3910 to the input signals 3925. Based on the identified return pulses, the receive module 3926 or the processor may determine one or more parameters representative of the behavioral response of the resonator 3910 to the input signals 3925, such as S-parameters, resonant frequencies, and other characteristics of the output signal(s) 3911, as described above. In embodiments, the transmit module 3922 may be configured to sweep the input signal 3925 across a range of frequencies, as described above with reference to FIG. 4. The reader device 3920 may be configured to determine the moisture content of the soil based on the one or more parameters associated with the received output signal(s) 3911, as described above.

As shown above, the system 3900 enables determinations to be made regarding an amount of liquid, such as water, within a volume of soil. The system 3900 provides several advantages over existing technologies, such as the aforementioned TDR devices. For example, the system 3900 may facilitate system deployments utilizing passive sensing, as explained above with reference to FIGS. 37A and 37B. Additionally, as explained above with reference to FIG. 35, the system 3900 may facilitate analysis of moisture content over a larger volume of soil than existing TDR devices (e.g., because TDR devices only measure the soil between the narrowly spaced rods of the TDR probe), as described in more detail below with respect to FIGS. 40A-40D.

Figures 40A, 40B, 40C, 40D, 41:
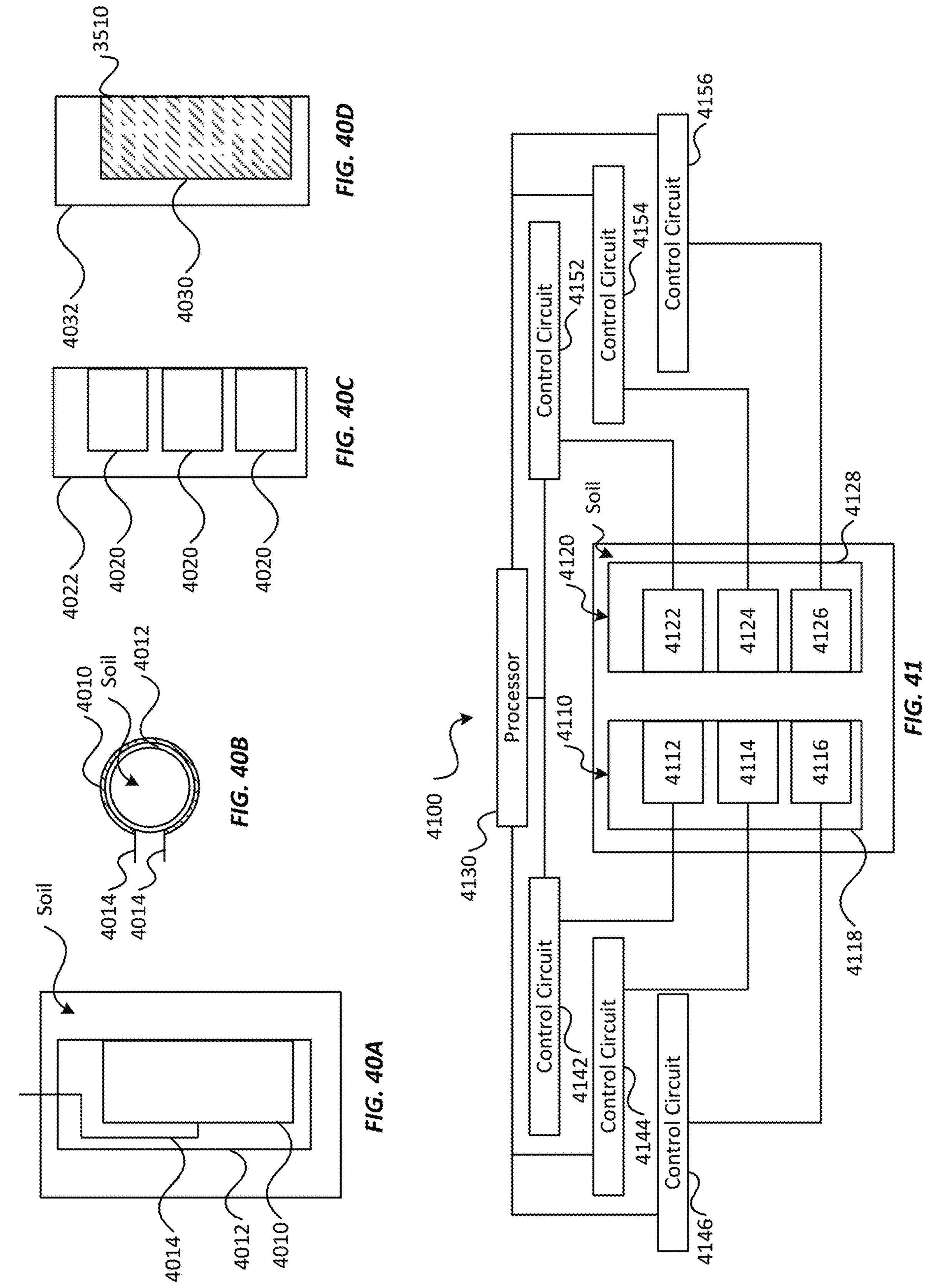
FIG. 40A is a block diagram illustrating aspects of a resonator configuration for use in a system for determining an amount of liquid within a volume of a material according to embodiments of the present disclosure.
FIG. 40B is a block diagram illustrating additional aspects of a resonator configuration for use in a system for determining an amount of liquid within a volume of a material according to embodiments of the present disclosure.
FIG. 40C is a block diagram illustrating additional aspects of a resonator configuration for use in a system for determining an amount of liquid within a volume of a material according to embodiments of the present disclosure.
FIG. 40D is a block diagram illustrating additional aspects of a resonator configuration for use in a system for determining an amount of liquid within a volume of a material according to embodiments of the present disclosure.
FIG. 41 is a block diagram illustrating aspects of another system for determining an amount of liquid within a volume of a material according to embodiments of the present disclosure.

Referring to FIGS. 40A and 40B, block diagrams illustrating aspects of a resonator configuration for use in a system for determining an amount of liquid within a volume of a material according to embodiments of the present disclosure are shown. As shown in FIGS. 40A and 40B, in some embodiments, rather than using a coil-based resonator, such as the coil-based resonators illustrated in FIGS. 35-39, various ones of the embodiments illustrated in FIGS. 35-39 may utilize resonators formed from patches or strips of metal wrapped around a cylinder. For example, in FIGS. 40A and 40B, a metal patch 4010 is illustrated. The metal patch 4010 has been wrapped around a cylinder 4012. In embodiments where the resonator is coupled to an external device (e.g., the reader device 3520 of FIG. 35, the reader device 3620 of FIG. 36, or the antenna 3912 of FIG. 39), the metal patch 4010 may be coupled to the external device via one or more leads 4014.

The resonator configuration illustrated in FIGS. 40A and 40B may be utilized with any of the systems described above with reference to FIGS. 35-39 and/or the systems described below with reference to FIGS. 41 and 42A-42C to make determinations regarding an amount of liquid, such as water, within a volume of soil. In such system configurations, the advantages over existing technologies, such as the aforementioned TDR devices, may also be realized. For example, moisture content detection systems utilizing resonators configured with metal patches and/or strips according to embodiments may facilitate system deployments utilizing passive sensing, as explained above with reference to FIGS. 37A and 37B. Additionally, as explained above with reference to FIG. 35, such systems may facilitate analysis of moisture content over a larger volume of soil than existing TDR devices, which only measure the soil between the narrowly spaced rods of the TDR probe.

For example, the resonant frequency of the output signal (s) produced by a resonator utilized by embodiments of the present disclosure may be representative of the permittivity across the volume of soil in which the resonator is disposed, including soil within an interior of the resonator. This is illustrated in FIGS. 40A and 40B where it is shown that the cylinder used to form the resonator device may be hollow, allowing the soil to fill the space on the interior of the cylinder, as well as surround the outside of the resonator device. The resonance of the output signals is dependent upon the water concentration within the soil surrounding the resonator. For example, the complex permittivity of water is different from that of the soil. Thus, the resonance is affected by the effective permittivity around the resonator, which is influenced by the concentration of water in the soil. By configuring the resonators according to embodiments, the one or more parameters (e.g., S-parameters, resonant frequencies, and the like) of the output signals generated by the resonators utilized in the various systems described herein, including the systems described above with reference to FIGS. 35-39 and the systems described below with reference to FIGS. 41 and 42A-4C, may be used to more accurately determine the moisture content of the soil as compared to existing technologies, such as the aforementioned TDR systems. It is noted that although FIGS. 40A and 40B are described in terms of resonator devices that include metal patches and/or strips, any of the systems disclosed herein may readily utilize resonator devices formed using one or more coils, one or more metal patches and/or strips, or combinations of coils, metal patches, and/or metal strips.

Referring to FIG. 40C, a block diagram illustrating additional aspects of a resonator configuration for use in a system for determining an amount of liquid within a volume of a material according to embodiments of the present disclosure is shown. As shown in FIG. 40C, rather than having a single metal patch or strip, as in the configuration illustrated in FIG. 40A, in some embodiments, a resonator device may be formed using a plurality of coils, metal strips, and/or patches. For example, in FIG. 40C, a plurality of metal strips and/or patches 4020 have been wrapped around a cylinder 4022. In such a configuration, the different metal strips and/or patches 4020 may be utilized to estimate moisture contents of soil at different depths. It is noted that depending on the particular system in which the resonator device configuration of FIG. 4C is deployed, each of the plurality of metal patches and/or strips 4020 may be coupled to a reader device using leads (e.g., as in the configurations illustrated in FIGS. 35, 36), coupled to an antenna (e.g., as in the configuration illustrated in FIG. 39), coupled to in-ground circuitry (e.g., as in the configuration illustrated in FIG. 38), or may not be coupled to any additional devices or circuitry (e.g., as in the configuration illustrated in FIGS. 37A and 37B). Additionally, as described in more detail below with reference to FIG. 41, in some embodiments, resonator devices including a plurality of coils, metal patches, and/or strips may be deployed in an array configuration, which may enable probing of moisture content across a larger volume of soil.

In resonator device configurations including multiple resonator components (e.g., multiple coils, multiple metal patches and/or strips, etc.), each of the resonator components may be configured to have the same resonant frequency band. In such embodiments, the length for each resonator may be compensated by, for example, the wires coupling the resonators to the reader device. Additionally or alternatively, each of the resonator components may be configured to have its own resonant frequency band (e.g., the baseline of dry soil for each resonator is different). This may reduce or eliminate interference between the different resonators.

Referring to FIG. 40D, a block diagram illustrating additional aspects of a resonator configuration for use in a system for determining an amount of liquid within a volume of a material according to embodiments of the present disclosure is shown. As shown in FIG. 40D, resonators utilized in embodiments of the present disclosure may include resonators formed from metal patches and/or strips 4030 that form or have patterns embedded therein. The metal patches and/or strips 4030 may be wrapped around a cylinder 4032. The metal patterns may be configured as distributed capacitive and inductive elements that form a resonance pattern that is varied with the permittivity around the capacitive elements. For example, planar resonator metal patterns may be periodic, which are repeats of "unit cell" patterns. Each until cell contains capacitive and inductive elements, where capacitive patterns are associated with parallel metal strips with a gap, and inductive patterns are associated with straight lines or meander-lines of metal. The capacitive patterns may be sensitive to permittivity in the surrounding area. Thus, as the permittivity changes (e.g., due to water), the capacitive elements may become different, which means that the resonance from the combination of the capacitive and inductive elements also becomes different. The difference between this type of resonator (e.g., a patterned metal plate/strip resonator) and non-patterned metal plate/strip resonator is that the entire metal patch may have many distributed inductive and capacitive elements. In this manner, the sensing may be extended to a wide range of area instead of directly on the lumped-element capacitive electrodes. In principle, such resonators may be configured so that when at resonance, the reflection coefficient becomes maximum. In this manner, the system may be configured so that at resonance: 1) the reflection from the surface gives a stronger return signal; or 2) the transmission of the surface gives maximum signal and the reflection from the surface gives a minimum return signal. It is noted that the resonator configuration illustrated in FIG. 40D (e.g., a resonator device formed by wrapping a patterned metal patch and/or strip around a cylinder) may be utilized with various ones of the moisture content detection systems disclosed herein, such as the systems described and illustrated with reference to FIGS. 35-39, 41, and 42A-42C.

Referring to FIG. 41, a block diagram illustrating aspects of another system for determining an amount of liquid within a volume of a material according to embodiments of the present disclosure is shown as a system 4100. As shown in FIG. 41, the system 4100 includes a first resonator device 4110, a second resonator device 420, a processor 4130, and a plurality of control circuits 4142, 4144, 4146, 4152, 4154, 4156. The first resonator device 4110 may include a plurality of resonators 4112, 4114, 4116 and a cylinder 4118, and the second resonator device 4120 may include a plurality of resonators 4122, 4124, 4126 and a cylinder 4128. Depending on the particular configuration of the system 4100, the plurality of resonators 4112, 4114, 4116 and the plurality of resonators 4122, 4124, 4126 may each be formed from one or more coils, one or more metal patches and/or strips, and/or one or more patterned metal patches and/or strips that has been wrapped at least partially around a corresponding one of the cylinders 4118 and 4128. Additionally, as shown in FIG. 41, the first resonator device 4110 and the second resonator device 4120 may be disposed within a volume of soil.

Although not shown in FIG. 41 for simplicity of the figure, in embodiments, the processor 4130 may be part of a reader device. Such a reader device may also include a memory, a power source, one or more input/output (I/O) ports, and a communication module. The memory may store instructions that, when executed by the processor 4130, cause the processor 4130 to perform the operations described in connection with the system 4100, such as controlling the operations of the system 4100 to determine the moisture content of the soil based on one or more parameters (e.g., S-parameters, resonant frequencies, and the like) associated with output signals generated by the plurality of resonators in response to input signals generated under the control of the processor 4130, as described in more detail below. Additionally, the memory may be configured to store measurement data, such as information associated with output signals generated by the resonators of the first resonator device 4110 and the second resonator device 4120, the one or more parameters associated with the output signals, estimates of the amount of liquid present in the volume, and other information. The reader device may be configured to timestamp the measurement data stored at the memory to facilitate monitoring of the amount of liquid over time. This may enable the measurement data to be subsequently analyzed and correlated with various events, such as rainfall, activation of an irrigation system, and the like, which may provide insights into how those events impact the amount of liquid within the soil over time.

Each of the control circuits 4142, 4144, 4146, 4152, 4154, 4156 may include various circuitry for generating input signals that are to be provided to the various resonators of the system 4100. For example, the control circuit 4142 may generate input signals that are provided to the resonator 4112, the control circuit 4144 may generate input signals that are provided to the resonator 4114, the control circuit 4146 may generate input signals that are provided to the resonator 4146, the control circuit 4152 may generate input signals that are provided to the resonator 4122, the control circuit 4154 may generate input signals that are provided to the resonator 4124, and the control circuit 4156 may generate input signals that are provided to the resonator 4126.

The control circuits 4142, 4144, 4146, 4152, 4154, 4156 may operate as a signal processing device configured to condition the one or more input signals provided to the resonators. For example, each of the control circuits 4142, 4144, 4146, 4152, 4154, 4156 may include a phase shifter circuit and an impedance matching circuit configured to generate the input signals. The resonance may be identified by the magnitude and/or the phase of reflection coefficients. At resonance, the spectral response for magnitude may show a null. However, if the impedance is not matched at the baseline, the null may not obvious. This means the resonance quality factor may be low. However, when the impedance is matched at the baseline, the magnitude at resonance becomes a clear null (minimum) with a much higher quality factor. Therefore, including the impedance matching circuit may make it is easier to identify the resonance by providing sharp spectral shapes that more clearly indicate changes of resonance. At the resonant frequency, the phase becomes 180 degrees different in the frequency spectrum. This sharp change of phase may be easily observed, and from the phase change observation, the resonant frequency may be identified. A phase shifter may be used to shift the phases to have abrupt phase change at the desired resonant frequency, and the added phase may be used to find the resonant frequency (e.g., because there is a relationship between the phase and resonant frequency). The input signals may be configured to induce electromagnetic wave propagation at a specific angle, which enables the system 4100 to probe a wider area of soil and obtain multidimensional scattering parameters. Using the resonator array configuration of the system 4100 may facilitate rapid probing of moisture content within soil at different depths and across a large area or volume of soil than configurations that utilize a single resonator device.

For example, upon providing the input signals to the various resonators 4112, 4114, 4116, 4122, 4124, 4126, various output signals may be generated. The output signals may be detected by the receiver device (e.g., by the processor 4130). The processor 4130 may be configured to analyze the output signal generated by the resonators 4112, 4114, 4116, 4122, 4124, 4126 to determine the amount of liquid within the soil. For example, the output signals may be analyzed by the processor 4130 to identify one or more resonant frequencies associated with each of the output signals, and then, as described above, the identified resonant frequencies of the output signals may be used to determine the moisture content of the soil.

As shown above, the system 4100 enables determinations to be made regarding an amount of liquid, such as water, within a volume of soil. The system 4100 provides several advantages over existing technologies, such as the aforementioned TDR devices. For example, the system 4100 consumes less power than existing TDR devices (e.g., because the resonators utilized by the system 4100 may operate at low power). Additionally, while TDR devices are limited to measurements at the surface of their respective sensors (e.g., they only measure resistance when water is on top of the film that covers the sensor), the system 4100 is configured to detect moisture contents within the soil based on an overall dielectric constant of a volume of soil in which the resonator devices 4110 and 4120 are disposed. For example, the resonant frequency of the output signals produced by the resonators of the resonator devices 4110 and 4120 may be representative of the dielectric constant of across the volume of soil where the resonator devices 4110 and 4120 are disposed.

Referring to FIG. 42A, a block diagram illustrating aspects of another system for determining an amount of liquid within a volume of a material according to embodiments of the present disclosure is shown as a system 4200. As shown in FIG. 42A, the system 4200 may include a resonator device 4210 and a processor 4220. In embodiments, the processor 4220 may be a processor of a reader device, such as the reader device 3520 of FIG. 35 or the reader device 3620 of FIG. 36.

In embodiments, the resonator device 4210 may be arranged as spiral coil of wire, and may be inserted into a volume of soil by placing a first end 4204 of the resonator device 4210 on a surface of the soil and then rotating the resonator device 4210 into the soil using a screw-rotation motion, as shown at 4201. A second end 4204 of the resonator device 4210 may be coupled to the processor 4220 via leads 4222, 4224. Referring briefly to FIGS. 42B and 42C, block diagrams illustrating cross-section views of the resonator device 4210 proximate the first end 4202 (e.g., FIG. 42B) and the second end 4204 (e.g., FIG. 42C) are shown. As shown in FIGS. 42B and 42C, the resonator device 4210 may include a first wire 4212 and a second wire 4214. The first wire 4212 and the second wire 4214 may be insulated. At the first end 4202, the first wire 4212 may be coupled to the lead 4222 and the second wire 4214 may be coupled to the lead 4224. At the second end 4204, the first wire 4212 may be coupled to the second wire 4214 via a connection 4216 (e.g., to provide a return signal). Additionally, as shown in FIGS. 42B and 42C, the first wire 4212 and the second wire 4214 may be disposed within a protective covering 4211 (e.g., to prevent corrosion of the first and second wires 4112, 4114).

In embodiments, the first wire 4212 may correspond to a sensing wire configured to generate an output signal having one or more resonant frequencies corresponding to the surrounding soil, and the second wire 4214 may operate to output the signal generated by the first wire 4212 to a reader device. For example, the processor 4220 may initiate analysis by causing one or more input signals to be provided to the first wire 4212. In embodiments, the input signals may be provided to the first wire 4212 via the lead 4222. The input signals may cause the first wire 4212 to generate the output signals, which are provided to the second wire 4214 via the connection 4216 and returned to the reader device (e.g., to the processor 4220) via the second wire 4214 and the second lead 4224. Upon receiving the output signals, the processor 4120 may analyze the output signals generated by the resonator device 4210 to determine the amount of liquid within the soil. For example, the output signals may be analyzed by the processor 4220 to identify one or more resonant frequencies associated with each of the output signals, and then, as described above, the identified resonant frequencies of the output signals may be used to determine the moisture content of the soil.

As shown above, the system 4200 enables determinations to be made regarding an amount of liquid, such as water, within a volume of soil. The system 4200 provides several advantages over existing technologies, such as the aforementioned TDR devices. For example, as explained above with reference to FIG. 35, the system 4200 may facilitate analysis of moisture content over a larger volume of soil than existing TDR devices (e.g., because TDR devices only measure the soil between the narrowly spaced rods of the TDR probe), as described above with respect to FIGS. 40A-40D.

As briefly described above with reference to FIGS. 40A-40D, the systems described above with reference to FIGS. 35-42C may utilize resonator devices that are formed from coils and/or metal patches/strips wrapped around hollow cylinders, allowing the soil in which the resonator device is disposed fill the hollow portion as well as surround the outside of the resonator device. However, in some embodiments, solid core resonator devices may be utilized. For example, the interior region of the cylinder may be filled with a material of a known permittivity, such as plastic, water, or air, and the top and bottom of the cylinder may be sealed by a cap or other covering. In some embodiments, dry soil from the area in which the resonator device is to be deployed may be placed inside the enclosed cylinder, which may be used to calibrate the resonator device prior to, or after it is disposed in the soil. In some embodiments, the cover or cap used to seal the bottom portion of the resonator device may be formed in the shape of a cone (or some other shape), which may assist with insertion of the resonator device into the soil.

The various system configurations illustrated with reference to FIGS. 35-42 may further provide additional benefits and advantages. For example, observations and measurements obtained by a reader device (e.g., the reader device 3520 of FIG. 35, the reader device 3720 of FIGS. 37A and 37B, the reader device 3830 of FIG. 38, the reader device 3920 of FIG. 39, the reader device 4130 of FIG. 41 (if configured to include wireless communication capabilities), and/or the reader device that includes the processor 4220 of FIG. 42 (if configured to include wireless communication capabilities)) may be retrieved from the field using a drone or other vehicle.

In an exemplary scenario, the drone may be coupled to the reader device (e.g., the reader device 3720 of FIGS. 37A and 37B, the reader device 3830 of FIG. 38, the reader device 3920 of FIG. 39) and may be navigated into proximity (e.g., a few meters, 10 meters, 50 meters, or some other distance that facilitates communication between the reader device and the resonator) with a resonator device. Once in proximity, the reader device may generate the input signals, and detect the output signals generated by the resonator(s). The moisture content of the soil may then be estimated based on one or more parameters associated with the output signals. In another exemplary scenario, the drone may be equipped with a device configured to communicate with a local reader device (e.g., the reader device 3520 of FIG. 35, the reader device 4130 of FIG. 41 (if configured to include wireless communication capabilities), and/or the reader device that includes the processor 4220 of FIG. 42 (if configured to include wireless communication capabilities)) via a wireless communication link. In such a scenario, the drone may be navigated into proximity with the local reader device, and, once in proximity, may establish a communication session with the local reader device to retrieve measurement data from the local reader device, such as measurement data associated with prior interrogations of the resonator by the local reader device and/or prior estimates of moisture contents of the soil at the location where the local reader device is deployed. In still another scenario, rather than utilizing a drone, a reader device or device configured to communicate with a local reader device may be integrated with a vehicle, and the vehicle may be navigated into proximity of one or more locations where resonators configured according to embodiments have been deployed to obtain and/or retrieve measurement data and/or moisture content data.

Utilizing drones and/or vehicles to obtain the measurement data may enable measurements to be retrieved from various locations spread out across a large area more quickly. Additionally, the drones may be equipped with more powerful wireless communication capabilities that enable the obtained measurement data and/or moisture content data to be transmitted to a central location, providing faster access to the data. Additionally, the process or obtaining the data may be automated. For example, global positioning system (GPS) coordinates of each resonator device deployed across a geographic area may be recorded, and the drone may be programmed to automatically navigate to the recorded GPS locations to obtain the measurement data and/or moisture content data.

Referring to FIG. 43, a flow diagram illustrating aspects of an exemplary method for determining an amount of liquid within a volume of a material according to embodiments of the present disclosure is shown as a method 4300. In embodiments, the steps of the method 4300 may be stored in a memory as instructions that, when executed by one or more processors, cause the one or more processors to perform operations to determine moisture content of a volume of material in accordance with embodiments of the present disclosure. Additionally, it is noted that the various steps of the method 4300 may be performed by various ones of the systems illustrated and described above with reference to FIGS. 35-42C.

At step 4310, the method includes detecting, by a reader device, an output signal generated by a resonator in response to an input signal. In embodiments, the output signal may be generated by the resonator while the resonator is disposed within a material, such as soil. It is noted that the output signal may be generated by any of the resonators described above with respect to FIGS. 35-42C. For example, reader device may be the reader device 3520 and the output signal may be generated by the resonator 3510, as described above with reference to FIG. 35. Additionally, the reader device may be the reader device 3620 and the output signal may be generated by the resonator 3610, as described above with reference to FIG. 36. The reader device may also be may be the reader device 3720 and the output signal may be generated by the resonator 3710, as described above with reference to FIGS. 37A and 37B. As another example, the reader device may be the reader device 3830 and the output signal may be generated by the resonator 3810, as described above with reference to FIG. 38. In yet another example, the reader device may be the reader device 3920 and the output signal may be generated by the resonator 3910, as described above with reference to FIG. 39. In a further example, the output signal may be generated by one of the resonators 4112, 4114, 4116, 4122, 4124, 4126 of FIG. 41 and the reader device may be a reader device (not shown in FIG. 41) that includes the processor 4130 of FIG. 41. Further, the output signal may be generated by the resonator 4210 of FIG. 42 and the reader device may be a reader device (not shown in FIG. 42) that includes the processor 4220 of FIG. 42.

At step 4320, the method 4300 includes estimating, by a processor, an amount of a liquid within the material based on one or more parameters associated with the output signal(s). In embodiments, estimating the amount of the liquid within the material may include determining the one or more parameters associated with the output signal(s), as described above with reference to FIG. 4. In embodiments, one or more parameters associated with the output signal(s) may include one or more scattering parameters (e.g., one or more S11, S12, S21, S22 parameters), a resonant frequency of the output signal(s), or a combination thereof, as described above with reference to FIG. 4. In embodiments, estimating the amount of the liquid within the material may include determining one or more signatures associated with a material within the volume based on the one or more parameters, and comparing the one or more signatures to signatures associated with known moisture content, as described above with reference to FIG. 4.

As an illustrative example, phase and amplitude measurements associated with reflection coefficients at multiple frequencies may be obtained based on the output signals generated by the resonator(s). From these measurements, the real and imaginary parts of the permittivity around the resonator may be calculated (or obtained from simulations). The real part of permittivity responds to conductivity of the soil, which is mainly related to ion concentrations, and the imaginary part of permittivity is mainly affected by water contents of the soil. Thus, parameters such as reflection coefficients of observed resonant frequencies may be utilized to estimate the moisture contents of the soil.

In some embodiments, the method 4300 may be implemented in a system configuration where the reader device is coupled to the resonator, such as the configurations illustrated in FIGS. 35 and 36. In such embodiments, the reader device that is coupled to the resonator may generate the input signal, and may also transmit information representative of at least one of the output signal and the one or more parameters associated with the output signal to a remote device via a wireless communication link (e.g., FIG. 35) or a wired communication link (e.g., FIG. 36). In some embodiments, rather than sending the information representative of the output signal, the one or more parameters, or both, the reader device may be configured to determine and transmit the estimated amount of the liquid within the material to a remote device via at least one of a wired communication link and a wireless communication link. In some embodiments of the method 4300, the reader device may not determine the amount of the liquid and may instead, transmit the information representative of the output signal, the one or more parameters, or both to the remote device, and a processor of the remote device may estimate the amount of the liquid within the material. In embodiments, the reader device and/or a remote device communicatively coupled to the reader device may be configured to control one or more systems based on the estimated amount of the liquid, such as providing a control signal to activate a sprinkler system (e.g., when the amount of the liquid is below a threshold).

As described above, in some embodiments, the resonator may be coupled to an activation device, such as the activation device described above with reference to FIG. 38. In such embodiments, the method 4300 may further include receiving, by the activation device, a wireless signal from the reader device, and generating, by the activation device, the input signal in response to receiving the wireless signal. For example, as explained above with reference to FIG. 38, the reader device may generate an input signal 3835 that is received by the activation device, and in response to receiving the input signal 3835, the activation device (e.g., VCO/AMP 3826) may generate an input signal that causes the resonator 3810 to produce the output signal 3811, which is subsequently received/detected by the reader device. As described above with reference to FIG. 39, in some embodiments, the reader device may be configured to sweep a frequency of the input signals provided to the resonator.

In embodiments, the method 4300 may also include calibrating the resonator. Calibration of the resonator may include measuring the reflection coefficient(s) (or other parameters) over the frequency band, as described above with reference to FIG. 1, using a dry sample of the material (e.g., the soil, or equivalent modeling phantom). The reflection coefficient(s) (or other parameters) may then be measured over the frequency band as known percentages (by weight) of water are added to the material. Phases of the reflection coefficient(s) may indicate the resonant frequencies, and the magnitude of the reflection coefficient(s) may be recorded. It is noted that nulls of the magnitudes also confirm the resonant frequencies. Based on the respective resonant frequencies, calibration curves may be established, and multiple resonant frequencies may provide multiple signatures. Polynomial of a high order curve fitting may be used to establish the calibration standards, and frequency shifts in the observed metrics may be used to determine the water concentrations.

In some embodiments, calibration may be performed while the resonator device is disposed within the material (e.g., in the field). For example, when the soil surrounding the resonator device (e.g., one of the resonators illustrated in FIGS. 35-42C), the reflection coefficients may be measured, which provides a baseline measurement. Known quantities of water may be added to the soil and additional measurements may be recorded, as described above. Based on these measurements, signatures representative of different soil moisture content may be generated, which may subsequently be used to estimate the moisture content of the soil using the various systems described above with reference to FIGS. 35-42.

As described above with reference to FIGS. 35-43, embodiments of systems and methods for determining moisture content of a material, such as soil, with improved accuracy are disclosed. These various systems and methods utilize resonators formed using one or more coils, one or more metal patches, one or more metal strips, and/or one or more patterned metal patches that are vertically inserted into the soil, and provide improved detection of moisture content based on characteristics of output signals generated by the resonators. Further, embodiments provide improved systems and methods for obtaining measurement data from the resonators, such as utilizing reader devices configured to be attached to drones or other vehicles, as well as via wired and/or wireless communication networks. Still further, embodiments may operate to facilitate passive sensing of moisture content in the material.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the methods and systems are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary structure, and/or connections may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A method for determining one or more characteristics of a material, the method comprising:

detecting, by a reader device coupled to a resonator, an output signal generated by the resonator in response to an input signal received at the resonator, wherein the resonator is disposed within soil; and estimating, by a processor, an amount of a liquid within the soil based on parameter data extracted from the output signal, the parameter data corresponding to parameters comprising at least one scattering parameter and a resonant frequency.

2. The method of claim 1, wherein the at least one scattering parameter corresponds to a reflection coefficient, the method further comprising:

generating, by the reader device, the input signal;

generating, by the processor, phase measurements at multiple frequencies and amplitude measurements at the multiple frequencies, the phase measurements and the amplitude measurements based on the reflection coefficient; and determining, by the processor, a complex permittivity based on the phase measurements and based on the amplitude measurements, the complex permittivity associated with the soil and associated with the liquid, wherein a real component of the complex permittivity corresponds to a conductivity of the soil and an imaginary component of the complex permittivity corresponds to the amount of the liquid.

3. The method of claim 1, wherein the resonator comprises a plurality of metallic strips patterned onto a substrate, wherein a first set of the plurality of metallic strips are capacitive, and wherein a second set of the plurality of the metallic strips are inductive, the method further comprising transmitting, by the reader device, information representative of at least one of the output signal and the parameters associated with the output signal to a remote device.

4. The method of claim 3, wherein the reader device is communicatively coupled to the remote device via at least one of a wired communication link and a wireless communication link, wherein the liquid comprises water, wherein the substrate is shaped to be disposed within the soil, and wherein the substrate is cylindrical.

5. The method of claim 3, wherein the processor is integrated with the remote device.

6. The method of claim 1, wherein the processor is integrated with the reader device, and wherein the method includes transmitting, by the reader device, the estimated amount of the liquid within the soil to a remote device via at least one of a wired communication link and a wireless communication link.

7. The method of claim 1, wherein the resonator is coupled to an activation device, and wherein the method includes:

receiving, by the activation device, a wireless signal from the reader device; and generating, by the activation device, the input signal in response to receiving the wireless signal, wherein the activation device is integrated into a drone.

8. The method of claim 1, wherein the resonator is coupled to an antenna, and wherein the method includes transmitting, by the reader device, the input signal.

9. A system comprising:

a resonator;

a reader device configured to detect an output signal generated by the resonator in response to an input signal; and a processor configured to estimate an amount of a liquid within soil in which the resonator is disposed, wherein an estimate of the amount of the liquid is based on parameter data extracted from the output signal, the parameter data corresponding to parameters comprising at least one scattering parameter and a resonant frequency.

10. The system of claim 9, wherein the reader device is coupled to the resonator, wherein the reader device is configured to generate the input signal, and further comprising a control circuit, wherein the control circuit includes an impedance matching circuit configured to identify the resonant frequency.

11. The system of claim 9, wherein the reader device is configured to transmit information representative of at least one of the output signal and the parameters associated with the output signal to a remote device via at least one of a wired communication link and a wireless communication link, and wherein the processor is integrated within the remote device.

12. The system of claim 10, wherein the at least one scattering parameter corresponds to a reflection coefficient, and wherein the control circuit further includes a phase shifter configured to shift a phase of the reflection coefficient to identify the resonant frequency.

13. The system of claim 9, wherein the processor is integrated with the reader device, and wherein the reader device is configured to transmit the estimated amount of the liquid within the material to a remote device via at least one of a wired communication link and a wireless communication link.

14. The system of claim 9, further comprising:

an activation device coupled to the resonator, wherein the activation device is configured to:

receive a wireless signal from the reader device; and generate the input signal in response to receiving the wireless signal.

15. The system of claim 9, further comprising an antenna coupled to the resonator, wherein the reader device is configured to transmit the input signal, and wherein the resonator is configured to generate the output signal based on reception of the input signal at the antenna.

16. A system comprising:

a plurality of resonators;

a reader device configured to detect output signals generated by each of the plurality of resonators in response to one or more input signals, wherein the plurality of resonators are disposed within soil; and a processor configured to estimate an amount of a liquid within the soil based on parameter data extracted from the output signal, the parameter data corresponding to parameters comprising at least one scattering parameter and a resonant frequency.

17. The system of claim 16, wherein the reader device is coupled to each of the plurality of resonators, and wherein the reader device is configured to generate the one or more input signals, and wherein the at least one scattering parameter corresponds to a reflection coefficient.

18. The system of claim 16, wherein the reader device is configured to transmit information representative of at least one of the output signal and the one or more parameters associated with the output signal to a remote device via at least one of a wired communication link and a wireless communication link, and wherein the processor is integrated with the remote device.

19. The system of claim 16, wherein the processor is integrated with the reader device, and wherein the reader device is configured to transmit the estimated amount of the liquid within the soil to a remote device via at least one of a wired communication link and a wireless communication link.

20. The system of claim 16, further comprising a plurality of signal processing devices configured to condition the one or more input signals for reception by the plurality of resonators.

* * * * *